(12) United States Patent
Bee et al.

(10) Patent No.: US 11,402,545 B2
(45) Date of Patent: Aug. 2, 2022

(54) STRUCTURALLY-COLORED ARTICLES AND METHODS FOR MAKING AND USING STRUCTURALLY-COLORED ARTICLES

(71) Applicant: NIKE, Inc., Beaverton, OR (US)

(72) Inventors: Jennifer Bee, Portland, OR (US); Jeremy Gantz, Lake Oswego, OR (US); Kim Kovel, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 142 days.

(21) Appl. No.: 16/825,629

(22) Filed: Mar. 20, 2020

(65) Prior Publication Data
US 2020/0217986 A1   Jul. 9, 2020

Related U.S. Application Data

(62) Division of application No. 16/146,614, filed on Sep. 28, 2018, now Pat. No. 10,732,322.
(Continued)

(51) Int. Cl.
*B32B 33/00* (2006.01)
*B32B 7/023* (2019.01)
(Continued)

(52) U.S. Cl.
CPC ............... *G02B 1/04* (2013.01); *A41D 27/08* (2013.01); *A43B 1/0027* (2013.01); *A43B 1/0072* (2013.01); *A43B 1/14* (2013.01); *A43B 13/04* (2013.01); *A43B 13/122* (2013.01); *A43B 13/14* (2013.01); *A43B 13/188* (2013.01); *A43B 13/20* (2013.01); *A43B 13/22* (2013.01); *A43B 21/28* (2013.01); *A43B 23/026* (2013.01); *A43B 23/24* (2013.01); *B05D 3/067* (2013.01); *B05D 5/063* (2013.01); *B05D 5/066* (2013.01);
(Continued)

(58) Field of Classification Search
CPC .. A43B 13/20; B32B 1/00; B32B 3/30; B32B 7/023; B32B 27/08; B32B 33/00; B32B 27/18; B32B 2255/10; B32B 2255/20; B32B 2255/26; B32B 2307/402; B32B 2307/409; B32B 2307/724; B32B 2437/02
See application file for complete search history.

(56) References Cited

U.S. PATENT DOCUMENTS 2,345,533 A   3/1944  De Witt
2,607,130 A   8/1952  Pearson
(Continued)

FOREIGN PATENT DOCUMENTS

AU   2007200128 A1   1/2007
BR   PI0503224 A     1/2007
(Continued)

OTHER PUBLICATIONS

International Preliminary Report on Patentability for PCT/US2020/022148 dated Sep. 29, 2021.
(Continued)

*Primary Examiner* — Michael C Miggins
(74) *Attorney, Agent, or Firm* — Thomas | Horstemeyer, LLP

(57) ABSTRACT

One or more aspects of the present disclosure are directed to bladders that incorporate a multi-layer optical film that impart a structural color to the bladder. The present disclosure is also directed to articles including the bladders having a multi-layer optical film, and methods for making articles and bladders having a multi-layer optical film.

20 Claims, 1 Drawing Sheet

Related U.S. Application Data

(60) Provisional application No. 62/633,666, filed on Feb. 22, 2018, provisional application No. 62/565,306, filed on Sep. 29, 2017, provisional application No. 62/565,310, filed on Sep. 29, 2017, provisional application No. 62/565,299, filed on Sep. 29, 2017, provisional application No. 62/565,313, filed on Sep. 29, 2017.

(51) Int. Cl.

| | | |
|---|---|---|
| *A43B 13/18* | (2006.01) | |
| *B32B 1/00* | (2006.01) | |
| *A43B 13/14* | (2006.01) | |
| *G02B 1/04* | (2006.01) | |
| *C09D 7/61* | (2018.01) | |
| *A41D 27/08* | (2006.01) | |
| *A43B 1/00* | (2006.01) | |
| *A43B 1/14* | (2006.01) | |
| *A43B 13/04* | (2006.01) | |
| *A43B 13/12* | (2006.01) | |
| *A43B 13/20* | (2006.01) | |
| *A43B 13/22* | (2006.01) | |
| *A43B 21/28* | (2006.01) | |
| *A43B 23/02* | (2006.01) | |
| *A43B 23/24* | (2006.01) | |
| *B05D 3/06* | (2006.01) | |
| *B05D 5/06* | (2006.01) | |
| *B29D 11/00* | (2006.01) | |
| *B32B 3/30* | (2006.01) | |
| *B32B 5/02* | (2006.01) | |
| *B32B 15/095* | (2006.01) | |
| *B32B 27/08* | (2006.01) | |
| *B32B 27/12* | (2006.01) | |
| *B32B 27/34* | (2006.01) | |
| *B32B 27/40* | (2006.01) | |
| *B32B 37/00* | (2006.01) | |
| *B32B 38/06* | (2006.01) | |
| *C09D 5/00* | (2006.01) | |
| *D06M 10/06* | (2006.01) | |
| *D06M 11/46* | (2006.01) | |
| *D06M 11/83* | (2006.01) | |
| *D06P 1/44* | (2006.01) | |
| *G02B 1/10* | (2015.01) | |
| *G02B 5/08* | (2006.01) | |
| *G02B 5/26* | (2006.01) | |
| *G02B 5/28* | (2006.01) | |
| *A41D 1/089* | (2018.01) | |
| *A41B 1/08* | (2006.01) | |
| *A41B 11/00* | (2006.01) | |
| *A41D 1/04* | (2006.01) | |
| *A41D 13/01* | (2006.01) | |
| *A42B 1/004* | (2021.01) | |
| *A43B 5/00* | (2022.01) | |
| *A45F 3/04* | (2006.01) | |
| *A63B 41/08* | (2006.01) | |
| *A63B 71/14* | (2006.01) | |
| *B23B 27/18* | (2006.01) | |
| *B32B 27/18* | (2006.01) | |
| *C08K 3/28* | (2006.01) | |
| *D06M 101/38* | (2006.01) | |

(52) U.S. Cl.
CPC .... *B29D 11/0074* (2013.01); *B29D 11/00865* (2013.01); *B32B 1/00* (2013.01); *B32B 3/30* (2013.01); *B32B 5/02* (2013.01); *B32B 5/022* (2013.01); *B32B 5/024* (2013.01); *B32B 7/023* (2019.01); *B32B 15/095* (2013.01); *B32B 27/08* (2013.01); *B32B 27/12* (2013.01); *B32B 27/34* (2013.01); *B32B 27/40* (2013.01); *B32B 33/00* (2013.01); *B32B 37/025* (2013.01); *B32B 38/06* (2013.01); *C09D 5/002* (2013.01); *C09D 7/61* (2018.01); *D06M 10/06* (2013.01); *D06M 11/46* (2013.01); *D06M 11/83* (2013.01); *D06P 1/44* (2013.01); *G02B 1/10* (2013.01); *G02B 5/0816* (2013.01); *G02B 5/26* (2013.01); *G02B 5/28* (2013.01); *G02B 5/285* (2013.01); *A41B 1/08* (2013.01); *A41B 11/001* (2013.01); *A41D 1/04* (2013.01); *A41D 1/089* (2018.01); *A41D 13/01* (2013.01); *A42B 1/004* (2013.01); *A43B 5/00* (2013.01); *A45F 3/04* (2013.01); *A63B 41/08* (2013.01); *A63B 71/143* (2013.01); *B05D 2503/00* (2013.01); *B23B 27/18* (2013.01); *B32B 27/18* (2013.01); *B32B 2255/10* (2013.01); *B32B 2255/20* (2013.01); *B32B 2255/26* (2013.01); *B32B 2274/00* (2013.01); *B32B 2305/188* (2013.01); *B32B 2307/402* (2013.01); *B32B 2307/409* (2013.01); *B32B 2307/416* (2013.01); *B32B 2307/724* (2013.01); *B32B 2367/00* (2013.01); *B32B 2437/02* (2013.01); *C08K 3/28* (2013.01); *D06M 2101/38* (2013.01)

(56) References Cited

U.S. PATENT DOCUMENTS

| | | |
|---|---|---|
| 2,712,190 A | 7/1955 | Sobel |
| 2,929,803 A | 3/1960 | Frazer et al. |
| 3,011,383 A | 12/1961 | Sylvester |
| 3,060,513 A | 10/1962 | Klink |
| 3,376,403 A | 4/1968 | Driga |
| 3,698,930 A | 10/1972 | Fleurquin et al. |
| 4,231,369 A | 11/1980 | Sorensen et al. |
| 4,300,294 A | 11/1981 | Riecken |
| 4,523,005 A | 6/1985 | Szycher |
| 4,533,592 A | 8/1985 | Bingham |
| 4,705,356 A | 11/1987 | Berning et al. |
| 5,009,486 A | 4/1991 | Dobrowolski et al. |
| 5,269,995 A | 12/1993 | Ramanathan et al. |
| 5,334,690 A | 8/1994 | Schafheutle et al. |
| 5,346,934 A | 9/1994 | Chriss |
| 5,500,067 A | 3/1996 | Jenkner |
| 5,572,817 A | 11/1996 | Chien |
| 5,628,128 A | 5/1997 | Miller et al. |
| 5,671,495 A | 9/1997 | Chen |
| 5,713,141 A | 2/1998 | Mitchell et al. |
| 5,722,322 A | 3/1998 | Watanabe |
| 5,778,793 A | 7/1998 | Mello et al. |
| 5,813,148 A | 9/1998 | Guerra |
| 5,815,950 A | 10/1998 | Wang |
| 5,825,548 A | 10/1998 | Bornhorst et al. |
| 5,928,456 A | 7/1999 | Souparis |
| 5,930,921 A | 8/1999 | Sorofman et al. |
| 5,952,065 A | 9/1999 | Mitchell et al. |
| 5,969,076 A | 10/1999 | Lai et al. |
| 5,979,078 A | 11/1999 | McLaughlin |
| 6,013,340 A | 1/2000 | Bonk et al. |
| 6,082,025 A | 7/2000 | Bonk et al. |
| 6,127,026 A | 10/2000 | Bonk et al. |
| 6,147,726 A | 11/2000 | Kubota et al. |
| 6,157,489 A | 12/2000 | Bradley, Jr. et al. |
| 6,164,777 A | 12/2000 | Li et al. |
| 6,203,868 B1 | 3/2001 | Bonk et al. |
| 6,321,465 B1 | 11/2001 | Bonk et al. |
| 6,402,879 B1 | 6/2002 | Tawney et al. |
| 6,551,531 B1 | 4/2003 | Ford et al. |
| 6,666,983 B2 | 12/2003 | Marietti et al. |
| 6,761,959 B1 | 7/2004 | Bonkowshi et al. |
| 6,897,281 B2 | 5/2005 | Lubnin et al. |
| 6,922,906 B2 | 8/2005 | Choi et al. |

(56) References Cited

U.S. PATENT DOCUMENTS

| | | |
|---|---|---|
| 7,006,294 B2 | 2/2006 | Steenblik et al. |
| 7,405,879 B2 | 7/2008 | Wild et al. |
| 7,476,705 B2 | 1/2009 | Pajerski |
| 7,800,814 B2 | 9/2010 | Nishimura et al. |
| 7,848,008 B2 | 12/2010 | Nishimura et al. |
| 7,903,339 B2 | 3/2011 | Banerjee et al. |
| 7,955,695 B2 | 6/2011 | Argoitia |
| 8,264,637 B2 | 9/2012 | Cho et al. |
| 8,322,636 B2 | 12/2012 | Wu et al. |
| 8,339,597 B2 | 12/2012 | Dal Negro et al. |
| 8,408,470 B2 | 4/2013 | Komatsu et al. |
| 8,486,494 B2 | 7/2013 | Fukazawa et al. |
| 8,558,137 B2 | 10/2013 | Yuasa et al. |
| 8,685,185 B2 | 4/2014 | Guo et al. |
| 8,889,234 B2 | 11/2014 | Kwon et al. |
| 9,102,195 B2 | 8/2015 | Raksha et al. |
| 9,134,468 B2 | 9/2015 | Noizet et al. |
| 9,185,947 B2 | 11/2015 | Spencer et al. |
| 9,220,951 B1 | 12/2015 | Comeau |
| 9,279,771 B2 | 3/2016 | Aizenberg et al. |
| 9,420,848 B2 | 8/2016 | Campos, II et al. |
| 9,453,943 B2 | 9/2016 | Miyake et al. |
| 9,527,340 B2 | 12/2016 | Szumski et al. |
| 9,557,457 B2 | 1/2017 | Gocho et al. |
| 9,931,804 B2 | 4/2018 | Le et al. |
| 10,048,411 B2 | 8/2018 | Parker |
| 10,555,580 B2 | 2/2020 | Peyton |
| 10,649,113 B2 | 5/2020 | Bee |
| 10,779,617 B2 | 9/2020 | Iovu |
| 10,928,553 B2 | 2/2021 | Bee et al. |
| 11,129,444 B1 | 9/2021 | Kovel |
| 11,254,095 B2 | 2/2022 | Hart et al. |
| 2001/0053454 A1 | 4/2001 | Higashi |
| 2001/0028921 A1 | 10/2001 | Shaw et al. |
| 2001/0042321 A1 | 11/2001 | Tawney et al. |
| 2002/0028311 A1 | 3/2002 | Coppens et al. |
| 2002/0150629 A1 | 10/2002 | Nishimura et al. |
| 2002/0183133 A1 | 12/2002 | Sano |
| 2002/0191234 A1 | 12/2002 | Ishimoto et al. |
| 2003/0074808 A1 | 4/2003 | Weaver et al. |
| 2003/0086030 A1 | 5/2003 | Taniguchi et al. |
| 2004/0006889 A1 | 1/2004 | Chen |
| 2004/0112252 A1 | 6/2004 | Zimmermann et al. |
| 2004/0135921 A1 | 7/2004 | Murata et al. |
| 2004/0142185 A1 | 7/2004 | Takushima |
| 2004/0169928 A1 | 9/2004 | Nilsen et al. |
| 2004/0172855 A1 | 9/2004 | Aslanides |
| 2004/0173855 A1 | 9/2004 | Masuoka et al. |
| 2005/0031816 A1 | 2/2005 | Chang et al. |
| 2005/0056954 A1 | 3/2005 | Devlin et al. |
| 2005/0063067 A1 | 3/2005 | Phillips et al. |
| 2005/0207138 A1 | 9/2005 | Cheung |
| 2005/0211114 A1 | 9/2005 | Fahrenbach et al. |
| 2005/0260369 A1 | 11/2005 | Graf et al. |
| 2005/0268497 A1 | 12/2005 | Alfaro et al. |
| 2005/0274041 A1 | 12/2005 | Collett et al. |
| 2006/0023327 A1 | 2/2006 | Coombs et al. |
| 2006/0090373 A1 | 5/2006 | Savoie et al. |
| 2006/0101671 A1 | 5/2006 | Berend et al. |
| 2006/0112599 A1 | 6/2006 | Braynock et al. |
| 2006/0128823 A1 | 6/2006 | Tsuchimura et al. |
| 2006/0198121 A1 | 9/2006 | Thorpe et al. |
| 2006/0270553 A1 | 11/2006 | Mori |
| 2007/0008439 A1 | 1/2007 | Nakayama et al. |
| 2007/0058260 A1 | 3/2007 | Steenblik et al. |
| 2007/0076069 A1 | 4/2007 | Edwards et al. |
| 2008/0040951 A1 | 2/2008 | Kates |
| 2008/0066347 A1 | 3/2008 | Suzuki |
| 2008/0248281 A1 | 10/2008 | Nakaguma et al. |
| 2008/0274359 A1 | 11/2008 | Lawrence et al. |
| 2008/0316628 A1 | 12/2008 | Nakajima et al. |
| 2009/0174944 A1 | 7/2009 | Yuasa et al. |
| 2009/0301649 A1 | 12/2009 | Augsberg et al. |
| 2010/0024597 A1 | 2/2010 | Dover et al. |
| 2010/0104810 A1 | 4/2010 | Fukazawa et al. |
| 2010/0152065 A1 | 6/2010 | Nishimura et al. |
| 2010/0177380 A1 | 7/2010 | Nagahama et al. |
| 2010/0199406 A1 | 8/2010 | Dua et al. |
| 2010/0199520 A1 | 8/2010 | Dua et al. |
| 2010/0222442 A1 | 9/2010 | Prissok et al. |
| 2010/0245978 A1 | 9/2010 | Baumberg et al. |
| 2010/0254007 A1 | 10/2010 | Toda |
| 2010/0266946 A1 | 10/2010 | Shirai et al. |
| 2010/0290109 A1 | 11/2010 | Kurt et al. |
| 2010/0291358 A1 | 11/2010 | Takahashi et al. |
| 2011/0026208 A1 | 2/2011 | Utsuro et al. |
| 2011/0033670 A1 | 2/2011 | Nishikawa et al. |
| 2011/0043911 A1 | 2/2011 | Kaneiwa et al. |
| 2011/0090564 A1 | 4/2011 | Utsuro et al. |
| 2011/0123754 A1 | 5/2011 | Shirai et al. |
| 2011/0171440 A1 | 7/2011 | Cheng et al. |
| 2011/0183111 A1 | 7/2011 | Yuasa et al. |
| 2011/0234953 A1 | 9/2011 | Amimori et al. |
| 2011/0234969 A1 | 9/2011 | Amimori et al. |
| 2011/0253288 A1 | 10/2011 | Xie et al. |
| 2011/0262675 A1 | 10/2011 | Inamiya et al. |
| 2011/0298207 A1 | 12/2011 | Despland et al. |
| 2011/0299150 A1 | 12/2011 | Steenblik et al. |
| 2012/0015118 A1 | 1/2012 | Zheludev et al. |
| 2012/0015145 A1 | 1/2012 | Depres |
| 2012/0034291 A1 | 2/2012 | Amsden et al. |
| 2012/0121820 A1 | 5/2012 | Kaplan et al. |
| 2012/0133672 A1 | 5/2012 | Joo |
| 2012/0139230 A1 | 6/2012 | Whiteman et al. |
| 2012/0186102 A1 | 7/2012 | Lee et al. |
| 2012/0204443 A1 | 8/2012 | Vertuccio |
| 2012/0231489 A1 | 9/2012 | Lenhert |
| 2012/0236415 A1 | 9/2012 | Nagano et al. |
| 2012/0249718 A1 | 10/2012 | Sohn et al. |
| 2012/0255201 A1 | 10/2012 | Little |
| 2012/0255452 A1 | 10/2012 | Bower et al. |
| 2012/0276332 A1 | 11/2012 | Conolly et al. |
| 2012/0297642 A1 | 11/2012 | Schaefer et al. |
| 2013/0004721 A1 | 1/2013 | Hara et al. |
| 2013/0004722 A1 | 1/2013 | Hara et al. |
| 2013/0004731 A1 | 1/2013 | Hara et al. |
| 2013/0004754 A1 | 1/2013 | Hara et al. |
| 2013/0148221 A1 | 6/2013 | Banerjee et al. |
| 2013/0182300 A1 | 7/2013 | Muller et al. |
| 2013/0183487 A1 | 7/2013 | Henze et al. |
| 2013/0243693 A1 | 9/2013 | Omenetto et al. |
| 2013/0250229 A1 | 9/2013 | Kaneiwa et al. |
| 2013/0330710 A1 | 12/2013 | Omenetto et al. |
| 2014/0016177 A1 | 1/2014 | Aizenberg et al. |
| 2014/0020192 A1 | 1/2014 | Jones et al. |
| 2014/0050899 A1 | 2/2014 | Kukoff |
| 2014/0104686 A1 | 4/2014 | Yuasa et al. |
| 2014/0106139 A1 | 4/2014 | Abrams |
| 2014/0109442 A1 | 4/2014 | Thompson |
| 2014/0118360 A1 | 5/2014 | Ma et al. |
| 2014/0161974 A1 | 6/2014 | Erho et al. |
| 2014/0182169 A1 | 7/2014 | Mack |
| 2014/0250734 A1 | 9/2014 | Zheng |
| 2014/0254017 A1 | 9/2014 | Manoharan et al. |
| 2015/0001840 A1 | 1/2015 | Parker |
| 2015/0035269 A1 | 2/2015 | Hooper et al. |
| 2015/0076808 A1 | 3/2015 | Kim et al. |
| 2015/0109657 A1 | 4/2015 | Baumberg et al. |
| 2015/0118124 A1 | 4/2015 | Khorasaninejad et al. |
| 2015/0146280 A1 | 5/2015 | Degott et al. |
| 2015/0192897 A1 | 7/2015 | Schilling et al. |
| 2015/0198749 A1 | 7/2015 | Ye et al. |
| 2015/0202834 A1 | 7/2015 | Free et al. |
| 2015/0250263 A1 | 9/2015 | Robinson, Jr. |
| 2015/0283743 A1 | 10/2015 | Park et al. |
| 2015/0309232 A1 | 10/2015 | Banerjee |
| 2015/0352883 A1 | 12/2015 | Schmid et al. |
| 2015/0352888 A1 | 12/2015 | Schmid et al. |
| 2016/0064696 A1 | 3/2016 | Collier et al. |
| 2016/0101601 A1 | 4/2016 | Abrams |
| 2016/0116645 A1 | 4/2016 | Parker |
| 2016/0128433 A1 | 5/2016 | Downing et al. |
| 2016/0131808 A1 | 5/2016 | Kristensen et al. |
| 2016/0146984 A1 | 5/2016 | Jiang et al. |

(56) References Cited

U.S. PATENT DOCUMENTS

| | | |
|---|---|---|
| 2016/0168386 A1 | 6/2016 | Aizenberg et al. |
| 2016/0176223 A1 | 6/2016 | Degott et al. |
| 2016/0178493 A1 | 6/2016 | Kawanaka et al. |
| 2016/0202394 A1 | 7/2016 | Clausen et al. |
| 2016/0202401 A1 | 7/2016 | Christiansen et al. |
| 2016/0209642 A1 | 7/2016 | Aizenberg et al. |
| 2016/0209678 A1 | 7/2016 | Nishimoto |
| 2016/0282527 A1 | 9/2016 | Saito et al. |
| 2016/0325310 A1 | 11/2016 | Schmid et al. |
| 2016/0327708 A1 | 11/2016 | Liles et al. |
| 2017/0023711 A1 | 1/2017 | Jiang et al. |
| 2017/0081535 A1 | 3/2017 | Kohri et al. |
| 2017/0087691 A1 | 3/2017 | Yokoyama et al. |
| 2017/0090084 A1 | 3/2017 | Wilson et al. |
| 2017/0129200 A1 | 5/2017 | Adami et al. |
| 2017/0157653 A1 | 6/2017 | Parker |
| 2017/0248746 A1 | 8/2017 | Banerjee et al. |
| 2017/0347745 A1 | 12/2017 | Figur et al. |
| 2018/0252158 A1 | 9/2018 | Malkamaki et al. |
| 2018/0257360 A1 | 9/2018 | Liponkoski |
| 2018/0284330 A1 | 10/2018 | Parker |
| 2018/0357316 A1 | 12/2018 | Neuvonen |
| 2018/0372929 A1 | 12/2018 | Parker |
| 2019/0098946 A1 | 4/2019 | Bee et al. |
| 2019/0098958 A1 | 4/2019 | Bee et al. |
| 2019/0099967 A1 | 4/2019 | Bee et al. |
| 2019/0099968 A1 | 4/2019 | Bee et al. |
| 2019/0099978 A1 | 4/2019 | Bee et al. |
| 2019/0099979 A1 | 4/2019 | Bee et al. |
| 2019/0113655 A1 | 4/2019 | Bee et al. |
| 2019/0113656 A1 | 4/2019 | Bee et al. |
| 2019/0163011 A1 | 5/2019 | Cao |
| 2019/0346603 A1 | 11/2019 | Sahara et al. |
| 2019/0387830 A1 | 12/2019 | Dua et al. |
| 2020/0018876 A1 | 1/2020 | Chen et al. |
| 2020/0040882 A1 | 2/2020 | Kalmari et al. |
| 2020/0088908 A1 | 3/2020 | Bee et al. |
| 2020/0181550 A1 | 6/2020 | Kalmari et al. |
| 2020/0217986 A1 | 7/2020 | Bee et al. |
| 2020/0217987 A1 | 7/2020 | Bee et al. |
| 2020/0240667 A1 | 7/2020 | Lind |
| 2020/0269561 A1 | 8/2020 | Bee et al. |
| 2020/0275728 A1 | 9/2020 | Bee et al. |
| 2020/0290311 A1 | 9/2020 | Kim et al. |
| 2020/0305526 A1 | 10/2020 | Gantz et al. |
| 2020/0305527 A1 | 10/2020 | Gantz et al. |
| 2020/0308734 A1 | 10/2020 | Gantz et al. |
| 2020/0314185 A1 | 10/2020 | Makynen et al. |
| 2020/0371272 A1 | 11/2020 | Bee et al. |
| 2020/0407838 A1 | 12/2020 | Gantz et al. |

FOREIGN PATENT DOCUMENTS

| | | |
|---|---|---|
| CH | 702116 B1 | 5/2011 |
| CN | 1324222 A | 11/2001 |
| CN | 1799857 | 7/2006 |
| CN | 101356245 A | 1/2009 |
| CN | 101381903 A | 3/2009 |
| CN | 101396884 A | 4/2009 |
| CN | 101633786 A | 1/2010 |
| CN | 101666886 A | 3/2010 |
| CN | 101781860 A | 7/2010 |
| CN | 102548752 A | 7/2012 |
| CN | 102691202 A | 9/2012 |
| CN | 103173039 A | 6/2013 |
| CN | 103965699 A | 8/2014 |
| CN | 104334042 A | 2/2015 |
| CN | 104592971 A | 5/2015 |
| CN | 105050442 A | 11/2015 |
| CN | 105271796 A | 1/2016 |
| CN | 105862000 A | 8/2016 |
| CN | 106080001 A | 11/2016 |
| CN | 107111002 A | 8/2017 |
| DE | 4307648 A1 | 9/1994 |
| DE | 20200346 U1 | 4/2002 |
| DE | 102010025159 A1 | 12/2011 |
| EP | 0335309 A1 | 10/1989 |
| EP | 905530 A2 | 3/1999 |
| EP | 1560416 | 8/2005 |
| EP | 1624026 A1 | 2/2006 |
| EP | 1653256 A1 | 5/2006 |
| EP | 1923229 A1 | 5/2008 |
| EP | 2012148 A1 | 1/2009 |
| EP | 2077459 A1 | 7/2009 |
| EP | 2462908 A1 | 6/2012 |
| EP | 2508922 A1 | 10/2012 |
| EP | 2538247 A2 | 12/2012 |
| EP | 2642321 A1 | 9/2013 |
| EP | 3151042 A1 | 4/2017 |
| EP | 3244240 A1 | 11/2017 |
| EP | 3278150 A2 | 2/2018 |
| EP | 3290968 | 3/2018 |
| GB | 1358710 A | 7/1974 |
| GB | 2374818 A | 10/2002 |
| GB | 2481697 A | 1/2012 |
| GB | 2524840 A | 10/2015 |
| GB | 2525020 A | 10/2015 |
| JP | S601180 U | 1/1985 |
| JP | 2001516272 A | 9/2001 |
| JP | 2002524317 A | 8/2002 |
| JP | 2002530712 A | 9/2002 |
| JP | 2005153192 A | 6/2005 |
| JP | 2005174647 A | 6/2005 |
| JP | 2005226196 A1 | 8/2005 |
| JP | 2006288907 A | 10/2006 |
| JP | 2008515491 A | 5/2008 |
| JP | 2009205123 A | 9/2009 |
| JP | 2009211077 A | 9/2009 |
| JP | 2010111974 A | 5/2010 |
| JP | 2010201652 A | 9/2010 |
| JP | 2011085779 A | 4/2011 |
| JP | 2011104931 A | 6/2011 |
| JP | 2012159589 A | 8/2012 |
| JP | 2013-041027 | 2/2013 |
| JP | 2013-0411027 | 2/2013 |
| JP | 2013029805 A | 2/2013 |
| JP | 2013080049 A | 5/2013 |
| JP | 2014189719 A | 10/2014 |
| JP | 2015069076 A | 4/2015 |
| JP | 5740937 B2 | 7/2015 |
| JP | 2015520044 A | 7/2015 |
| JP | 2015529136 A | 10/2015 |
| JP | 2016502470 A | 1/2016 |
| JP | 2017032409 A | 2/2017 |
| KR | 101472929 B1 | 12/2014 |
| TW | 200628089 A | 8/2006 |
| WO | 9701972 A1 | 1/1997 |
| WO | 2000031571 A1 | 6/2000 |
| WO | WO2000031571 A1 | 6/2000 |
| WO | 2003046039 | 6/2003 |
| WO | 03068525 A1 | 8/2003 |
| WO | 003095657 A2 | 11/2003 |
| WO | 2007038097 A1 | 4/2007 |
| WO | 2007096914 A1 | 8/2007 |
| WO | 2008076339 A2 | 6/2008 |
| WO | 2007037393 A1 | 4/2009 |
| WO | 2009062341 A1 | 5/2009 |
| WO | 2010119248 A2 | 10/2010 |
| WO | 2011161482 A1 | 12/2011 |
| WO | 2010047322 A1 | 3/2012 |
| WO | 2012055105 A1 | 5/2012 |
| WO | 2013151547 A1 | 10/2013 |
| WO | 2014022049 A1 | 2/2014 |
| WO | 2014059424 A2 | 4/2014 |
| WO | 2014117673 A1 | 8/2014 |
| WO | 2014133514 A1 | 9/2014 |
| WO | 2015051367 A1 | 4/2015 |
| WO | 2015079652 A1 | 6/2015 |
| WO | WO2015079652 A1 | 6/2015 |
| WO | 2015151479 A1 | 10/2015 |
| WO | 2015170120 A1 | 11/2015 |
| WO | 2015195123 | 12/2015 |
| WO | 2016015973 A1 | 2/2016 |
| WO | 2016092014 A1 | 6/2016 |

(56) References Cited

FOREIGN PATENT DOCUMENTS

| | | | |
|---|---|---|---|
| WO | 2016103980 | A1 | 6/2016 |
| WO | 2016140779 | A1 | 9/2016 |
| WO | 2016156863 | A2 | 10/2016 |
| WO | 2016164551 | A1 | 10/2016 |
| WO | 2016/191255 | | 12/2016 |
| WO | 2016193252 | A1 | 12/2016 |
| WO | 2017006314 | A1 | 1/2017 |
| WO | 2017032928 | A1 | 3/2017 |
| WO | 2017041085 | A1 | 3/2017 |
| WO | 2017115806 | A1 | 7/2017 |
| WO | 2017151496 | A1 | 9/2017 |
| WO | 2018130856 | A1 | 7/2018 |
| WO | 2018160866 | A1 | 9/2018 |
| WO | 2019038560 | A | 2/2019 |
| WO | 2019067969 | A1 | 4/2019 |
| WO | 2019086770 | A1 | 5/2019 |
| WO | 2019224426 | A1 | 11/2019 |
| WO | 2020013229 | A1 | 1/2020 |
| WO | 2020030844 | A1 | 2/2020 |
| WO | 2020197774 | A1 | 10/2020 |

OTHER PUBLICATIONS

Texture—www.vocabulary.com, Jun. 2, 2020 (Year: 2020).
Color—www.dictionary.com, Jun. 2, 2020 (Year: 2020).
Written Opinion of the International Preliminary Examining Authority for PCT/2020/022099 dated Dec. 1, 2020.
International Preliminary Report on Patentability for PCT/US2018/053516 dated Apr. 9, 2020.
International Preliminary Report on Patentability for PCT/US2018/053502 dated Apr. 9, 2020.
International Preliminary Report on Patentability for PCT/US2018/053488 dated Mar. 31, 2020.
Written Opinion of the International Preliminary Examining Authority for PCT/US2018/053510 dated Sep. 24, 2019.
International Search Report and Written Opinion for PCT/US2020/022099 dated Jun. 22, 2020.
International Search Report and Written Opinion for PCT/US2020/022129 dated Jun. 8, 2020.
International Search Report and Written Opinion for PCT/US2020/022148 dated Jul. 15, 2020.
Iohara et al: "Structurally Colored Fibers", Chemical Fibers International, vol. 50, No. 1, Feb. 1, 2000 (Feb. 1, 2000), p. 38/39, XP000908694, ISSN: 0340-3343.
Written Opinion of the International Preliminary Examining Authority for PCT/US2020/022148 dated Oct. 13, 2020.
Written Opinion of the International Preliminary Examining Authority for PCT/US2020/043271 dated Feb. 11, 2021.
International Search Report and Written Opinion for PCT/US2020/056300 dated Feb. 16, 2021.
International Search Report and Written Opinion for PCT/US2020/055543 dated Feb. 5, 2021.
International Search Report and Written Opinion for PCT/US2020/043273 dated Oct. 8, 2020.
International Search Report and Written Opinion for PCT/US2020/043271 dated Oct. 30, 2020.
International Search Report and Written Opinion for PCT/2020/044626 dated Oct. 30, 2020.
International Search Report and Written Opinion for PCT/US2020/044624 dated Oct. 30, 2020.
International Search Report and Written Opinion for PCT/US2020/044628 dated Oct. 30, 2020.
International Search Report and Written Opinion for PCT/US2020/022109 dated Jul. 13, 2020.
Written Opinion of the International Preliminary Examining Authority for PCT/US2020/022129 dated Nov. 13, 2020.
Written Opinion of the International Preliminary Examining Authority for PCTUS2020022109 dated Dec. 16, 2020.
Written Opinion of the International Preliminary Examining Report for PCTUS2018053529 dated Aug. 6, 2019.

International Preliminary Report on Patentability for PCTUS2014015275 dated Mar. 23, 2015.
International Preliminary Report on Patentability for PCT/US2018/053521 dated Sep. 3, 2019.
Masanori Iwata et al., Bio-Inspired Bright Structurally Colored Colloidal Amorphous Array Enhanced by Controlling Thickness and Black Background, Advanced Materials, Feb. 21, 2017, 1-8, 1605050, Germany.
International Search Report and Written Opinion for PCT/US2018/053478 dated Jun. 4, 2019.
International Search Report and Written Opinion for PCT/US2018/053516 dated May 31, 2019.
International Search Report and Written Opinion for PCT/US2018/053502 dated May 28, 2019.
International Search Report and Written Opinion for PCT/US2018/053488 dated Jun. 4, 2019.
International Search Report and Written Opinion for PCT/US2018/053529 dated Jan. 28, 2019.
International Preliminary Report on Patentability for PCT/US2018/053529 dated Dec. 18, 2019.
International Search Report and Written Opinion for PCT/US2018/053521 dated Jun. 3, 2019.
International Search Report and Written Opinion for PCT/US2018/053467 dated Jun. 3, 2019.
International Preliminary Report on Patentability for PCT/US2018/053467 dated Dec. 17, 2019.
International Search Report and Written Opinion for PCT/US2018/053510 dated May 29, 2019.
International Preliminary Report on Patentability for PCT/US2018/053510 dated Dec. 20, 2019.
International Preliminary Report on Patentability for PCT/US2018/053478 dated Mar. 31, 2020.
International Preliminary Report on Patentability for PCT/US2018/053516 dated Mar. 31, 2020.
International Search Report for PCT/US2018/053502 dated Mar. 31, 2020.
TOPAS: Cycloolefin Copolymer (COC) Brochure. TOPAS Advanced Polymers. Retrieved online Jan. 11, 2021 from https://topas.com/sites/default/files/files/topas_product-brochure_english.pdf. Published 2008. (Year: 2008).
Written Opinion of the International Preliminary Examining Authority for PCTUS2020055543 dated May 12, 2021.
International Search Report and Written Opinion for PCT/US2021/034781 dated Sep. 24, 2021.
International Search Report and Written Opinion for PCT/US2021/034865 dated Oct. 5, 2021.
International Search Report and Written Opinion for PCT/US2021/034872 dated Oct. 5, 2021.
International Search Report and Written Opinion for PCT/US2021/034921 dated Oct. 7, 2021.
CreatexColorsCo: "How To Paint a Candy Fade" YouTube, Mar. 7, 2020 (Mar. 7, 2020), XP054982299, Retrieved from the Internet: URL:https://www.youtube.com/watch?v=q3UyGEkxEHk&ab channel=CreatexColorsCo [retrieved on Sep. 6, 2021].
International Search Report and Written Opinion for PCT/US2021/034776 dated Nov. 17, 2021.
International Preliminary Report on Patentability for PCT/US2020/043271 dated Nov. 8, 2021.
Dwyer, Ross, "Stranger Things x Nike "Upside Down" Collection Release Date", SneakerNews.com Available Online at: https://sneakernews.com/2019/08/12/stranger-things-nike-upside-down-collection-release-date/, Aug. 12, 2019, 5 pages.
International Search Report and Written Opinion received for PCT Patent Application No. PCT/US2014/015275, dated Jun. 25, 2014, 11 pages.
Nike's New Air Force 1 "Reveal" Comes With DIY Tear-Away Uppers, hypebeast.com, Available online at: https://hypebeast.com/2021/2/nike-air-force-1-low-reveal-fauna-brown-arctic-punch-pale-vanilla-dj9941-244-info, Feb. 8, 2021, 10 pages.
Northman, Tora, "Nike's Latest Air Force 1 Reveals Hidden Colors", hypebae.com, Available online at: https://hypebae.com/2020/4/nike-air-force-1-reveal-diy-peel-sneakers-hidden-colors, Apr. 25, 2020, 9 pages.

(56) References Cited

OTHER PUBLICATIONS

Ruiz, Derick, "The Nike Air Force 1 "Reveal" Drops This Week", www.modern-notoriety.com, Available online at https://www.modern-notoriety.com/nike-wmns-air-force-1-air-max-98-lx-tear-away-release-date/, May 23, 2020, 20 pages.
The 'Stranger Things' x Nike "Upside Down" Pack, hypebeast.com, Available online at: https://hypebeast.com/2019/8/stranger-things-nike-upside-down-pack-tailwind-cortez-mid-blazer-sail-deep-royal-blue-release-info, Aug. 7, 2019, 12 pages.
Written Opinion of the International Preliminary Examining Authority received for PCT Patent Application No. PCT/US2020/055543, dated May 12, 2021, 7 pages.
Written Opinion for PCT/US2021/034872, dated Dec. 9, 2021.
Written Opinion of the International Preliminary Examining Authority for PCT/US2021/034865 dated Dec. 23, 2021.
International Search Report and Written Opinion for PCT/US2021/034876, dated Jan. 3, 2022.
International Search Report and Written Opinion for PCT/US2021/034880, dated Jan. 3, 2022.
International Search Report and Written Opinion for PCT/US2021/034888, dated Jan. 4, 2022.
International Search Report and Written Opinion for PCT/US2021/034891, dated Jan. 3, 2022.
International Search Report and Written Opinion for PCT/US2021/034897, dated Jan. 3, 2022.
International Search Report and Written Opinion for PCT application No. PCT/US2021/044890, dated Nov. 12, 2021.
International Search Report and Written Opinion for PCT application No. PCT/US2021/044891, dated Nov. 11, 2021.
International Search Report and Written Opinion received for PCT Patent Application No. PCT/US2021/044893, dated Nov. 16, 2021.
International Search Report and Written Opinion received for PCT Patent Application No. PCT/US2021/044894, dated Nov. 11, 2021.
International Preliminary Report on Patentability for PCT/US2020/0553543, dated Jan. 25, 2022.
Written Opinion of the International Preliminary Examining Authority for PCT/US/2021/034781, dated Feb. 16, 2022.
International Preliminary Report on Patentability for PCT/US2020/056300, dated Feb. 17, 2022.
Written Opinion of the International Preliminary Examining Authority for PCT/US2021/034776, dated Mar. 29, 2022.
Written Opinion of the International Preliminary Examining Authority for PCT/US2021/0348766, dated Mar. 25, 2022.
Written Opinion of the International Preliminary Examining Authority for PCT/US2021/034897, dated Mar. 29, 2022.
International Search Report and Written Opinion for PCT/US2021/072456, dated Mar. 17, 2022.
Written Opinion of the International Preliminary Examining Authority for PCT/US2021/034876, dated Mar. 25, 2022.
U.S. Pat. No. 10,555,580 A1, dated Feb. 11, 2020, Peyon Lee D.
Written Opinion of the International Preliminary Examining Authority for PCT/US2021/034880, dated Apr. 7, 2022.
Written Opinion of the International Preliminary Examining Authority for PCT/US2021/034888, dated Apr. 7, 2022.
Written Opinion of the International Preliminary Examining Authority for PCT/US2021/034891, dated Apr. 7, 2022.

STRUCTURALLY-COLORED ARTICLES AND METHODS FOR MAKING AND USING STRUCTURALLY-COLORED ARTICLES

CROSS-REFERENCE TO RELATED APPLICATIONS

This application is a divisional of copending U.S. application Ser. No. 16/146,614, having the title "STRUCTURALLY COLORED ARTICLES AND METHODS OF MAKING STRUCTURALLY COLORED ARTICLES", filed on Sep. 28, 2018, which application claims the benefit of and priority to U.S. Provisional Application Ser. No. 62/565,299, having the title "STRUCTURALLY COLORED ARTICLES AND METHODS OF MAKING STRUCTURALLY COLORED ARTICLES", filed on Sep. 29, 2017, and to U.S. Provisional Application Ser. No. 62/633,666, having the title "ARTICLES HAVING STRUCTURAL COLOR AND METHODS AND SYSTEMS FOR MAKING ARTICLES HAVING STRUCTURAL COLOR", filed on Feb. 22, 2018, and to U.S. Provisional Application Ser. No. 62/565,306, having the title "STRUCTURALLY COLORED STRUCTURES AND ARTICLES, METHODS OF MAKING STRUCTURES AND ARTICLES", filed on Sep. 29, 2017, and to U.S. Provisional Application Ser. No. 62/565,313, having the title "STRUCTURES HAVING STRUCTURAL COLOR AND METHODS AND SYSTEMS FOR MAKING STRUCTURES HAVING STRUCTURAL COLOR", filed on Sep. 29, 2017, and U.S. Provisional Application Ser. No. 62/565,310, having the title "STRUCTURES HAVING STRUCTURAL COLOR AND METHODS AND SYSTEMS FOR MAKING STRUCTURES HAVING STRUCTURAL COLOR", filed on Sep. 29, 2017, the disclosures which are incorporated herein by reference in their entireties.

BACKGROUND

Structural color is caused by the physical interaction of light with the micro- or nano-features of a surface and the bulk material as compared to color derived from the presence of dyes or pigments that absorb or reflect specific wavelengths of light based on the chemical properties of the dyes or pigments. Color from dyes and pigments can be problematic in a number of ways. For example, dyes and pigments and their associated chemistries for fabrication and incorporation into finished goods may not be environmentally friendly.

BRIEF DESCRIPTION OF THE DRAWINGS

Further aspects of the present disclosure will be more readily appreciated upon review of the detailed description of its various embodiments, described below, when taken in conjunction with the accompanying drawings.

DESCRIPTION

Figure 1:
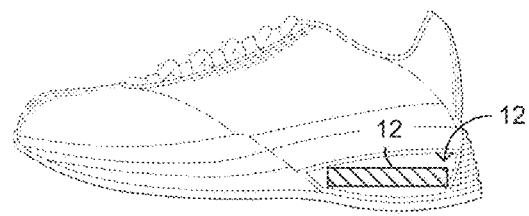
FIG. 1 illustrates an article of footwear that includes the multi-layer optical films of the present disclosure.

The present disclosure provides for a bladder that is structurally colored. The bladder includes a multi-layer optical film disposed on a surface of the bladder. The multi-layer optical film as disposed on the bladder has the characteristic of imparting a structural color (e.g., a single-hue structural color, a multi-hue structural color, an iridescent structural color, etc.). The structural color imparts an aesthetically appealing color to the bladder without requiring the use of dyes or pigments and the environmental issues associated with their use. In one embodiment, the bladder can be used in articles of footwear, components of footwear, articles of apparel, components of apparel, articles of sports equipment, components of sports equipment, and the like. Additionally, the bladder can be used in other types of consumer goods.

The multi-layer optical film alone or optionally in combination with a textured surface (e.g., a textured layer or textured surface), or optionally in combination with a primer layer, or optionally in combination with both a textured surface and a primer layer, can impart the structural color. The optional textured surface and/or the primer layer can be part of the multi-layer optical film or can be separate from the multi-layer optical film, but, when used with the multi-layer optical film, combine to impart the structural color. In other words, while the multi-layer optical film alone can impart a first structural color, the combination of the multi-layer optical film with the optional textured structure or primer layer or both can impart a second structural color, which differs from the first structural color multi-layer optical film based on a color parameter such as hue, lightness, iridescence type. In such cases, the combination of the multi-layer optical film and the textured surface and/or the primer layer can impart the structural color to the bladder.

After disposing the multi-layer optical film onto a side or surface of a bladder wall or another component of the bladder, the bladder (e.g., bladder wall) appears to be colored (i.e., to have a new, different color than the surface of the bladder wall or component had prior to the disposition) without the application of pigments or dyes to the bladder, although dyes and/or pigments can be used in conjunction with the structural color. The multi-layer optical film can be disposed (e.g., affixed, attached, adhered, bonded, joined) to an exterior-facing side of the bladder, or an interior-facing side of the bladder. The bladder can then be incorporated into an article, such as a sole or an upper for an article of footwear, for example. The article (e.g., the sole and/or upper) can be designed so that one or more portions of the bladder including the structurally colored bladder wall or component is visible in the finished article, by including an opening, or a transparent component covering the structurally colored component, and the like.

The present disclosure provides for an article comprising: a bladder having a first bladder wall having a first bladder wall thickness and an exterior-facing side comprising a first thermoplastic material and an interior-facing side comprising a second thermoplastic material, wherein the first bladder wall has a gas transmission rate of 15 cm$^3$/m$^2$·atm·day or less for nitrogen for an average wall thickness of 20 mils; and an multi-layer optical film has a first side and a second side, wherein the first side and the second side are on opposing sides, wherein the first side of the multi-layer optical film, the second side of the multi-layer optical film, or both result in a structural color, wherein the multi-layer optical film is disposed on the exterior-facing side surface or the interior-facing side surface of the bladder or wherein the multi-layer optical film is disposed in an internal cavity of the bladder. The multi-layer optical film can include an optical layer. A textured surface and/or a primer layer in combination with the optical layer can result in the structural color. The present disclosure also provides for an article of footwear or an article of sporting equipment, comprising cushioning element, wherein the cushioning element includes a bladder. The present disclosure also provides for methods of making such an article.

The present disclosure also provides for an inflated bladder comprising a bladder wall having an interior-facing side and an exterior-facing side, wherein the interior-facing side defines at least a portion of an interior region of the inflated bladder, and wherein the bladder wall further includes an average wall thickness between the interior-facing side and exterior-facing side that is less than 5 millimeters; and a multi-layer optical film having a first side and a second opposing side, wherein the first side of the multi-layer optical film is operably disposed on the exterior-facing side of the bladder wall, and wherein the multi-layer optical film imparts a structural color to the bladder wall. The present disclosure also provides for methods of making such an article. The present disclosure also provides for a bladder comprising a bladder wall having an interior-facing side and an exterior-facing side, wherein the interior-facing side defines at least a portion of an interior region of the bladder; a plurality of topographical structures extending from the exterior-facing side of the bladder wall; and a multi-layer optical film having a first side and a second opposing side, wherein the first side of the multi-layer optical film is disposed on the exterior-facing side of the bladder wall and covering the plurality of topographical structures, and wherein the multi-layer optical film imparts a structural color to the bladder wall. The present disclosure also provides for methods of making such an article.

The present disclosure also provides for an article of footwear comprising a footwear upper; and an inflated bladder comprising a top wall operably secured to the footwear upper; a bottom wall opposite the top wall; and one or more sidewalls extending between the top wall and the bottom wall of the inflated bladder, wherein the top wall, the bottom wall, and the one or more sidewalls collectively define an interior region of the inflated bladder, and wherein the one or more sidewalls each comprise an exterior-facing side; and a multi-layer optical film operably disposed on the exterior-facing side at least one of the one or more sidewalls to impart a structural color to the one or more sidewalls. The present disclosure also provides for methods of making such an article.

In particular examples, a primer layer or a textured surface or both is included in the multi-layer optical film, or on the bladder. While many possible materials can be used to form the primer layer, it has been found that using titanium dioxide in the primer material of the primer layer, or using a primer material consisting essentially of titanium dioxide, results in a primer layer which adheres well to flexible polymeric materials including polyurethanes.

While in many examples of this disclosure, an iridescent structural color (i.e., a color which shifts over a wide range of hues when viewed from different angles) can be obtained, in other examples a structural color which does not shift over a wide range of hues when viewed from different angles (e.g., a structural color which does not shift hues, or which shifts over a limited number of hues) also can be obtained.

In one example, the present disclosure provides for the multi-layer optical film, as disposed onto the bladder, when measured according to the CIE 1976 color space under a given illumination condition at three observation angles between −15 degrees and +60 degrees, has a first color measurement at a first angle of observation having coordinates $L_1^*$ and $a_1^*$ and $b_1^*$, and a second color measurement at a second angle of observation having coordinates $L_2^*$ and $a_2^*$ and $b_2^*$, and a third color measurement at a third angle of observation having coordinates $L_3^*$ and $a_3^*$ and $b_3^*$, wherein the $L_1^*$, $L_2^*$, and $L_3^*$ values may be the same or different, wherein the $a_1^*$, $a_2^*$, and $a_3^*$ coordinate values may be the same or different, wherein the $b_1^*$, $b_2^*$, and $b_3^*$ coordinate values may be the same or different, and wherein the range of the combined $a_1^*$, $a_2^*$ and $a_3^*$ values is less than about 40% of the overall scale of possible a* values.

In another example, the present disclosure provides for the multi-layer optical film, as disposed onto the bladder, when measured according to the CIE 1976 color space under a given illumination condition at two observation angles between −15 degrees and +60 degrees, has a first color measurement at a first angle of observation having coordinates $L_1^*$ and $a_1^*$ and $b_1^*$, and a second color measurement at a second angle of observation having coordinates $L_2^*$ and $a_2^*$ and $b_2^*$, wherein the $L_1^*$ and $L_2^*$ values may be the same or different, wherein the $a_1^*$ and $a_2^*$ coordinate values may be the same or different, wherein the $b_1^*$ and $b_2^*$ coordinate values may be the same or different, and wherein the $\Delta E^*_{ab}$ between the first color measurement and the second color measurement is less than or equal to about 100, where $\Delta E^*_{ab}=[(L_1^*-L_2^*)^2+(a_1^*-a_2^*)^2+(b_1^*-b_2^*)^2]^{1/2}$.

In yet another example, the present disclosure provides for the multi-layer optical film, as disposed onto the bladder, when measured according to the CIELCH color space under a given illumination condition at three observation angles between −15 degrees and +60 degrees, has a first color measurement at a first angle of observation having coordinates $L_1^*$ and $C_1^*$ and $h_1°$, and a second color measurement at a second angle of observation having coordinates $L_2^*$ and $C_2^*$ and $h_2°$, and a third color measurement at a third angle of observation having coordinates $L_3$ and $C_3^*$ and $h_3°$, wherein the $L_1^*$, $L_2^*$, and $L_3$ values may be the same or different, wherein the $C_1^*$, $C_2^*$, and $C_3^*$ coordinate values may be the same or different, wherein the $h_1°$, $h_2°$ and $h_3°$ coordinate values may be the same or different, and wherein the range of the combined $h_1°$, $h_2°$ and $h_3°$ values is less than about 60 degrees.

In an embodiment, the present disclosure provides for a method of making an article of footwear comprising: providing a bladder as described above and herein; and incorporating the bladder onto a sole structure. In addition, the method includes affixing the sole structure to an upper structure to form the article of footwear.

The present disclosure provides for a method of making a bladder, comprising: disposing a multi-layer optical film on a surface of a bladder. The bladder can be a bladder having a first bladder wall having a first bladder wall thickness and an exterior-facing side comprising a first thermoplastic material and an interior-facing side comprising a second thermoplastic material. Optionally, the first bladder wall has a gas transmission rate of 15 cm$^3$/m$^2$·atm·day or less for nitrogen for an average wall thickness of 20 mils; and disposing a multi-layer optical film onto at least one region of the bladder. The multi-layer optical film has a first side and a second side, wherein the first side and the second side are on opposing sides, wherein the first side of the multi-layer optical film, the second side of the multi-layer optical film, or both impart a structural color. The multi-layer optical film can be disposed on the exterior-facing side surface or the interior-facing side surface of the bladder, or can be disposed in an internal cavity of the bladder. The present disclosure also provides for a bladder formed using the method described above and herein.

Now having described embodiments of the present disclosure generally, additional discussion regarding embodiments will be described in greater details.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of material science, chemistry, textiles, polymer chemistry, and the like, which are within the skill of the art. Such techniques are explained fully in the literature.

Unless otherwise defined, all technical and scientific terms used herein have the same meaning as commonly understood by one of ordinary skill in the art of material science, chemistry, textiles, polymer chemistry, and the like. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The present disclosure provides for bladder that have structural color. The structural color can be produced using a multi-layer optical film incorporated with the bladder. The multi-layer optical film can be incorporated into bladder, for example, on an exterior-facing side or surface or an interior-facing side or surface of the bladder. The bladder can be incorporated into a sole structure that can be affixed to the upper optionally with other components to form the article of footwear. The sole structure and/or upper can be designed so that one or more portions including the structural color are not covered up, include an opening, or otherwise exposed so that the structural color is visible in the finished article of footwear and provides an aesthetically pleasing appearance.

In an aspect, the bladder can be incorporated into a number of different types of articles of manufacture such as articles of footwear, components of footwear, articles of apparel, components of apparel, articles of sporting equipment, and components of sporting equipment. For example, the bladder can be used as a cushioning element once inflated (e.g., fluid-filled bladder). In particular, the articles of manufacture can include footwear (e.g., dress shoes, athletic footwear, hiking boots, work boots, or the like), skates (e.g., hockey skates, figure skates, in-line skates, roller skates, or the like), apparel (e.g., shirts, jerseys, pants, shorts, gloves, glasses, socks, hats, caps, jackets, undergarments) or components thereof, containers (e.g., backpacks, bags), and upholstery for furniture (e.g., chairs, couches, car seats), bed coverings (e.g., sheets, blankets), table coverings, towels, flags, tents, sails, and parachutes. In addition, the bladder can be used to produce articles or other items that are disposed on the article, where the article can be striking devices (e.g., bats, rackets, sticks, mallets, golf clubs, paddles, etc.), athletic equipment (e.g., golf bags, baseball and football gloves, soccer ball restriction structures), protective equipment (e.g., pads, helmets, guards, visors, masks, goggles, etc.), locomotive equipment (e.g., bicycles, motorcycles, skateboards, cars, trucks, boats, surfboards, skis, snowboards, etc.), balls or pucks for use in various sports, fishing or hunting equipment, furniture, electronic equipment, construction materials, eyewear, timepieces, jewelry, and the like. In an aspect, the bladder can be used as a cushioning element in the strap of a backpack or other bag.

The footwear can be designed for a variety of uses, such as sporting, athletic, military, work-related, recreational, or casual use. Primarily, the article of footwear is intended for outdoor use on unpaved surfaces (in part or in whole), such as on a ground surface including one or more of grass, turf, gravel, sand, dirt, clay, mud, and the like, whether as an athletic performance surface or as a general outdoor surface. However, the article of footwear may also be desirable for indoor applications, such as indoor sports including dirt playing surfaces for example (e.g., indoor baseball fields with dirt infields).

The article of footwear is designed for use in outdoor sporting activities, such as global football/soccer, golf, American football, rugby, baseball, running, track and field, cycling (e.g., road cycling and mountain biking), and the like. The article of footwear can optionally include traction elements (e.g., lugs, cleats, studs, and spikes as well as tread patterns) to provide traction on soft and slippery surfaces, where components of the present disclosure can be used or applied between or among the traction elements and optionally on the sides of the traction elements but on the surface of the traction element that contacts the ground or surface. Cleats, studs and spikes are commonly included in footwear designed for use in sports such as global football/soccer, golf, American football, rugby, baseball, and the like, which are frequently played on unpaved surfaces. Lugs and/or exaggerated tread patterns are commonly included in footwear including boots design for use under rugged outdoor conditions, such as trail running, hiking, and military use.

When the bladder is incorporated into footwear, the bladder can be incorporated into a sole structure that can be affixed to an upper as well as other components to form the footwear. In an aspect, the sole and/or upper can be designed so that one or more portions of the bladder are not covered up, include an opening, or otherwise exposed so that the structural color can be observed.

FIG. 1 illustrates an article of footwear having a bladder 11 that includes the multi-layer optical film of the present disclosure. The multi-layer optical film is represented by hashed area 12. The location of the multi-layer optical film is provided only to indicate one possible area that the multi-layer optical film can be located. Also, one location is illustrated in the figure, but this is done only for illustration purposes as the bladder can include one or a plurality of multi-layer optical films, where the size and location can be determined based on the item. The multi-layer optical film(s) located can represent a number, letter, symbol, design, emblem, graphic mark, icon, logo, or the like.

Figure 2:
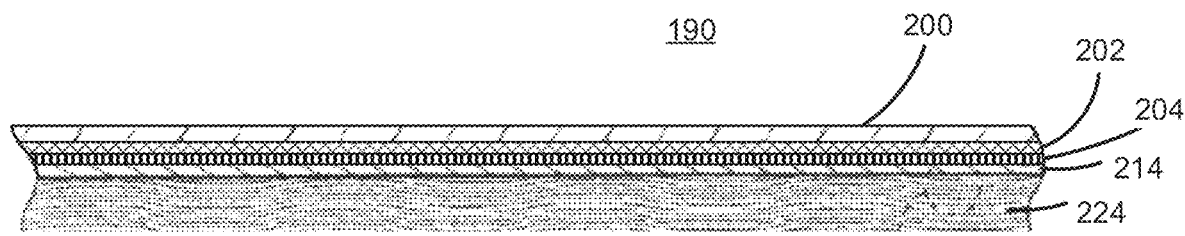
FIG. 2 illustrates a side view of a portion of a bladder having an exemplary multi-layer optical film of the present disclosure.

FIG. 2 illustrates a cross-section of the bladder that illustrate one possible location of the multi-layer optical film on a first bladder wall. As shown in FIG. 2, the first bladder wall 190 has a core layer 224 having a plurality of layers, optionally a cap layer 214, optionally a primer layer 204, optionally a textured structure or a textured layer 202, and an multi-layer optical film 200. Optionally, the position of the primer layer and the textured structure or textured layer can be reversed (not shown). Optionally, the cap layer can be formed of the first thermoplastic material, and can include a textured surface (not shown). Alternatively or additionally, the side of the multi-layer optical film 200 facing the cap layer 214 can include a primer layer, or a textured surface, or both.

Bladders of the present disclosure include the multi-layer optical film that has the characteristic of producing optical effects such as structural color. The multi-layer optical film includes at least one optical layer (e.g., a multilayer reflector or a multilayer filter) optionally in combination with a textured surface (e.g., integral to the multi-layer optical film or as part of the surface of the bladder), optionally with a primer layer, optionally with a protective layer, or optionally with any combination of the textured surface, the primer layer, and the protective layer. The multi-layer optical film or the combination of the multi-layer optical film optionally with the textured surface and/or primer layer impart structural color (e.g., single color, multicolor, iridescent), to the bladder. Following disposing of the multi-layer optical film on the bladder, the bladder appears to be colored, for example a new, different, or more intense color (e.g., in hue or otherwise defined herein) than the surface of the article had prior to the disposing, and this can be achieved with or without the application of pigments or dyes to the bladder to produce aesthetically pleasing effects.

As has been described herein, the structural color can include one of a number of colors. The "color" of an bladder as perceived by a viewer can differ from the actual color of the bladder, as the color perceived by a viewer is determined by the actual color of the bladder, by the viewer's ability to detect the wavelengths of light reflected by the bladder, by the wavelengths of light used to illuminate the bladder, as well as other factors such as the coloration of the environment of the bladder, and the type of incident light (e.g., sunlight, fluorescent light, and the like). As a result, the color of an object as perceived by a viewer can differ from the actual color of the bladder.

Conventionally, color is imparted to man-made objects by applying colored pigments or dyes to the object. More recently, methods of imparting "structural color" to man-made objects have been developed. Structural color is color which is produced, at least in part, by microscopically structured surfaces that interfere with visible light contacting the surface.

The structural color is color caused by physical phenomena including the scattering, refraction, reflection, interference, and/or diffraction of light, unlike color caused by the absorption or emission of visible light through coloring matters. For example, optical phenomena which result in structural color can include multilayer interference, thin-film interference, refraction, dispersion, light scattering, Mie scattering, diffraction, and diffraction grating. In various aspects described herein, structural color imparted to an article can be visible to a viewer having 20/20 visual acuity and normal color vision from a distance of about 1 meter from the article.

The structural color can be angle-independent structural color in that the hue, the hue and value, or the hue, value and chroma observed is independent of or substantially (e.g., about 90 percent, about 95 percent, or about 99 percent) independent of the angle of observation. For example, the angle-independent structural color can display the same hue or substantially the same hue when viewed from at least 3 different angles that are at least 15 degrees apart from each other (e.g., single-hue structural color).

As described herein, structural color is produced, at least in part, by the multi-layer optical film, as opposed to the color being produced solely by pigments and/or dyes. The coloration of a structurally-colored bladder can be due solely to structural color (i.e., the bladder, a colored portion of the bladder, or a colored outer layer of the bladder can be substantially free of pigments and/or dyes). Structural color can also be used in combination with pigments and/or dyes, for example, to alter all or a portion of a structural color.

"Hue" is commonly used to describe the property of color which is discernible based on a dominant wavelength of visible light, and is often described using terms such as magenta, red, orange, yellow, green, cyan, blue, indigo, violet, etc. or can be described in relation (e.g., as similar or dissimilar) to one of these. The hue of a color is generally considered to be independent of the intensity or lightness of the color. For example, in the Munsell color system, the properties of color include hue, value (lightness) and chroma (color purity). Particular hues are commonly associated with particular ranges of wavelengths in the visible spectrum: wavelengths in the range of about 700 to 635 nanometers are associated with red, the range of about 635 to 590 nanometers is associated with orange, the range of about 590 to 560 nanometers is associated with yellow, the range of about 560 to 520 nanometers is associated with green, the range of about 520 to 490 nanometers is associated with cyan, the range of about 490 nanometers to 450 nanometers is associated with blue, and the range of about 450 to 400 nanometers is associated with violet.

The color (including the hue) of a bladder as perceived by a viewer can differ from the actual color of the bladder. The color as perceived by a viewer depends not only on the physics of the bladder, but also its environment, and the characteristics of the perceiving eye and brain. For example, as the color perceived by a viewer is determined by the actual color of the bladder (e.g., the color of the light leaving the surface of the bladder), by the viewer's ability to detect the wavelengths of light reflected or emitted by the bladder, by the wavelengths of light used to illuminate the bladder, as well as other factors such as the coloration of the environment of the bladder, and the type of incident light (e.g., sunlight, fluorescent light, and the like). As a result, the color of an object as perceived by a viewer can differ from the actual color of the bladder.

When used in the context of structural color, one can characterize the hue of a structurally-colored article (bladder), i.e., an article (e.g., bladder) that has been structurally colored by incorporating an optical element into the article, based on the wavelengths of light the structurally-colored portion of the article absorbs and reflects (e.g., linearly and non-linearly). While the optical element may impart a first structural color, the presence of an optional textured surface and/or primer layer can alter the structural color. Other factors such as coatings or transparent elements may further alter the perceived structural color. The hue of the structurally colored article can include any of the hues described herein as well as any other hues or combination of hues. The structural color can be referred to as a "single hue" (i.e., the hue remains substantially the same, regardless of the angle of observation and/or illumination), or "multihued" (i.e., the hue varies depending upon the angle of observation and/or illumination). The multihued structural color can be iridescent (i.e., the hue changes gradually over two or more hues as the angle of observation or illumination changes). The hue of an iridescent multihued structural color can change gradually across all the hues in the visible spectrum (e.g., like a "rainbow") as the angle of observation or illumination changes. The hue of an iridescent multihued structural color can change gradually across a limited number of hues in the visible spectrum as the angle of observation or illumination changes, in other words, one or more hues in the visible spectrum (e.g., red, orange, yellow, etc.) are not observed in the structural color as the angle of observation or illumination changes. Only one hue, or substantially one hue, in the visible spectrum may be present for a single-hued structural color. The hue of a multihued structural color can change more abruptly between a limited number of hues (e.g., between 2-8 hues, or between 2-4 hues, or between 2 hues) as the angle of observation or illumination changes.

The structural color can be a multi-hued structural color in which two or more hues are imparted by the structural color.

The structural color can be iridescent multi-hued structural color in which the hue of the structural color varies over a wide number of hues (e.g., 4, 5, 6, 7, 8 or more hues) when viewed at a single viewing angle, or when viewed from two or more different viewing angles that are at least 15 degrees apart from each other.

The structural color can be limited iridescent multi-hue structural color in which the hue of the structural color varies, or varies substantially (e.g., about 90 percent, about 95 percent, or about 99 percent) over a limited number of hues (e.g., 2 hues, or 3 hues) when viewed from two or more different viewing angles that are at least 15 degrees apart from each other. In some aspects, a structural color having limited iridescence is limited to two, three or four hues selected from the RYB primary colors of red, yellow and blue, optionally the RYB primary and secondary colors of red, yellow, blue, green, orange and purple, or optionally the RYB primary, secondary and tertiary colors of red, yellow, blue, green, orange purple, green-yellow, yellow-orange, orange-red, red-purple, purple-blue, and blue-green.

The structural color can be single-hue angle-independent structural color in which the hue, the hue and value, or the hue, value and chroma of the structural color is independent of or substantially (e.g., about 90 percent, about 95 percent, or about 99 percent) independent of the angle of observation. For example, the single-hue angle-independent structural color can display the same hue or substantially the same hue when viewed from at least 3 different angles that are at least 15 degrees apart from each other (e.g., single-hue structural color).

The structural color imparted can be a structural color having limited iridescence such that, when each color observed at each possible angle of observation is assigned to a single hue selected from the group consisting of the primary, secondary and tertiary colors on the red yellow blue (RYB) color wheel, for a single structural color, all of the assigned hues fall into a single hue group, wherein the single hue group is one of a) green-yellow, yellow, and yellow-orange; b) yellow, yellow-orange and orange; c) yellow-orange, orange, and orange-red; d) orange-red, and red-purple; e) red, red-purple, and purple; f) red-purple, purple, and purple-blue; g) purple, purple-blue, and blue; h) purple-blue, blue, and blue-green; i) blue, blue-green and green; and j) blue-green, green, and green-yellow. In other words, in this example of limited iridescence, the hue (or the hue and the value, or the hue, value and chroma) imparted by the structural color varies depending upon the angle at which the structural color is observed, but the hues of each of the different colors viewed at the various angles of observations varies over a limited number of possible hues. The hue visible at each angle of observation can be assigned to a single primary, secondary or tertiary hue on the red yellow blue (RYB) color wheel (i.e., the group of hues consisting of red, yellow, blue, green, orange purple, green-yellow, yellow-orange, orange-red, red-purple, purple-blue, and blue-green). For example, while a plurality of different colors are observed as the angle of observation is shifted, when each observed hue is classified as one of red, yellow, blue, green, orange purple, green-yellow, yellow-orange, orange-red, red-purple, purple-blue, and blue-green, the list of assigned hues includes no more than one, two, or three hues selected from the list of RYB primary, secondary and tertiary hues. In some examples of limited iridescence, all of the assigned hues fall into a single hue group selected from hue groups a)-j), each of which include three adjacent hues on the RYB primary, secondary and tertiary color wheel. For example, all of the assigned hues can be a single hue within hue group h) (e.g., blue), or some of the assigned hues can represent two hues in hue group h) (e.g., purple-blue and blue), or can represent three hues in hue group h) (e.g., purple-blue, blue, and blue-green).

Similarly, other properties of the structural color, such as the lightness of the color, the saturation of the color, and the purity of the color, among others, can be substantially the same regardless of the angle of observation or illumination, or can vary depending upon the angle of observation or illumination. The structural color can have a matte appearance, a glossy appearance, or a metallic appearance, or a combination thereof.

As discussed above, the color (including hue) of a structurally-colored bladder can vary depending upon the angle at which the structurally-colored bladder is observed or illuminated. The hue or hues of a bladder can be determined by observing the bladder, or illuminating the bladder, at a variety of angles using constant lighting conditions. As used herein, the "angle" of illumination or viewing is the angle measured from an axis or plane that is orthogonal to the surface. The viewing or illuminating angles can be set between about 0 and 180 degrees. The viewing or illuminating angles can be set at 0 degrees, 15 degrees, 30 degrees, 45 degrees, 60 degrees, and −15 degrees and the color can be measured using a colorimeter or spectrophotometer (e.g., Konica Minolta), which focuses on a particular area of the bladder to measure the color. The viewing or illuminating angles can be set at 0 degrees, 15 degrees, 30 degrees, 45 degrees, 60 degrees, 75 degrees, 90 degrees, 105 degrees, 120 degrees, 135 degrees, 150 degrees, 165 degrees, 180 degrees, 195 degrees, 210 degrees, 225 degrees, 240 degrees, 255 degrees, 270 degrees, 285 degrees, 300 degrees, 315 degrees, 330 degrees, and 345 degrees and the color can be measured using a colorimeter or spectrophotometer. In a particular example of a multihued bladder colored using only structural color, when measured at 0 degrees, 15 degrees, 30 degrees, 45 degrees, 60 degrees, and −15 degrees, the hues measured for bladder consisted of "blue" at three of the measurement angles, "blue-green" at 2 of the measurement angles and "purple" at one of the measurement angles.

In other embodiments, the color (including hue, value and/or chroma) of a structurally-colored bladder does not change substantially, if at all, depending upon the angle at which the bladder is observed or illuminated. In instances such as this the structural color can be an angle-independent structural color in that the hue, the hue and value, or the hue, value and chroma observed is substantially independent or is independent of the angle of observation.

Various methodologies for defining color coordinate systems exist. One example is L*a*b* color space, where, for a given illumination condition, L* is a value for lightness, and a* and b* are values for color-opponent dimensions based on the CIE coordinates (CIE 1976 color space or CIELAB). In an embodiment, a structurally-colored bladder having structural color can be considered as having a "single" color when the change in color measured for the bladder is within about 10% or within about 5% of the total scale of the a* or b* coordinate of the L*a*b* scale (CIE 1976 color space) at three or more measured observation or illumination angles selected from measured at observation or illumination angles of 0 degrees, 15 degrees, 30 degrees, 45 degrees, 60 degrees, and −15 degrees. In certain embodiments, colors which, when measured and assigned values in the L*a*b* system that differ by at least 5 percent of the scale of the a* and b* coordinates, or by at least 10 percent of the scale of the a* and b* coordinates, are considered to be different colors. The structurally-colored bladder can have a change of less than about 40%, or less than about 30%, or less than about 20%, or less than about 10%, of the total scale of the a* coordinate or b* coordinate of the L*a*b* scale (CIE 1976 color space) at three or more measured observation or illumination angles.

A change in color between two measurements in the CIELAB space can be determined mathematically. For example, a first measurement has coordinates $L_1^*$, $a_1^*$ and $b_1^*$, and a second measurement has coordinates $L_2^*$, $a_2^*$ and $b_2^*$. The total difference between these two measurements on the CIELAB scale can be expressed as $\Delta E^*_{ab}$, which is calculated as follows: $\Delta E^*_{ab} = [(L_1^* - L_2^*)^2 + (a_1^* - a_2^*)^2 + (b_1^* - b_2^*)^2]^{1/2}$. Generally speaking, if two colors have a $\Delta E^*_{ab}$ of less than or equal to 1, the difference in color is not perceptible to human eyes, and if two colors have a $\Delta E^*_{ab}$ of greater than 100 the colors are considered to be opposite colors, while a $\Delta E^*_{ab}$ of about 2-3 is considered the threshold for perceivable color difference. In certain embodiments, a structurally colored bladder having structural color can be considered as having a "single" color when the $\Delta E^*_{ab}$ is less than 60, or less than 50, or less than 40, or less than 30, between three or more measured observation or illumination angles selected from measured at observation or illumination angles of 0 degrees, 15 degrees, 30 degrees, 45 degrees, 60 degrees, and −15 degrees. The structurally-colored bladder can have a $\Delta E^*_{ab}$ that is less than about 100, or less than about 80, or less than about 60, between two or more measured observation or illumination angles.

Another example of a color scale is the CIELCH color space, where, for a given illumination condition, L* is a value for lightness, C* is a value for chroma, and h° denotes a hue as an angular measurement. In an embodiment, a structurally-colored bladder having structural color can be considered as having a "single" color when the color measured for the bladder is less than 10 degrees different or less than 5 degrees different at the h° angular coordinate of the CIELCH color space, at three or more measured observation or illumination angles selected from measured at observation or illumination angles of 0 degrees, 15 degrees, 30 degrees, 45 degrees, 60 degrees, and −15 degrees. In certain embodiments, colors which, when measured and assigned values in the CIELCH system that vary by at least 45 degrees in the h° measurements, are considered to be different colors The structurally-colored bladder can have a change of less than about 60 degrees, or less than about 50 degrees, or less than about 40 degrees, or less than about 30 degrees, or less than about 20 degrees, or less than about 10 degrees, in the h° measurements of the CIELCH system at three or more measured observation or illumination angles.

Another system for characterizing color includes the "PANTONE" Matching System (Pantone LLC, Carlstadt, N.J., USA), which provides a visual color standard system to provide an accurate method for selecting, specifying, broadcasting, and matching colors through any medium. In an example, a structurally-colored bladder having a structural color can be considered as having a "single" color when the color measured for the bladder is within a certain number of adjacent standards, e.g., within 20 adjacent PANTONE standards, at three or more measured observation or illumination angles selected from 0 degrees, 15 degrees, 30 degrees, 45 degrees, 60 degrees, and −15 degrees.

Now having described color, additional details regarding the multi-layer optical film are provided. As described herein, the article includes the multi-layer optical film. The multi-layer optical film includes at least one optical layer. The multi-layer optical film that can be or include a single or multilayer reflector or a multilayer filter. The multi-layer optical film can function to modify the light that impinges thereupon so that structural color is imparted to the article. The multi-layer optical film can include at least one optical layer and optionally one or more additional layers (e.g., a protective layer, the textured layer, the primer layer, a polymer layer, and the like).

The method of making the structurally colored article can include disposing (e.g., affixing, attaching, bonding, fastening, joining, appending, connecting, binding and includes operably disposing etc.) the multi-layer optical film onto an article (e.g., an article of footwear, an article of apparel, an article of sporting equipment, etc.). The article includes a component, and the component has a surface upon which the multi-layer optical film can be disposed. The surface of the article can be made of a material such as a thermoplastic material or thermoset material, as described herein. For example, the article has a surface including a thermoplastic material (i.e., a first thermoplastic material), for example an externally-facing surface of the component or an internally-facing surface of the component (e.g., an externally-facing surface or an internally-facing surface a bladder). The multi-layer optical film can be disposed onto the thermoplastic material, for example.

The multi-layer optical film has a first side (including the outer surface) and a second side opposing the first side (including the opposing outer surface), where the first side or the second side is adjacent the article. For example, when the multi-layer optical film is used in conjunction with a component having internally-facing and externally-facing surfaces, such as a film or a bladder, the first side of the multi-layer optical film can be disposed on the internally-facing surface of the component, such as in the following order second side of the multi-layer optical film/core of the multi-layer optical film/first side of the multi-layer optical film/internally-facing surface of the component/core of the component/externally-facing surface of the component. Alternatively, the second side the multi-layer optical film can be disposed on the internally-facing surface of the component, such as in the following order first side of the multi-layer optical film/core of the multi-layer optical film/second side of the multi-layer optical film/internally-facing surface of the component/core of the component wall/externally-facing surface of the component. In another example, the first side of the multi-layer optical film can be disposed on the externally-facing surface of the component, such as in the following order: internally-facing surface of the component/core of the component/externally-facing surface of the component/first side of the multi-layer optical film/core of the multi-layer optical film/second side of the multi-layer optical film. Similarly, the second side of the multi-layer optical film can be disposed on the externally-facing surface of the component, such as in the following order: internally-facing surface of the component/core of the component/externally-facing surface of the component/second side of the multi-layer optical film/core of the multi-layer optical film/first side of the multi-layer optical film. In examples where the optional textured surface, the optional primer layer, or both are present, the textured surface and/or the primer layer can be located at the interface between the surface of the component and a side of the multi-layer optical film.

The multi-layer optical film or layers or portions thereof (e.g., optical layer) can be formed using known techniques such as physical vapor deposition, electron beam deposition, atomic layer deposition, molecular beam epitaxy, cathodic arc deposition, pulsed laser deposition, sputtering deposition (e.g., radio frequency, direct current, reactive, non-reactive), chemical vapor deposition, plasma-enhanced chemical vapor deposition, low pressure chemical vapor deposition and wet chemistry techniques such as layer-by-layer deposition, sol-gel deposition, Langmuir blodgett, and the like. The temperature of the first side can be adjusted using the technique to form the multi-layer optical film and/or a separate system to adjust the temperature. Additional details are provided herein.

The optical layer(s) of the multi-layer optical film can comprise a multilayer reflector. The multilayer reflector can be configured to have a certain reflectivity at a given wavelength of light (or range of wavelengths) depending, at least in part, on the material selection, thickness and number of the layers of the multilayer reflector. In other words, one can carefully select the materials, thicknesses, and numbers of the layers of a multilayer reflector and optionally its interaction with one or more other layers, so that it can reflect a certain wavelength of light (or range of wavelengths), to produce a desired structural color. The optical layer can include at least two adjacent layers, where the adjacent layers have different refractive indices. The difference in the index of refraction of adjacent layers of the optical layer can be about 0.0001 to 50 percent, about 0.1 to 40 percent, about 0.1 to 30 percent, about 0.1 to 20 percent, about 0.1 to 10 percent (and other ranges there between (e.g., the ranges can be in increments of 0.0001 to 5 percent)). The index of refraction depends at least in part upon the material of the optical layer and can range from 1.3 to 2.6.

The optical layer(s) can include 2 to 20 layers, 2 to 10 layer, 2 to 6 layers, or 2 to 4 layers. Each layer of the optical layer can have a thickness that is about one-fourth of the wavelength of light to be reflected to produce the desired structural color. Each layer of the optical layer can have a thickness of about 10 to 500 nanometers or about 90 to 200 nanometers. The optical layer can have at least two layers, where adjacent layers have different thicknesses and optionally the same or different refractive indices.

The multi-layer optical film can comprise a multilayer filter. The multilayer filter destructively interferes with light that impinges upon the bladder, where the destructive interference of the light and optionally interaction with one or more other layers or structures (e.g., a multilayer reflector, a textured structure) result in the structural color. In this regard, the layers of the multilayer filter can be designed (e.g., material selection, thickness, number of layer, and the like) so that a single wavelength of light, or a particular range of wavelengths of light, make up the structural color. For example, the range of wavelengths of light can be limited to a range within plus or minus 30 percent or a single wavelength, or within plus or minus 20 percent of a single wavelength, or within plus or minus 10 percent of a single wavelength, or within plus or minus 5 percent or a single wavelength. The range of wavelengths can be broader to produce a more iridescent structural color.

The optical layer(s) can include multiple layers where each layer independently comprises a material selected from: the transition metals, the metalloids, the lanthanides, and the actinides, as well as nitrides, oxynitrides, sulfides, sulfates, selenides, and tellurides of these. The material can be selected to provide an index of refraction that when optionally combined with the other layers of the multi-layer optical film achieves the desired result. One or more layers of the optical layer can be made of liquid crystals. Each layer of the optical layer can be made of liquid crystals. One or more layers of the optical layer can be made of a material such as: silicon dioxide, titanium dioxide, zinc sulfide, magnesium fluoride, tantalum pentoxide, aluminum oxide, or a combination thereof. Each layer of the optical layer can be made of a material such as: silicon dioxide, titanium dioxide, zinc sulfide, magnesium fluoride, tantalum pentoxide, aluminum oxide, or a combination thereof.

The multi-layer optical film can be uncolored (e.g., no pigments or dyes added to the structure or its layers), colored (e.g., pigments and/or dyes are added to the structure or its layers (e.g., dark or black color)), reflective, and/or transparent (e.g., percent transmittance of 75 percent or more). The side upon which the multi-layer optical film is disposed can be uncolored (e.g., no pigments or dyes added to the material), colored (e.g., pigments and/or dyes are added to the material (e.g., dark or black color)), reflective, and/or transparent (e.g., percent transmittance of 75 percent or more).

The optical layer(s) can be formed in a layer-by-layer manner, where each layer has a different index of refraction. Each layer of the optical layer can be formed using known techniques such as physical vapor deposition including: chemical vapor deposition, pulsed laser deposition, evaporative deposition, sputtering deposition (e.g., radio frequency, direct current, reactive, non-reactive), plasma enhanced chemical vapor deposition, electron beam deposition, atomic layer deposition, molecular beam epitaxy, cathodic arc deposition, low pressure chemical vapor deposition and wet chemistry techniques such as layer by layer deposition, sol-gel deposition, Langmuir blodgett and the like.

As mentioned above, the multi-layer optical film can include one or more layers in addition to the optical layer(s). The multi-layer optical film has a first side (e.g., the side having a surface) and a second side (e.g., the side having a surface), where the first side or the second side is adjacent the surface of the component. The one or more other layers of the multi-layer optical film can be on the first side and/or the second side of the multi-layer optical film. For example, the multi-layer optical film can include a protective layer and/or a polymeric layer such as a thermoplastic polymeric layer, where the protective layer and/or the polymeric layer can be on one or both of the first side and the second side of the multi-layer optical film. In another example, the multi-layer optical film can include a primer layer as described herein. One or more of the optional other layers can include a textured surface. Alternatively or in addition, one or more optical layers of the multi-layer optical film can include a textured surface.

A protective layer can be disposed on the first and/or second side of the optical layer to protect the optical layer. The protective layer is more durable or more abrasion resistant than the optical layer. The protective layer is optically transparent to visible light. The protective layer can be on the first side of the multi-layer optical film to protect the optical layer. All or a portion of the protective layer can include a dye or pigment in order to alter an appearance of the structural color. The protective layer can include silicon dioxide, glass, combinations of metal oxides, or mixtures of polymers. The protective layer can have a thickness of about 3 nanometers to 1 millimeter.

The protective layer can be formed using physical vapor deposition, chemical vapor deposition, pulsed laser deposition, evaporative deposition, sputtering deposition (e.g., radio frequency, direct current, reactive, non-reactive), plasma enhanced chemical vapor deposition, electron beam deposition, cathodic arc deposition, low pressure chemical vapor deposition and wet chemistry techniques such as layer by layer deposition, sol-gel deposition, Langmuir blodgett, and the like. Alternatively or in addition, the protective layer can be applied by spray coating, dip coating, brushing, spin coating, doctor blade coating, and the like.

A polymeric layer can be disposed on the first and/or the second side of the multi-layer optical film. The polymeric layer can be used to dispose the multi-layer optical film onto an article, such as, for example, when the article does not include a thermoplastic material to adhere the multi-layer optical film. The polymeric layer can comprise a polymeric adhesive material, such as a hot melt adhesive. The polymeric layer can be a thermoplastic material and can include one or more layers. The thermoplastic material can be any one of the thermoplastic material described herein. The polymeric layer can be applied using various methodologies, such as spin coating, dip coating, doctor blade coating, and so on. The polymeric layer can have a thickness of about 3 nanometer to 1 millimeter.

As described above, one or more embodiments of the present disclosure provide articles that incorporate the multi-layer optical film (e.g., single or multilayer structures) on a side of a component of the article to impart structural color. The multi-layer optical film can be disposed onto the thermoplastic material of the side of the article, and the side of the article can include a textile, including a textile comprising the thermoplastic material.

Having described the structural color structure, additional details will now be described for the optional textured surface. As described herein, the component includes the multi-layer optical film and the multi-layer optical film can include at least one optical layer and optionally a textured surface. The textured surface can be a surface of a textured structure or a textured layer. The textured surface may be provided as part of the multi-layer optical film. For example, the multi-layer optical film may comprise a textured layer or a textured structure that comprises the textured surface. The textured surface may be formed on the first or second side of the multi-layer optical film. For example, a side of the optical layer may be formed or modified to provide a textured surface, or a textured layer or textured structure can be affixed to the first or second side of the multi-layer optical film. The textured surface may be provided as part of the component to which the multi-layer optical film is disposed. For example, the multi-layer optical film may be disposed onto the surface of the component where the surface of the component is a textured surface, or the surface of the component includes a textured structure or a textured layer affixed to it.

The textured surface (or a textured structure or textured layer including the textured surface) may be provided as a feature on or part of another medium, such as a transfer medium, and imparted to a side or layer of the multi-layer optical film or to the surface of the component. For example, a mirror image or relief form of the textured surface may be provided on the side of a transfer medium, and the transfer medium contacts a side of the multi-layer optical film or the surface of the component in a way that imparts the textured surface to the multi-layer optical film or article. While the various embodiments herein may be described with respect to a textured surface of the multi-layer optical film, it will be understood that the features of the textured surface, or a textured structure or textured layer, may be imparted in any of these ways.

The textured surface can contribute to the structural color resulting from the multi-layer optical film. As described herein, structural coloration is imparted, at least in part, due to optical effects caused by physical phenomena such as scattering, diffraction, reflection, interference or unequal refraction of light rays from a multi-layer optical film. The textured surface (or its mirror image or relief) can include a plurality of profile features and flat or planar areas. The plurality of profile features included in the textured surface, including their size, shape, orientation, spatial arrangement, etc., can affect the light scattering, diffraction, reflection, interference and/or refraction resulting from the multi-layer optical film. The flat or planar areas included in the textured surface, including their size, shape, orientation, spatial arrangement, etc., can affect the light scattering, diffraction, reflection, interference and/or refraction resulting from the multi-layer optical film. The desired structural color can be designed, at least in part, by adjusting one or more of properties of the profile features and/or flat or planar areas of the textured surface.

The profile features (also referred to as "topographical structures") can extend from a side of the flat areas, so as to provide the appearance of projections and/or depressions therein. A profile feature may include various combinations of projections and depressions.

For example, a profile feature may include a projection with one or more depressions therein, a depression with one or more projections therein, a projection with one or more further projections thereon, a depression with one or more further depressions therein, and the like. The flat areas do not have to be completely flat and can include texture, roughness, and the like. The texture of the flat areas may not contribute much, if any, to the imparted structural color. The texture of the flat areas typically contributes to the imparted structural color. For clarity, the profile features and flat areas are described in reference to the profile features extending above the flat areas, but the inverse (e.g., dimensions, shapes, and the like) can apply when the profile features are depressions in the textured structure.

The textured surface can comprise a thermoplastic material or a thermoset material. The profile features and the flat areas can be formed using a thermoplastic material. For example, when the thermoplastic material is heated above its softening temperature a textured surface can be formed in the thermoplastic material such as by molding, stamping, printing, compressing, cutting, etching, vacuum forming, etc., the thermoplastic material to form profile features and flat areas therein. The textured surface can be imparted on a side of a thermoplastic material. The textured surface can be formed in a layer of thermoplastic material. The profile features and the flat areas can be made of the same thermoplastic material or a different thermoplastic material. In an embodiment, the exterior-facing side or surface and/or the interior-facing side or surface of the bladder can be made of a thermoplastic material and the textured surface or textured surface can be formed as described.

The textured surface generally has a length dimension extending along an x-axis, and a width dimension extending along a z-axis, and a thickness dimension extending along a y-axis. The textured surface has a generally planar portion extending in a first plane that extends along the x-axis and the z-axis. A profile feature can extend outward from the first plane, so as to extend above or below the plane x. A profile feature may extend generally orthogonal to the first plane, or at an angle greater to or less than 90 degrees to the first plane.

The dimension (e.g., length, width, height, diameter, depending upon the shape of the profile feature) of each profile feature can be within the nanometer to micrometer range. A textured surface can have a profile feature and/or flat area with a dimension of about 10 nanometers to about 500 micrometers. The profile feature can have dimensions in the nanometer range, e.g., from about 10 nanometers to about 1000 nanometers. All of the dimensions of the profile feature (e.g., length, width, height, diameter, depending on the geometry) can be in the nanometer range, e.g., from about 10 nanometers to about 1000 nanometers. The textured surface can have a plurality of profile features having dimensions that are 1 micrometer or less. In this context, the phrase "plurality of the profile features" is meant to mean that about 50 percent or more, about 60 percent or more, about 70 percent or more, about 80 percent or more, about 90 percent or more, or about 99 percent or more of the profile features have a dimension in this range. The profile features can have a ratio of width:height and/or length:height dimensions of about 1:2 and 1:100, or 1:5 and 1:50, or 1:5 and 1:10.

The textured surface can have a profile feature and/or flat area with a dimension within the micrometer range of dimensions. A textured surface can have a profile feature and/or flat area with a dimension of about 1 micrometer to about 500 micrometers. All of the dimensions of the profile feature (e.g., length, width, height, diameter, depending on the geometry) can be in the micrometer range, e.g., from about 1 micrometer to about 500 micrometers. The textured surface can have a plurality of profile features having dimensions that are from about 1 micrometer to about 500 micrometer. In this context, the phrase "plurality of the profile features" is meant to mean that about 50 percent or more, about 60 percent or more, about 70 percent or more, about 80 percent or more, about 90 percent or more, or about 99 percent or more of the profile features have a dimension in this range. The height of the profile features (or depth if depressions) can be about 0.1 and 50 micrometers, about 1 to 5 micrometers, or 2 to 3 micrometers. The profile features can have a ratio of width:height and/or length:height dimensions of about 1:2 and 1:100, or 1:5 and 1:50, or 1:5 and 1:10.

A textured surface can have a plurality of profile features having a mixture of size dimensions within the nanometer to micrometer range (e.g., a portion of the profile features are on the nanometer scale and a portion of the profile features are on the micrometer scale). A textured surface can have a plurality of profile features having a mixture of dimensional ratios. The textured surface can have a profile feature having one or more nanometer-scale projections or depressions on a micrometer-scale projection or depression.

The profile feature can have height and width dimensions that are within a factor of three of each other ($0.33w \leq h \leq 3w$ where w is the width and h is the height of the profile feature) and/or height and length dimensions that are within a factor of three of each other ($0.33l \leq h \leq 3l$ where l is the length and h is the height of the profile feature). The profile feature can have a ratio of length:width that is from about 1:3 to about 3:1, or about 1:2 to about 2:1, or about 1:1.5 to about 1.5:1, or about 1:1.2 to about 1.2:1, or about 1:1. The width and length of the profile features can be substantially the same or different.

The profile features can have a certain spatial arrangement. The spatial arrangement of the profile features may be uniform, such as spaced evenly apart or forming a pattern. The spatial arrangement can be random. Adjacent profile features can be about 1 to 100 micrometers apart or about 5 to 100 micrometers apart. The desired spacing can depend, at least in part, on the size and/or shape of the profile surfaces and the desired structural color effect.

The profile features can have a certain cross-sectional shape (with respect to a plane parallel the first plane). The textured surface can have a plurality of profile features having the same or similar cross-sectional shape. The textured surface has a plurality of profile features having a mixture of different cross-sectional shapes. The cross-sectional shapes of the profile features can include polygonal (e.g., square or triangle or rectangle cross section), circular, semi-circular, tubular, oval, random, high and low aspect ratios, overlapping profile features, and the like.

The profile feature (e.g., about 10 nanometers to 500 micrometers) can include an upper, convexly curved surface. The curved surface may extend symmetrically either side of an uppermost point.

The profile feature can include protrusions from the textured surface. The profile feature can include indents (hollow areas) formed in the textured surface. The profile feature can have a smooth, curved shape (e.g., a polygonal cross-section with curved corners).

The profile features (whether protrusions or depressions) can be approximately conical or frusto-conical (i.e. the projections or indents may have horizontally or diagonally flattened tops) or have an approximately part-spherical surface (e.g., a convex or concave surface respectively having a substantially even radius of curvature).

The profile features may have one or more sides or edges that extend in a direction that forms an angle to the first plane of the textured surface. The angle between the first plane and a side or edge of the profile feature is about 45 degrees or less, about 30 degrees or less, about 25 degrees or less, or about 20 degrees or less. The one or more sides or edges may extend in a linear or planar orientation, or may be curved so that the angle changes as a function of distance from the first plane. The profile features may have one or more sides that include step(s) and/or flat side(s). The profile feature can have one or more sides (or portions thereof) that can be orthogonal or perpendicular to the first plane of the textured surface, or extend at an angle of about 10 degrees to 89 degrees to the first plane (90 degrees being perpendicular or orthogonal to the first plane)). The profile feature can have a side with a stepped configuration, where portions of the side can be parallel to the first plane of the textured surface or have an angle of about 1 degrees to 179 degrees (0 degrees being parallel to the first plane)).

The textured surface can have profile features with varying shapes (e.g., the profile features can vary in shape, height, width and length among the profile features) or profile features with substantially uniform shapes and/or dimensions. The structural color produced by the textured surface can be determined, at least in part, by the shape, dimensions, spacing, and the like, of the profile features.

The profile features can be shaped so as to result in a portion of the surface (e.g., about 25 to 50 percent or more) being about normal to the incoming light when the light is incident at the normal to the first plane of the textured surface. The profile features can be shaped so as to result in a portion of the surface (e.g., about 25 to 50 percent or more) being about normal to the incoming light when the light is incident at an angle of up to 45 degrees to the first plane of the textured surface.

The spatial orientation of the profile features on the textured surface is set to reduce distortion effects, e.g., caused by the interference of one profile feature with another in regard to the structural color of the surface. Since the shape, dimension, relative orientation of the profile features can vary considerably across the textured surface, the desired spacing and/or relative positioning for a particular area (e.g., in the micrometer range or about 1 to 10 square micrometers) having profile features can be appropriately determined. As discussed herein, the shape, dimension, relative orientation of the profile features affect the contours of the optical layer, so the dimensions (e.g., thickness), index of refraction, number of layers in the optical layer are considered when designing the textured side of the texture layer.

The profile features are located in nearly random positions relative to one another across a specific area of the textured surface (e.g., in the micrometer range or about 1 to 10 square micrometers to centimeter range or about 0.5 to 5 square centimeters, and all range increments therein), where the randomness does not defeat the purpose of producing the structural color. In other words, the randomness is consistent with the spacing, shape, dimension, and relative orientation of the profile features, the dimensions (e.g., thickness), index of refraction, and number of layers in the optical layer, and the like, with the goal to achieve the structural color.

The profile features are positioned in a set manner relative to one another across a specific area of the textured surface to achieve the purpose of producing the structural color. The relative positions of the profile features do not necessarily follow a pattern, but can follow a pattern consistent with the desired structural color. As mentioned above and herein, various parameters related to the profile features, flat areas, and optical layer can be used to position the profile features in a set manner relative to one another.

The textured surface can include micro and/or nanoscale profile features that can form gratings (e.g., a diffractive grating), photonic crystal structure, a selective mirror structure, crystal fiber structures, deformed matrix structures, spiraled coiled structures, surface grating structures, and combinations thereof. The textured surface can include micro and/or nanoscale profile features that form a grating having a periodic or non-periodic design structure to produce the desired structural color. The micro and/or nanoscale profile features can have a peak-valley pattern of profile features and/or flat areas to produce the desired structural color. The grading can be an Echelette grating.

Figure 3A:
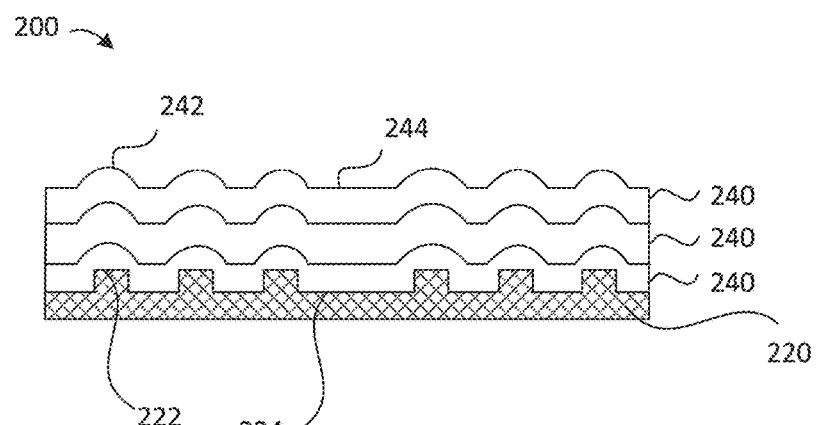
FIGS. 3A-3B illustrate side views of exemplary multi-layer optical films of the present disclosure.
Figure 3B:
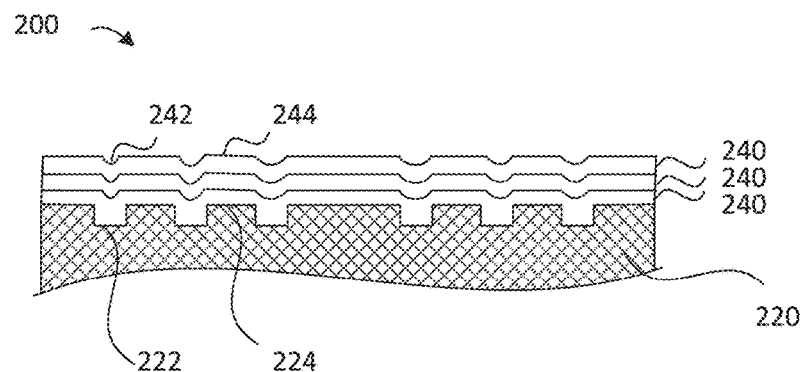

The profile features and the flat areas of the textured surface in the multi-layer optical film can appear as topographical undulations in each layer of the optical layer. For example, referring to FIGS. 3A and 3B, a multi-layer optical film 200 includes a textured surface 220 having a plurality of profile features 222 and flat areas 224. As described herein, one or more of the profile features 222 can be projections from a surface of the textured surface 220 (as shown in FIG. 3A), and/or one or more of the profile features 222 can be depressions in a surface of the textured surface 220 (as shown in FIG. 3B). One or more optical layers 240 are disposed on the side or surface of the textured surface 220 having the profile features 222 and flat areas 224. In some embodiments, the resulting topography of the one or more optical layers 240 is not identical to the topography of the textured surface 220, but rather, the one or more optical layers 240 can have elevated or depressed regions 242 which are either elevated or depressed relative to the height of the planar regions 244 and which roughly correspond to the location of the profile features 222 of the textured surface 220. The one or more optical layers 240 also have planar regions 244 that roughly correspond to the location of the flat areas 224 of the textured surface 220. Due to the presence of the elevated or depressed regions 242 and the planar regions 244, the resultant overall topography of the optical layer 240 can be that of an undulating or wave-like surface. The dimension, shape, and spacing of the profile features along with the number of layers of the optical layer, the thickness of each of the layers, refractive index of each layer, and the type of material, can be used to produce a multi-layer optical film which results in a particular structural color.

Now having described the multi-layer optical film and the textured surface, additional details will be provided for the optionally present primer layer. The multi-layer optical film is used to produce the structural color, where the multi-layer optical film can include (e.g., as part of the multi-layer optical film) or use the primer layer to produce the structural color. As described herein, the multi-layer optical film can also include (e.g., as part of multi-layer optical film) the optional textured surface, such as a texture layer and/or a textured surface. The combination of the multi-layer optical film and the optional texture layer and the optional primer layer can form a structure having one of the following designs: texture layer/primer layer/multi-layer optical film or primer layer/texture layer/multi-layer optical film. The primer layer can have a thickness of about 3 nanometers to 200 micrometers, or about 1 to about 200 micrometers, or about 10 to about 100 micrometers, or about 10 to about 80 micrometers. The structure can include the combination of the primer layer, the multi-layer optical film, and (optionally) textured surface. Selection of variables associated with the primer layer, texture layer, and the multi-layer optical film, can be used to control and select the desired structural color.

The structure can include the primer layer, the textured surface (optionally), and the multi-layer optical film (e.g., optical element or layer), where the multi-layer optical film is disposed on the textured surface or the primer layer, depending upon the design. The combination of the primer layer, the textured surface, and the multi-layer optical film imparts structural color, to the bladder, where the structural color is different than the primer color, optionally with or without the application of pigments or dyes to the bladder. The multi-layer optical film can be disposed onto the primer layer and/or the textured surface. The primer layer can include the textured surface as described herein. For example, the primer layer can be formed in a way so that it has the textured surface.

The primer layer can include a paint layer (e.g., dyes, pigments, and a combination thereof), an ink layer, a reground layer, an at least partially degraded polymer layer, a metal layer, an oxide layer, or a combination thereof. The primer layer can have a light or dark color. The primer layer can have a dark color. For example the dark color can be selected from: black, shades of black, brown, dark shades of brown, dark shades of red, dark shades of orange, dark shades of yellow, dark shades of green, dark shades of cyan, dark shades of blue, dark shades of violet, grey, dark shades of gray, dark shades of magenta, dark shades of indigo, tones, tints, shades, or hues of any of these, and a combination thereof. The color can be defined using the L*a*b system, where the value of L* can be about 70 or less, about 60 or less, about 50 or less, about 40 or less, or about 30 or less and a* and b* coordinate values can vary across the positive and negative value scales.

The primer layer can be formed using digital printing, inkjet printing, offset printing, pad printing, screen printing, flexographic printing, heat transfer printing, physical vapor deposition including: chemical vapor deposition, pulsed laser deposition, evaporative deposition, sputtering deposition (radio frequency, direct current, reactive, non-reactive), plasma enhanced chemical vapor deposition, electron beam deposition, cathodic arc deposition, low pressure chemical vapor deposition and wet chemistry techniques such as layer by layer deposition, sol-gel deposition, or Langmuir blodgett. Alternatively or in addition, the primer layer can be applied by spray coating, dip coating, brushing, spin coating, doctor blade coating, and the like.

The primer layer can have a percent transmittance of about 40% or less, about 30% or less, about 20% or less, about 15% or less, about 10% or less, about 5% or less, or about 1% or less, where "less" can include about 0% (e.g., 0 to 0.01 or 0 to 0.1), about 1%, about 2.5%, or about 5%.

The paint layer can include a paint composition that, upon applying to the bladder, forms a thin layer. The thin layer can be a solid film having a dark color, such as those described above. The paint can include known paint compositions that can comprise one or more of the following components: one or more paint resin, one or more polymers, one or more dyes, and one or more pigments as well as water, film-forming solvents, drying agents, thickeners, surfactants, anti-skinning agents, plasticizers, mildewcides, mar-resistant agents, anti-flooding agents, and combinations thereof.

The primer layer can comprise a reground, and at least partially degraded, polymer layer. The reground, and at least partially degraded, polymer layer can have a dark color, such as those described above.

The primer layer can include a metal layer or the oxide layer. The metal layer or the oxide layer can have a dark color, such as those described above. The oxide layer can be a metal oxide, a doped metal oxide, or a combination thereof. The metal layer, the metal oxide or the doped metal oxide can include the following: the transition metals, the metalloids, the lanthanides, and the actinides, as well as nitrides, oxynitrides, sulfides, sulfates, selenides, tellurides and a combination of these. The metal oxide can include titanium oxide, aluminum oxide, silicon dioxide, tin dioxide, chromia, iron oxide, nickel oxide, silver oxide, cobalt oxide, zinc oxide, platinum oxide, palladium oxide, vanadium oxide, molybdenum oxide, lead oxide, and combinations thereof as well as doped versions of each. In some aspects, the primer layer can consist essentially of a metal oxide. In some aspects, the primer layer can consist essentially of titanium dioxide or silicon dioxide. In some aspects, the primer layer can consist essentially of titanium dioxide. The metal oxide can be doped with water, inert gasses (e.g., argon), reactive gasses (e.g., oxygen or nitrogen), metals, small molecules, and a combination thereof. In some aspects, the primer layer can consist essentially of a doped metal oxide or a doped metal oxynitride or both.

The primer layer can be a coating on the surface of the bladder. The coating can be chemically bonded (e.g., covalently bonded, ionically bonded, hydrogen bonded, and the like) to the surface of the bladder. The coating has been found to bond well to a surface made of a polymeric material. In an example, the surface of the bladder can be made of a polymeric material such as a polyurethane, including a thermoplastic polyurethane (TPU), as those described herein.

The coating can be a crosslinked coating that includes one or more colorants such as solid pigment particles or dye. The crosslinked coating can be a matrix of crosslinked polymers (e.g., a crosslinked polyester polyurethane polymer or copolymer). The colorants can be entrapped in the coating, including entrapped in the matrix of crosslinked polymers. The solid pigment particles or dye can be physically entrapped in the crosslinked polymer matrix, can be chemically bonded (e.g., covalently bonded, ionically bonded, hydrogen bonded, and the like, with the coating including the polymeric matrix or with the material forming the surface of the bladder to which the coating is applied), or a combination of physically bonded and chemically bonded with the coating or bladder. The crosslinked coating can have a thickness of about 0.01 micrometers to 1000 micrometers.

The coating can be a product (or also referred to as "crosslinked product") of crosslinking a polymeric coating composition. The polymeric coating composition can include one or more colorants (e.g., solid pigment particles or dye) in a dispersion of polymers. The dispersion of polymers can include a water-borne dispersion of polymers such as a water-borne dispersion of polyurethane polymers, including polyester polyurethane copolymers). The water-borne dispersion of polymers can be crosslinked to entrap the colorants. The colorants can be physically entrapped in the crosslinked product, can be chemically bonded (e.g., covalently bonded, ionically bonded, hydrogen bonded, and the like, with the crosslinked copolymer matrix), or can be both physically bonded and chemically bonded with the crosslinked product. The product can be formed by crosslinking the polymeric coating composition. The product can have a thickness of about 0.01 micrometer to 1000 micrometers.

The coating can include colorants such a pigment (e.g., a solid pigment particle) or a dye. The solid pigment particles can include inorganic pigments such as metal and metal oxides such as homogeneous inorganic pigments, core-shell pigments and the like, as well as carbon pigments (e.g., carbon black), clay earth pigments, and ultramarine pigments.

The solid pigment particles can be biological or organic pigments. The solid pigment particles can be of a type known in the art as an extender pigment, which include, but are not limited to, calcium carbonate, calcium silicate, mica, clay, silica, barium sulfate and the like. The amount of the solid pigment particles sufficient to achieve the desired color intensity, shade, and opacity, can be in amounts up to about 5 percent to 25 percent or more by weight of the coating. The pigments can include those sold by KP Pigments such as pearl pigments, color shift pigments (e.g., CALYPSO, JEDI, VERO, BLACKHOLE, LYNX, ROSE GOLD, and the like), hypershift pigments, interference pigments and the like.

The colorant can be a dye such as an anionic dye, a cationic dye, a direct dye, a metal complex dye, a basic dye, a disperse dye, a solvent dye, a polymeric dye, a polymeric dye colorant, or a nonionic dye, where the coating can include one or more dyes and/or types of dyes. The dye can be a water-miscible dye. The dye can be a solubilized dye. The anionic dye can be an acid dye. The dye can be applied separately from the coating (e.g., either before or after the coating is applied and/or cured).

Acid dyes are water-soluble anionic dyes. Acid dyes are available in a wide variety, from dull tones to brilliant shades. Chemically, acid dyes include azo, anthraquinone and triarylmethane compounds. The "Color Index" (C.I.), published jointly by the Society of Dyers and Colourists (UK) and by the American Association of Textile Chemists and Colorists (USA), is the most extensive compendium of dyes and pigments for large scale coloration purposes, including 12000 products under 2000 C.I. generic names. In the C.I. each compound is presented with two numbers referring to the coloristic and chemical classification. The "generic name" refers to the field of application and/or method of coloration, while the other number is the "constitution number." Examples of acid dyes include Acid Yellow 1, 17, 23, 25, 34, 42, 44, 49, 61, 79, 99, 110, 116, 127, 151, 158:1, 159, 166, 169, 194, 199, 204, 220, 232, 241, 246, and 250; Acid Red, 1, 14, 17, 18, 42, 57, 88, 97, 118, 119, 151, 183, 184, 186, 194, 195, 198, 211, 225, 226, 249, 251, 257, 260, 266, 278, 283, 315, 336, 337, 357, 359, 361, 362, 374, 405, 407, 414, 418, 419, and 447; Acid Violet 3, 5, 7, 17, 54, 90, and 92; Acid Brown 4, 14, 15, 45, 50, 58, 75, 97, 98, 147, 160:1, 161, 165, 191, 235, 239, 248, 282, 283, 289, 298, 322, 343, 349, 354, 355, 357, 365, 384, 392, 402, 414, 420, 422, 425, 432, and 434; Acid Orange 3, 7, 10, 19, 33, 56, 60, 61, 67, 74, 80, 86, 94, 139, 142, 144, 154, and 162; Acid Blue 1, 7, 9, 15, 92, 133, 158, 185, 193, 277, 277:1, 314, 324, 335, and 342; Acid Green 1, 12, 68:1, 73, 80, 104, 114, and 119; Acid Black 1, 26, 52, 58, 60, 64, 65, 71, 82, 84, 107, 164, 172, 187, 194, 207, 210, 234, 235, and combinations of these. The acid dyes may be used singly or in any combination in the ink composition.

Acid dyes and nonionic disperse dyes are commercially available from many sources, including Dystar L.P., Charlotte, N.C. under the tradename TELON, Huntsman Corporation, Woodlands, Tex., USA under the tradename ERIONYL and TECTILON, BASF SE, Ludwigshafen, Germany under the tradename BASACID, and Bezema AG, Montlingen, Switzerland under the tradename Bemacid.

The colorant can include the dye and a quaternary (tetraalkyl) ammonium salt, in particular when the dye is acidic dye. The quaternary (tetraalkyl) ammonium salt can react with the dye (e.g., acid dye) to form a complexed dye that can be used in the coating. The "alkyl" group can include C1 to C10 alkyl groups. The quaternary (tetraalkyl) ammonium salt can be selected from soluble tetrabutylammonium compounds and tetrahexylammonium compounds. The counterion of the quaternary ammonium salt should be selected so that the quaternary ammonium salt forms a stable solution with the dye (e.g., anionic dye). The quaternary ammonium compound may be, for example, a halide (such as chloride, bromide or iodide), hydroxide, sulfate, sulfite, carbonate, perchlorate, chlorate, bromate, iodate, nitrate, nitrite, phosphate, phosphite, hexfluorophosphite, borate, tetrafluoroborate, cyanide, isocyanide, azide, thiosulfate, thiocyanate, or carboxylate (such as acetate or oxalate). The tetraalkylammonium compound can be or include a tetrabutylammonium halide or tetrahexylammonium halide, particularly a tetrabutylammonium bromide or chloride or a tetrahexylammonium bromide or chloride. The coating (e.g., coating, polymeric coating composition (prior to curing) can include about 1 to 15 weight percent of the quaternary ammonium salt. The molar ratio of the acid dye to the quaternary ammonium compound can range from about 3:1 to 1:3 or about 1.5:1 to 1:1.5.

The coating (e.g., coating, polymeric coating composition (prior to curing), monomers and/or polymers of the matrix of crosslinked polymers, or precursors of the coating) can include a cross-linker, which functions to crosslink the polymeric components of the coating.

The cross-linker can be a water-borne cross-linker. The cross-linker can include one or more of the following: a polycarboxylic acid crosslinking agent, an aldehyde crosslinking agent, a polyisocyanate crosslinking agent, or a combination thereof. The polycarboxylic acid crosslinking agent can be a polycarboxylic acid having from 2 to 9 carbon atoms. For example, the cross-linker can include a polyacrylic acid, a polymaleic acid, a copolymer of acid, a copolymer of maleic acid, fumaric acid, or 1, 2, 3, 4-butanetetracarboxylic acid. The concentration of the cross-linker can be about 0.01 to 5 weight percent or 1 to 3 weight percent of the coating.

The coating (e.g., coating, polymeric coating composition (prior to curing), monomers and/or polymers of the matrix of crosslinked polymers, or precursors of the coating) can include a solvent. The solvent can be an organic solvent. The organic solvent can be a water-miscible organic solvent. The coating may not include water, or may be essentially free of water. For example, the solvent can be or includes acetone, ethanol, 2-propanol, ethyl acetate, isopropyl acetate, methanol, methyl ethyl ketone, 1-butanol, t-butanol, or any mixture thereof.

Additional details are provided regarding the polymeric materials referenced herein for example, the polymers described in reference to the bladder, components of the bladder, article, structure, layer, film, foam, primer layer, coating, and like the. The polymer can be a thermoset polymer or a thermoplastic polymer. The polymer can be an elastomeric polymer, including an elastomeric thermoset polymer or an elastomeric thermoplastic polymer. The polymer can be selected from: polyurethanes (including elastomeric polyurethanes, thermoplastic polyurethanes (TPUs), and elastomeric TPUs), polyesters, polyethers, polyamides, vinyl polymers (e.g., copolymers of vinyl alcohol, vinyl esters, ethylene, acrylates, methacrylates, styrene, and so on), polyacrylonitriles, polyphenylene ethers, polycarbonates, polyureas, polystyrenes, co-polymers thereof (including polyester-polyurethanes, polyether-polyurethanes, polycarbonate-polyurethanes, polyether block polyamides (PEBAs), and styrene block copolymers), and any combination thereof, as described herein. The polymer can include one or more polymers selected from the group consisting of polyesters, polyethers, polyamides, polyurethanes, polyolefins copolymers of each, and combinations thereof.

The term "polymer" refers to a chemical compound formed of a plurality of repeating structural units referred to as monomers. Polymers often are formed by a polymerization reaction in which the plurality of structural units become covalently bonded together. When the monomer units forming the polymer all have the same chemical structure, the polymer is a homopolymer. When the polymer includes two or more monomer units having different chemical structures, the polymer is a copolymer. One example of a type of copolymer is a terpolymer, which includes three different types of monomer units. The co-polymer can include two or more different monomers randomly distributed in the polymer (e.g., a random co-polymer). Alternatively, one or more blocks containing a plurality of a first type of monomer can be bonded to one or more blocks containing a plurality of a second type of monomer, forming a block copolymer. A single monomer unit can include one or more different chemical functional groups.

Polymers having repeating units which include two or more types of chemical functional groups can be referred to as having two or more segments. For example, a polymer having repeating units of the same chemical structure can be referred to as having repeating segments. Segments are commonly described as being relatively harder or softer based on their chemical structures, and it is common for polymers to include relatively harder segments and relatively softer segments bonded to each other in a single monomeric unit or in different monomeric units. When the polymer includes repeating segments, physical interactions or chemical bonds can be present within the segments or between the segments or both within and between the segments. Examples of segments often referred to as hard segments include segments including a urethane linkage, which can be formed from reacting an isocyanate with a polyol to form a polyurethane. Examples of segments often referred to as soft segments include segments including an alkoxy functional group, such as segments including ether or ester functional groups, and polyester segments. Segments can be referred to based on the name of the functional group present in the segment (e.g., a polyether segment, a polyester segment), as well as based on the name of the chemical structure which was reacted in order to form the segment (e.g., a polyol-derived segment, an isocyanate-derived segment). When referring to segments of a particular functional group or of a particular chemical structure from which the segment was derived, it is understood that the polymer can contain up to 10 mole percent of segments of other functional groups or derived from other chemical structures. For example, as used herein, a polyether segment is understood to include up to 10 mole percent of non-polyether segments.

As previously described, the polymer can be a thermoplastic polymer. In general, a thermoplastic polymer softens or melts when heated and returns to a solid state when cooled. The thermoplastic polymer transitions from a solid state to a softened state when its temperature is increased to a temperature at or above its softening temperature, and a liquid state when its temperature is increased to a temperature at or above its melting temperature. When sufficiently cooled, the thermoplastic polymer transitions from the softened or liquid state to the solid state. As such, the thermoplastic polymer may be softened or melted, molded, cooled, re-softened or re-melted, re-molded, and cooled again through multiple cycles. For amorphous thermoplastic polymers, the solid state is understood to be the "rubbery" state above the glass transition temperature of the polymer. The thermoplastic polymer can have a melting temperature from about 90 degrees C. to about 190 degrees C. when determined in accordance with ASTM D3418-97 as described herein below, and includes all subranges therein in increments of 1 degree. The thermoplastic polymer can have a melting temperature from about 93 degrees C. to about 99 degrees C. when determined in accordance with ASTM D3418-97 as described herein below. The thermoplastic polymer can have a melting temperature from about 112 degrees C. to about 118 degrees C. when determined in accordance with ASTM D3418-97 as described herein below.

The glass transition temperature is the temperature at which an amorphous polymer transitions from a relatively brittle "glassy" state to a relatively more flexible "rubbery" state. The thermoplastic polymer can have a glass transition temperature from about −20 degrees C. to about 30 degrees C. when determined in accordance with ASTM D3418-97 as described herein below. The thermoplastic polymer can have a glass transition temperature (from about −13 degree C. to about −7 degrees C. when determined in accordance with ASTM D3418-97 as described herein below. The thermoplastic polymer can have a glass transition temperature from about 17 degrees C. to about 23 degrees C. when determined in accordance with ASTM D3418-97 as described herein below.

The thermoplastic polymer can have a melt flow index from about 10 to about 30 cubic centimeters per 10 minutes ($cm^3/10$ min) when tested in accordance with ASTM D1238-13 as described herein below at 160 degrees C. using a weight of 2.16 kilograms (kg). The thermoplastic polymer can have a melt flow index from about 22 $cm^3/10$ min to about 28 $cm^3/10$ min when tested in accordance with ASTM D1238-13 as described herein below at 160 degrees C. using a weight of 2.16 kg.

The thermoplastic polymer can have a cold Ross flex test result of about 120,000 to about 180,000 cycles without cracking or whitening when tested on a thermoformed plaque of the thermoplastic polymer in accordance with the cold Ross flex test as described herein below. The thermoplastic polymer can have a cold Ross flex test result of about 140,000 to about 160,000 cycles without cracking or whitening when tested on a thermoformed plaque of the thermoplastic polymer in accordance with the cold Ross flex test as described herein below.

The thermoplastic polymer can have a modulus from about 5 megaPascals (MPa) to about 100 MPa when determined on a thermoformed plaque in accordance with ASTM D412-98 Standard Test Methods for Vulcanized Rubber and Thermoplastic Rubbers and Thermoplastic Elastomers-Tension with modifications described herein below. The thermoplastic polymer can have a modulus from about 20 MPa to about 80 MPa when determined on a thermoformed plaque in accordance with ASTM D412-98 Standard Test Methods for Vulcanized Rubber and Thermoplastic Rubbers and Thermoplastic Elastomers-Tension with modifications described herein below.

The polymer can be a thermoset polymer. As used herein, a "thermoset polymer" is understood to refer to a polymer which cannot be heated and melted, as its melting temperature is at or above its decomposition temperature. A "thermoset material" refers to a material which comprises at least one thermoset polymer. The thermoset polymer and/or thermoset material can be prepared from a precursor (e.g., an uncured or partially cured polymer or material) using thermal energy and/or actinic radiation (e.g., ultraviolet radiation, visible radiation, high energy radiation, infrared radiation) to form a partially cured or fully cured polymer or material which no longer remains fully thermoplastic. In some cases, the cured or partially cured polymer or material may remain thermoelastic properties, in that it is possible to partially soften and mold the polymer or material at elevated temperatures and/or pressures, but it is not possible to melt the polymer or material. The curing can be promoted, for example, with the use of high pressure and/or a catalyst. In many examples, the curing process is irreversible since it results in cross-linking and/or polymerization reactions of the precursors. The uncured or partially cured polymers or materials can be malleable or liquid prior to curing. In some cases, the uncured or partially cured polymers or materials can be molded into their final shape, or used as adhesives. Once hardened, a thermoset polymer or material cannot be re-melted in order to be reshaped. The textured surface can be formed by partially or fully curing an uncured precursor material to lock in the textured surface of the textured structure.

Polyurethane

The polymer can be a polyurethane, such as a thermoplastic polyurethane (also referred to as "TPU"). Alternatively, the polymer can be a thermoset polyurethane.

Additionally, polyurethane can be an elastomeric polyurethane, including an elastomeric TPU or an elastomeric thermoset polyurethane. The elastomeric polyurethane can include hard and soft segments. The hard segments can comprise or consist of urethane segments (e.g., isocyanate-derived segments). The soft segments can comprise or consist of alkoxy segments (e.g., polyol-derived segments including polyether segments, or polyester segments, or a combination of polyether segments and polyester segments). The polyurethane can comprise or consist essentially of an elastomeric polyurethane having repeating hard segments and repeating soft segments.

One or more of the polyurethanes can be produced by polymerizing one or more isocyanates with one or more polyols to produce polymer chains having carbamate linkages (—N(CO)O—) as illustrated below in Formula 1, where the isocyanate(s) each preferably include two or more isocyanate (—NCO) groups per molecule, such as 2, 3, or 4 isocyanate groups per molecule (although, mono-functional isocyanates can also be optionally included, e.g., as chain terminating units).

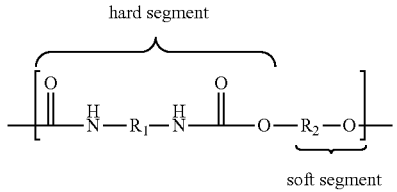

(Formula 1)

Each $R_1$ group and $R_2$ group independently is an aliphatic or aromatic group. Optionally, each $R_2$ can be a relatively hydrophilic group, including a group having one or more hydroxyl groups.

Additionally, the isocyanates can also be chain extended with one or more chain extenders to bridge two or more isocyanates, increasing the length of the hard segment. This can produce polyurethane polymer chains as illustrated below in Formula 2, where $R_3$ includes the chain extender. As with each $R_1$ and $R_3$, each $R_3$ independently is an aliphatic or aromatic functional group.

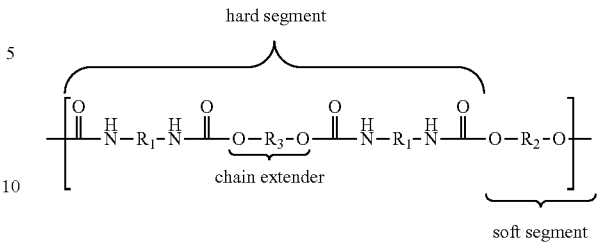

(Formula 2)

Each $R_1$ group in Formulas 1 and 2 can independently include a linear or branched group having from 3 to 30 carbon atoms, based on the particular isocyanate(s) used, and can be aliphatic, aromatic, or include a combination of aliphatic portions(s) and aromatic portion(s). The term "aliphatic" refers to a saturated or unsaturated organic molecule or portion of a molecule that does not include a cyclically conjugated ring system having delocalized pi electrons. In comparison, the term "aromatic" refers to an organic molecule or portion of a molecule having a cyclically conjugated ring system with delocalized pi electrons, which exhibits greater stability than a hypothetical ring system having localized pi electrons.

Each $R_1$ group can be present in an amount of about 5 percent to about 85 percent by weight, from about 5 percent to about 70 percent by weight, or from about 10 percent to about 50 percent by weight, based on the total weight of the reactant compounds or monomers which form the polymer.

In aliphatic embodiments (from aliphatic isocyanate(s)), each $R_1$ group can include a linear aliphatic group, a branched aliphatic group, a cycloaliphatic group, or combinations thereof. For instance, each $R_1$ group can include a linear or branched alkylene group having from 3 to 20 carbon atoms (e.g., an alkylene having from 4 to 15 carbon atoms, or an alkylene having from 6 to 10 carbon atoms), one or more cycloalkylene groups having from 3 to 8 carbon atoms (e.g., cyclopropyl, cyclobutyl, cyclopentyl, cyclohexyl, cycloheptyl, or cyclooctyl), and combinations thereof. The term "alkene" or "alkylene" as used herein refers to a bivalent hydrocarbon. When used in association with the term $C_n$ it means the alkene or alkylene group has "n" carbon atoms. For example, $C_{1-6}$ alkylene refers to an alkylene group having, e.g., 1, 2, 3, 4, 5, or 6 carbon atoms.

Examples of suitable aliphatic diisocyanates for producing the polyurethane polymer chains include hexamethylene diisocyanate (HDI), isophorone diisocyanate (IPDI), butylenediisocyanate (BDI), bisisocyanatocyclohexylmethane (HMDI), 2,2,4-trimethylhexamethylene diisocyanate (TMDI), bisisocyanatomethylcyclohexane, bisisocyanatomethyltricyclodecane, norbomane diisocyanate (NDI), cyclohexane diisocyanate (CHDI), 4,4'-dicyclohexylmethane diisocyanate (H12MDI), diisocyanatododecane, lysine diisocyanate, and combinations thereof.

The isocyanate-derived segments can include segments derived from aliphatic diisocyanate. A majority of the isocyanate-derived segments can comprise segments derived from aliphatic diisocyanates. At least 90% of the isocyanate-derived segments are derived from aliphatic diisocyanates. The isocyanate-derived segments can consist essentially of segments derived from aliphatic diisocyanates. The aliphatic diisocyanate-derived segments can be derived substantially (e.g., about 50 percent or more, about 60 percent or more, about 70 percent or more, about 80 percent or more, about 90 percent or more) from linear aliphatic diisocyanates. At least 80% of the aliphatic diisocyanate-derived segments can be derived from aliphatic diisocyanates that are free of side chains. The segments derived from aliphatic diisocyanates can include linear aliphatic diisocyanates having from 2 to 10 carbon atoms.

When the isocyanate-derived segments are derived from aromatic isocyanate(s)), each $R_1$ group can include one or more aromatic groups, such as phenyl, naphthyl, tetrahydronaphthyl, phenanthrenyl, biphenylenyl, indanyl, indenyl, anthracenyl, and fluorenyl. Unless otherwise indicated, an aromatic group can be an unsubstituted aromatic group or a substituted aromatic group, and can also include heteroaromatic groups. "Heteroaromatic" refers to monocyclic or polycyclic (e.g., fused bicyclic and fused tricyclic) aromatic ring systems, where one to four ring atoms are selected from oxygen, nitrogen, or sulfur, and the remaining ring atoms are carbon, and where the ring system is joined to the remainder of the molecule by any of the ring atoms. Examples of suitable heteroaryl groups include pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, and benzothiazolyl groups.

Examples of suitable aromatic diisocyanates for producing the polyurethane polymer chains include toluene diisocyanate (TDI), TDI adducts with trimethyloylpropane (TMP), methylene diphenyl diisocyanate (MDI), xylene diisocyanate (XDI), tetramethylxylylene diisocyanate (TMXDI), hydrogenated xylene diisocyanate (HXDI), naphthalene 1,5-diisocyanate (NDI), 1,5-tetrahydronaphthalene diisocyanate, para-phenylene diisocyanate (PPDI), 3,3'-dimethyldipheny1-4, 4'-diisocyanate (DDDI), 4,4'-dibenzyl diisocyanate (DBDI), 4-chloro-1,3-phenylene diisocyanate, and combinations thereof. The polymer chains can be substantially free of aromatic groups.

The polyurethane polymer chains can be produced from diisocyanates including HMDI, TDI, MDI, $H_{12}$ aliphatics, and combinations thereof. For example, the polyurethane can comprise one or more polyurethane polymer chains produced from diisocyanates including HMDI, TDI, MDI, $H_{12}$ aliphatics, and combinations thereof.

Polyurethane chains which are at least partially cross-linked or which can be crosslinked, can be used in accordance with the present disclosure. It is possible to produce crosslinked or crosslinkable polyurethane chains by reacting multi-functional isocyanates to form the polyurethane. Examples of suitable triisocyanates for producing the polyurethane chains include TDI, HDI, and IPDI adducts with trimethyloylpropane (TMP), uretdiones (i.e., dimerized isocyanates), polymeric MDI, and combinations thereof.

The $R_3$ group in Formula 2 can include a linear or branched group having from 2 to 10 carbon atoms, based on the particular chain extender polyol used, and can be, for example, aliphatic, aromatic, or an ether or polyether. Examples of suitable chain extender polyols for producing the polyurethane include ethylene glycol, lower oligomers of ethylene glycol (e.g., diethylene glycol, triethylene glycol, and tetraethylene glycol), 1,2-propylene glycol, 1,3-propylene glycol, lower oligomers of propylene glycol (e.g., dipropylene glycol, tripropylene glycol, and tetrapropylene glycol), 1,4-butylene glycol, 2,3-butylene glycol, 1,6-hexanediol, 1,8-octanediol, neopentyl glycol, 1,4-cyclohexanedimethanol, 2-ethyl-1,6-hexanediol, 1-methyl-1,3-propanediol, 2-methyl-1,3-propanediol, dihydroxyalkylated aromatic compounds (e.g., bis(2-hydroxyethyl) ethers of hydroquinone and resorcinol, xylene-a,a-diols, bis(2-hydroxyethyl) ethers of xylene-a,a-diols, and combinations thereof.

The $R_2$ group in Formula 1 and 2 can include a polyether group, a polyester group, a polycarbonate group, an aliphatic group, or an aromatic group. Each $R_2$ group can be present in an amount of about 5 percent to about 85 percent by weight, from about 5 percent to about 70 percent by weight, or from about 10 percent to about 50 percent by weight, based on the total weight of the reactant monomers.

At least one $R_2$ group of the polyurethane includes a polyether segment (i.e., a segment having one or more ether groups). Suitable polyether groups include, but are not limited to, polyethylene oxide (PEO), polypropylene oxide (PPO), polytetrahydrofuran (PTHF), polytetramethylene oxide (PTMO), and combinations thereof. The term "alkyl" as used herein refers to straight chained and branched saturated hydrocarbon groups containing one to thirty carbon atoms, for example, one to twenty carbon atoms, or one to ten carbon atoms. When used in association with the term $C_n$ it means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Non-limiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

In some examples of the polyurethane, the at least one $R_2$ group includes a polyester group. The polyester group can be derived from the polyesterification of one or more dihydric alcohols (e.g., ethylene glycol, 1,3-propylene glycol, 1,2-propylene glycol, 1,4-butanediol, 1,3-butanediol, 2-methylpentanediol, 1,5-diethylene glycol, 1,5-pentanediol, 1,5-hexanediol, 1,2-dodecanediol, cyclohexanedimethanol, and combinations thereof) with one or more dicarboxylic acids (e.g., adipic acid, succinic acid, sebacic acid, suberic acid, methyladipic acid, glutaric acid, pimelic acid, azelaic acid, thiodipropionic acid and citraconic acid and combinations thereof). The polyester group also can be derived from polycarbonate prepolymers, such as poly(hexamethylene carbonate) glycol, poly(propylene carbonate) glycol, poly(tetramethylene carbonate)glycol, and poly (nonanemethylene carbonate) glycol. Suitable polyesters can include, for example, polyethylene adipate (PEA), poly (1,4-butylene adipate), poly(tetramethylene adipate), poly (hexamethylene adipate), polycaprolactone, polyhexamethylene carbonate, poly(propylene carbonate), poly (tetramethylene carbonate), poly(nonanemethylene carbonate), and combinations thereof.

At least one $R_2$ group can include a polycarbonate group. The polycarbonate group can be derived from the reaction of one or more dihydric alcohols (e.g., ethylene glycol, 1,3- propylene glycol, 1,2-propylene glycol, 1,4-butanediol, 1,3-butanediol, 2-methylpentanediol 1,5-diethylene glycol, 1,5-pentanediol, 1,5-hexanediol, 1,2-dodecanediol, cyclohexanedimethanol, and combinations thereof) with ethylene carbonate.

The aliphatic group can be linear and can include, for example, an alkylene chain having from 1 to 20 carbon atoms or an alkenylene chain having from 1 to 20 carbon atoms (e.g., methylene, ethylene, propylene, butylene, pentylene, hexylene, heptylene, octylene, nonylene, decylene, undecylene, dodecylene, tridecylene, ethenylene, propenylene, butenylene, pentenylene, hexenylene, heptenylene, octenylene, nonenylene, decenylene, undecenylene, dodecenylene, tridecenylene). The term "alkene" or "alkylene" refers to a bivalent hydrocarbon. The term "alkenylene" refers to a bivalent hydrocarbon molecule or portion of a molecule having at least one double bond.

The aliphatic and aromatic groups can be substituted with one or more pendant relatively hydrophilic and/or charged groups. The pendant hydrophilic group can include one or more (e.g., 2, 3, 4, 5, 6, 7, 8, 9, 10 or more) hydroxyl groups. The pendant hydrophilic group includes one or more (e.g., 2, 3, 4, 5, 6, 7, 8, 9, 10 or more) amino groups. In some cases, the pendant hydrophilic group includes one or more (e.g., 2, 3, 4, 5, 6, 7, 8, 9, 10 or more) carboxylate groups. For example, the aliphatic group can include one or more polyacrylic acid group. In some cases, the pendant hydrophilic group includes one or more (e.g., 2, 3, 4, 5, 6, 7, 8, 9, 10 or more) sulfonate groups. In some cases, the pendant hydrophilic group includes one or more (e.g., 2, 3, 4, 5, 6, 7, 8, 9, 10 or more) phosphate groups. In some examples, the pendant hydrophilic group includes one or more ammonium groups (e.g., tertiary and/or quaternary ammonium). In other examples, the pendant hydrophilic group includes one or more zwitterionic groups (e.g., a betaine, such as poly(carboxybetaine (pCB) and ammonium phosphonate groups such as a phosphatidylcholine group).

The $R_2$ group can include charged groups that are capable of binding to a counterion to ionically crosslink the polymer and form ionomers. For example, $R_2$ is an aliphatic or aromatic group having pendant amino, carboxylate, sulfonate, phosphate, ammonium, or zwitterionic groups, or combinations thereof.

When a pendant hydrophilic group is present, the pendant hydrophilic group can be at least one polyether group, such as two polyether groups. In other cases, the pendant hydrophilic group is at least one polyester. The pendant hydrophilic group can be a polylactone group (e.g., polyvinylpyrrolidone). Each carbon atom of the pendant hydrophilic group can optionally be substituted with, e.g., an alkyl group having from 1 to 6 carbon atoms. The aliphatic and aromatic groups can be graft polymeric groups, wherein the pendant groups are homopolymeric groups (e.g., polyether groups, polyester groups, polyvinylpyrrolidone groups).

The pendant hydrophilic group can be a polyether group (e.g., a polyethylene oxide (PEO) group, a polyethylene glycol (PEG) group), a polyvinylpyrrolidone group, a polyacrylic acid group, or combinations thereof.

The pendant hydrophilic group can be bonded to the aliphatic group or aromatic group through a linker. The linker can be any bifunctional small molecule (e.g., one having from 1 to 20 carbon atoms) capable of linking the pendant hydrophilic group to the aliphatic or aromatic group. For example, the linker can include a diisocyanate group, as previously described herein, which when linked to the pendant hydrophilic group and to the aliphatic or aromatic group forms a carbamate bond. The linker can be 4,4'-diphenylmethane diisocyanate (MDI), as shown below.

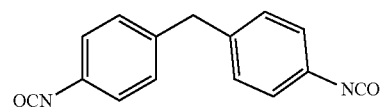

(Formula 3)

The pendant hydrophilic group can be a polyethylene oxide group and the linking group can be MDI, as shown below.

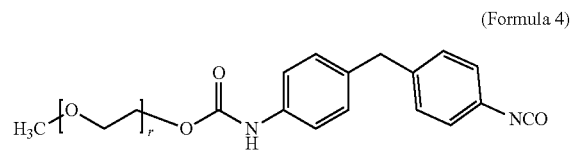

(Formula 4)

The pendant hydrophilic group can be functionalized to enable it to bond to the aliphatic or aromatic group, optionally through the linker. For example, when the pendant hydrophilic group includes an alkene group, which can undergo a Michael addition with a sulfhydryl-containing bifunctional molecule (i.e., a molecule having a second reactive group, such as a hydroxyl group or amino group), resulting in a hydrophilic group that can react with the polymer backbone, optionally through the linker, using the second reactive group. For example, when the pendant hydrophilic group is a polyvinylpyrrolidone group, it can react with the sulfhydryl group on mercaptoethanol to result in hydroxyl-functionalized polyvinylpyrrolidone, as shown below.

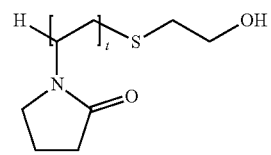

(Formula 5)

At least one $R_2$ group in the polyurethane can include a polytetramethylene oxide group. At least one $R_2$ group of the polyurethane can include an aliphatic polyol group functionalized with a polyethylene oxide group or polyvinylpyrrolidone group, such as the polyols described in E.P. Patent No. 2 462 908, which is hereby incorporated by reference. For example, the $R_2$ group can be derived from the reaction product of a polyol (e.g., pentaerythritol or 2,2,3-trihydroxypropanol) and either MDI-derivatized methoxypolyethylene glycol (to obtain compounds as shown in Formulas 6 or 7) or with MDI-derivatized polyvinylpyrrolidone (to obtain compounds as shown in Formulas 8 or 9) that had been previously been reacted with mercaptoethanol, as shown below.

(Formula 6)
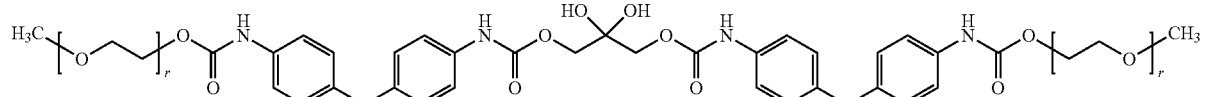

(Formula 7)
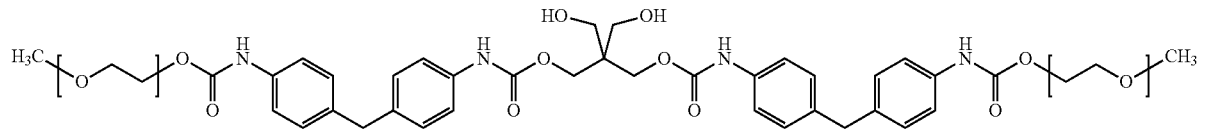

(Formula 8)
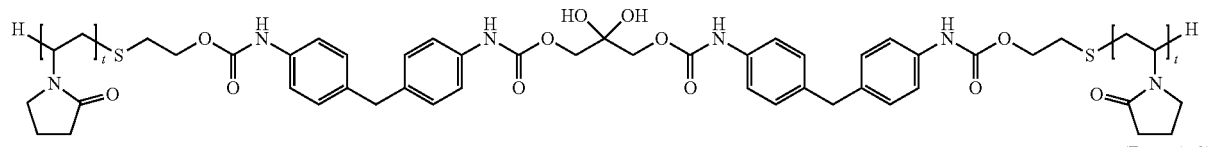

(Formula 9)
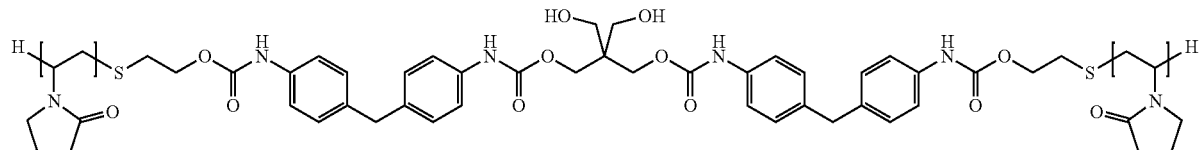

At least one $R_2$ of the polyurethane can be a polysiloxane, In these cases, the $R_2$ group can be derived from a silicone monomer of Formula 10, such as a silicone monomer disclosed in U.S. Pat. No. 5,969,076, which is hereby incorporated by reference:

(Formula 10)
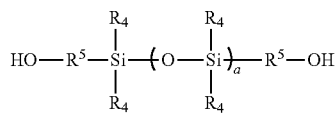

wherein: a is 1 to 10 or larger (e.g., 1, 2, 3, 4, 5, 6, 7, 8, 9, or 10); each $R_4$ independently is hydrogen, an alkyl group having from 1 to 18 carbon atoms, an alkenyl group having from 2 to 18 carbon atoms, aryl, or polyether; and each $R_5$ independently is an alkylene group having from 1 to 10 carbon atoms, polyether, or polyurethane.

Each $R_4$ group can independently be a H, an alkyl group having from 1 to 10 carbon atoms, an alkenyl group having from 2 to 10 carbon atoms, an aryl group having from 1 to 6 carbon atoms, polyethylene, polypropylene, or polybutylene group. Each $R_4$ group can independently be selected from the group consisting of methyl, ethyl, n-propyl, iso-propyl, n-butyl, isobutyl, s-butyl, t-butyl, ethenyl, propenyl, phenyl, and polyethylene groups.

Each $R_5$ group can independently include an alkylene group having from 1 to 10 carbon atoms (e.g., a methylene, ethylene, propylene, butylene, pentylene, hexylene, heptylene, octylene, nonylene, or decylene group). Each $R_5$ group can be a polyether group (e.g., a polyethylene, polypropylene, or polybutylene group). Each $R_5$ group can be a polyurethane group.

Optionally, the polyurethane can include an at least partially crosslinked polymeric network that includes polymer chains that are derivatives of polyurethane. The level of crosslinking can be such that the polyurethane retains thermoplastic properties (i.e., the crosslinked thermoplastic polyurethane can be melted and re-solidified under the processing conditions described herein). The crosslinked polyurethane can be a thermoset polymer. This crosslinked polymeric network can be produced by polymerizing one or more isocyanates with one or more polyamino compounds, polysulfhydryl compounds, or combinations thereof, as shown in Formulas 11 and 12, below:

(Formula 11)
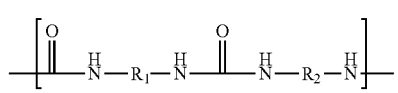

(Formula 12)
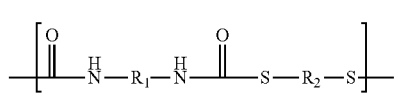

wherein the variables are as described above. Additionally, the isocyanates can also be chain extended with one or more polyamino or polythiol chain extenders to bridge two or more isocyanates, such as previously described for the polyurethanes of Formula 2.

The polyurethane chain can be physically crosslinked to another polyurethane chain through e.g., nonpolar or polar interactions between the urethane or carbamate groups of the polymers (the hard segments). The $R_1$ group in Formula 1, and the $R_1$ and $R_3$ groups in Formula 2, form the portion of the polymer often referred to as the "hard segment", and the $R_2$ group forms the portion of the polymer often referred to as the "soft segment". The soft segment is covalently bonded to the hard segment. The polyurethane having physically crosslinked hard and soft segments can be a hydrophilic polyurethane (i.e., a polyurethane, including a thermoplastic polyurethane, including hydrophilic groups as disclosed herein).

The polyurethane can be a thermoplastic polyurethane composed of MDI, PTMO, and 1,4-butylene glycol, as described in U.S. Pat. No. 4,523,005. Commercially available polyurethanes suitable for the present use include, but are not limited to those under the tradename "SANCURE" (e.g., the "SANCURE" series of polymer such as "SANCURE" 20025F) or "TECOPHILIC" (e.g., TG-500, TG-2000, SP-80A-150, SP-93A-100, SP-60D-60) (Lubrizol, Countryside, Ill., USA), "PELLETHANE" 2355-85ATP and 2355-95AE (Dow Chemical Company of Midland, Mich., USA.), "ESTANE" (e.g., ALR G 500, or 58213; Lubrizol, Countryside, Ill., USA).

One or more of the polyurethanes (e.g., those used in the primer as the coating (e.g., water-dispersible polyurethane)) can be produced by polymerizing one or more isocyanates with one or more polyols to produce copolymer chains having carbamate linkages (—N(C=O)O—) and one or more water-dispersible enhancing moieties, where the polymer chain includes one or more water-dispersible enhancing moieties (e.g., a monomer in polymer chain). The water-dispersible polyurethane can also be referred to as "a waterborne polyurethane polymer dispersion." The water-dispersible enhancing moiety can be added to the chain of Formula 1 or 2 (e.g., within the chain and/or onto the chain as a side chain). Inclusion of the water-dispersible enhancing moiety enables the formation of a water-borne polyurethane dispersion. The term "water-borne" herein means the continuous phase of the dispersion or formulation of about 50 weight percent to 100 weight percent water, about 60 weight percent to 100 weight percent water, about 70 weight percent to 100 weight percent water, or about 100 weight percent water. The term "water-borne dispersion" refers to a dispersion of a component (e.g., polymer, cross-linker, and the like) in water without co-solvents. The co-solvent can be used in the water-borne dispersion and the co-solvent can be an organic solvent. Additional detail regarding the polymers, polyurethanes, isocyantes and the polyols are provided below.

The polyurethane (e.g., a water-borne polyurethane polymer dispersion) can include one or more water-dispersible enhancing moieties. The water-dispersible enhancing moiety can have at least one hydrophilic (e.g., poly(ethylene oxide)), ionic or potentially ionic group to assist dispersion of the polyurethane, thereby enhancing the stability of the dispersions. A water-dispersible polyurethane can be formed by incorporating a moiety bearing at least one hydrophilic group or a group that can be made hydrophilic (e.g., by chemical modifications such as neutralization) into the polymer chain. For example, these compounds can be nonionic, anionic, cationic or zwitterionic or the combination thereof. In one example, anionic groups such as carboxylic acid groups can be incorporated into the chain in an inactive form and subsequently activated by a salt-forming compound, such as a tertiary amine. Other water-dispersible enhancing moieties can also be reacted into the backbone through urethane linkages or urea linkages, including lateral or terminal hydrophilic ethylene oxide or ureido units.

The water-dispersible enhancing moiety can be a one that includes carboxyl groups. Water-dispersible enhancing moiety that include a carboxyl group can be formed from hydroxy-carboxylic acids having the general formula $(HO)_x Q(COOH)_y$, where Q can be a straight or branched bivalent hydrocarbon radical containing 1 to 12 carbon atoms, and x and y can each independently be 1 to 3. Illustrative examples include dimethylolpropanoic acid (DMPA), dimethylol butanoic acid (DMBA), citric acid, tartaric acid, glycolic acid, lactic acid, malic acid, dihydroxymalic acid, dihydroxytartaric acid, and the like, and mixtures thereof.

The water-dispersible enhancing moiety can include reactive polymeric polyol components that contain pendant anionic groups that can be polymerized into the backbone to impart water dispersible characteristics to the polyurethane. Anionic functional polymeric polyols can include anionic polyester polyols, anionic polyether polyols, and anionic polycarbonate polyols, where additional detail is provided in U.S. Pat. No. 5,334,690.

The water-dispersible enhancing moiety can include a side chain hydrophilic monomer. For example, the water-dispersible enhancing moiety including the side chain hydrophilic monomer can include alkylene oxide polymers and copolymers in which the alkylene oxide groups have from 2-10 carbon atoms as shown in U.S. Pat. No. 6,897,281. Additional types of water-dispersible enhancing moieties can include thioglycolic acid, 2,6-dihydroxybenzoic acid, sulfoisophthalic acid, polyethylene glycol, and the like, and mixtures thereof. Additional details regarding water-dispersible enhancing moieties can be found in U.S. Pat. No. 7,476,705.

Polyamides

The polymer can comprise a polyamide, such as a thermoplastic polyamide, or a thermoset polyamide. The polyamide can be an elastomeric polyamide, including an elastomeric thermoplastic polyamide or an elastomeric thermoset polyamide. The polyamide can be a polyamide homopolymer having repeating polyamide segments of the same chemical structure. Alternatively, the polyamide can comprise a number of polyamide segments having different polyamide chemical structures (e.g., polyamide 6 segments, polyamide 11 segments, polyamide 12 segments, polyamide 66 segments, etc.). The polyamide segments having different chemical structure can be arranged randomly, or can be arranged as repeating blocks.

The polyamide can be a co-polyamide (i.e., a co-polymer including polyamide segments and non-polyamide segments). The polyamide segments of the co-polyamide can comprise or consist of polyamide 6 segments, polyamide 11 segments, polyamide 12 segments, polyamide 66 segments, or any combination thereof. The polyamide segments of the co-polyamide can be arranged randomly, or can be arranged as repeating segments. The polyamide segments can comprise or consist of polyamide 6 segments, or polyamide 12 segments, or both polyamide 6 segment and polyamide 12 segments. In the example where the polyamide segments of the co-polyamide include of polyamide 6 segments and polyamide 12 segments, the segments can be arranged randomly. The non-polyamide segments of the co-polyamide can comprise or consist of polyether segments, polyester segments, or both polyether segments and polyester segments. The co-polyamide can be a block co-polyamide, or can be a random co-polyamide. The copolyamide can be formed from the polycondensation of a polyamide oligomer or prepolymer with a second oligomer prepolymer to form a copolyamide (i.e., a co-polymer including polyamide segments. Optionally, the second prepolymer can be a hydrophilic prepolymer.

The polyamide can be a polyamide-containing block co-polymer. For example, the block co-polymer can have repeating hard segments, and repeating soft segments. The hard segments can comprise polyamide segments, and the soft segments can comprise non-polyamide segments. The polyamide-containing block co-polymer can be an elastomeric co-polyamide comprising or consisting of polyamide-containing block co-polymers having repeating hard segments and repeating soft segments. In block co-polymers, including block co-polymers having repeating hard segments and soft segments, physical crosslinks can be present within the segments or between the segments or both within and between the segments.

The polyamide itself, or the polyamide segment of the polyamide-containing block co-polymer can be derived from the condensation of polyamide prepolymers, such as lactams, amino acids, and/or diamino compounds with dicarboxylic acids, or activated forms thereof. The resulting polyamide segments include amide linkages (—(CO)NH—). The term "amino acid" refers to a molecule having at least one amino group and at least one carboxyl group. Each polyamide segment of the polyamide can be the same or different.

The polyamide or the polyamide segment of the polyamide-containing block co-polymer can be derived from the polycondensation of lactams and/or amino acids, and can include an amide segment having a structure shown in Formula 13, below, wherein $R_6$ group represents the portion of the polyamide derived from the lactam or amino acid.

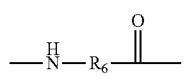

(Formula 13)

The $R_6$ group can be derived from a lactam. The $R_6$ group can be derived from a lactam group having from 3 to 20 carbon atoms, or a lactam group having from 4 to 15 carbon atoms, or a lactam group having from 6 to 12 carbon atoms. The $R_6$ group can be derived from caprolactam or laurolactam. The $R_6$ group can be derived from one or more amino acids. The $R_6$ group can be derived from an amino acid group having from 4 to 25 carbon atoms, or an amino acid group having from 5 to 20 carbon atoms, or an amino acid group having from 8 to 15 carbon atoms. The $R_6$ group can be derived from 12-aminolauric acid or 11-aminoundecanoic acid.

Optionally, in order to increase the relative degree of hydrophilicity of the polyamide-containing block co-polymer, Formula 13 can include a polyamide-polyether block copolymer segment, as shown below:

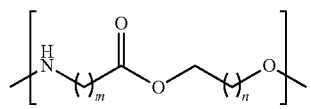

(Formula 14)

wherein m is 3-20, and n is 1-8. Optionally, m is 4-15, or 6-12 (e.g., 6, 7, 8, 9, 10, 11, or 12), and n is 1, 2, or 3. For example, m can be 11 or 12, and n can be 1 or 3. The polyamide or the polyamide segment of the polyamide-containing block co-polymer can be derived from the condensation of diamino compounds with dicarboxylic acids, or activated forms thereof, and can include an amide segment having a structure shown in Formula 15, below, wherein the $R_7$ group represents the portion of the polyamide derived from the diamino compound, and the $R_8$ group represents the portion derived from the dicarboxylic acid compound:

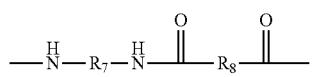

(Formula 15)

The $R_7$ group can be derived from a diamino compound that includes an aliphatic group having from 4 to 15 carbon atoms, or from 5 to 10 carbon atoms, or from 6 to 9 carbon atoms. The diamino compound can include an aromatic group, such as phenyl, naphthyl, xylyl, and tolyl. Suitable diamino compounds from which the $R_7$ group can be derived include, but are not limited to, hexamethylene diamine (HMD), tetramethylene diamine, trimethyl hexamethylene diamine (TMD), m-xylylene diamine (MXD), and 1,5-pentamine diamine. The $R_8$ group can be derived from a dicarboxylic acid or activated form thereof, including an aliphatic group having from 4 to 15 carbon atoms, or from 5 to 12 carbon atoms, or from 6 to 10 carbon atoms. The dicarboxylic acid or activated form thereof from which Re can be derived includes an aromatic group, such as phenyl, naphthyl, xylyl, and tolyl groups. Suitable carboxylic acids or activated forms thereof from which $R_8$ can be derived include adipic acid, sebacic acid, terephthalic acid, and isophthalic acid. The polyamide chain can be substantially free of aromatic groups.

Each polyamide segment of the polyamide (including the polyamide-containing block co-polymer) can be independently derived from a polyamide prepolymer selected from the group consisting of 12-aminolauric acid, caprolactam, hexamethylene diamine and adipic acid.

The polyamide can comprise or consist essentially of a poly(ether-block-amide). The poly(ether-block-amide) can be formed from the polycondensation of a carboxylic acid terminated polyamide prepolymer and a hydroxyl terminated polyether prepolymer to form a poly(ether-block-amide), as shown in Formula 16:

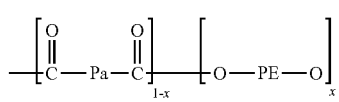

(Formula 16)

The poly(ether block amide) polymer can be prepared by polycondensation of polyamide blocks containing reactive ends with polyether blocks containing reactive ends. Examples include: 1) polyamide blocks containing diamine chain ends with polyoxyalkylene blocks containing carboxylic chain ends; 2) polyamide blocks containing dicarboxylic chain ends with polyoxyalkylene blocks containing diamine chain ends obtained by cyanoethylation and hydrogenation of aliphatic dihydroxylated alpha-omega polyoxyalkylenes known as polyether diols; 3) polyamide blocks containing dicarboxylic chain ends with polyether diols, the products obtained in this particular case being polyetheresteramides. The polyamide block of the poly(ether-block-amide) can be derived from lactams, amino acids, and/or diamino compounds with dicarboxylic acids as previously described. The polyether block can be derived from one or more polyethers selected from the group consisting of polyethylene oxide (PEO), polypropylene oxide (PPO), polytetrahydrofuran (PTHF), polytetramethylene oxide (PTMO), and combinations thereof.

The poly(ether block amide) polymers can include those comprising polyamide blocks comprising dicarboxylic chain ends derived from the condensation of α, ω-aminocarboxylic acids, of lactams or of dicarboxylic acids and diamines in the presence of a chain-limiting dicarboxylic acid. In poly(ether block amide) polymers of this type, a α, ω-aminocarboxylic acid such as aminoundecanoic acid can be used; a lactam such as caprolactam or lauryllactam can be used; a dicarboxylic acid such as adipic acid, decanedioic acid or dodecanedioic acid can be used; and a diamine such as hexamethylenediamine can be used; or various combinations of any of the foregoing. The copolymer can comprise polyamide blocks comprising polyamide 12 or of polyamide 6.

The poly(ether block amide) polymers can include those comprising polyamide blocks derived from the condensation of one or more α, ω-aminocarboxylic acids and/or of one or more lactams containing from 6 to 12 carbon atoms in the presence of a dicarboxylic acid containing from 4 to 12 carbon atoms, and are of low mass, i.e., they have a number-average molecular weight of from 400 to 1000. In poly(ether block amide) polymers of this type, an α, ω-aminocarboxylic acid such as aminoundecanoic acid or aminododecanoic acid can be used; a dicarboxylic acid such as adipic acid, sebacic acid, isophthalic acid, butanedioic acid, 1,4-cyclohexyldicarboxylic acid, terephthalic acid, the sodium or lithium salt of sulphoisophthalic acid, dimerized fatty acids (these dimerized fatty acids have a dimer content of at least 98 weight percent and are preferably hydrogenated) and dodecanedioic acid HOOC—$(CH_2)_{10}$—COOH can be used; and a lactam such as caprolactam and lauryllactam can be used; or various combinations of any of the foregoing. The copolymer can comprise polyamide blocks obtained by condensation of lauryllactam in the presence of adipic acid or dodecanedioic acid and with a number average molecular weight of at least 750 have a melting temperature of from about 127 to about 130 degrees C. The various constituents of the polyamide block and their proportion can be chosen in order to obtain a melting point of less than 150 degrees C., or from about 90 degrees C. to about 135 degrees C.

The poly(ether block amide) polymers can include those comprising polyamide blocks derived from the condensation of at least one α, ω-aminocarboxylic acid (or a lactam), at least one diamine and at least one dicarboxylic acid. In copolymers of this type, a α,ω-aminocarboxylic acid, the lactam and the dicarboxylic acid can be chosen from those described herein above and the diamine such as an aliphatic diamine containing from 6 to 12 atoms and can be acyclic and/or saturated cyclic such as, but not limited to, hexamethylenediamine, piperazine, 1-aminoethylpiperazine, bisaminopropylpiperazine, tetramethylenediamine, octamethylene-diamine, decamethylenediamine, dodecamethylenediamine, 1,5-diaminohexane, 2,2,4-trimethyl-1,6-diaminohexane, diamine polyols, isophoronediamine (IPD), methylpentamethylenediamine (MPDM), bis(aminocyclohexyl)methane (BACM) and bis(3-methyl-4-aminocyclohexyl)methane (BMACM) can be used.

The polyamide can be a thermoplastic polyamide and the constituents of the polyamide block and their proportion can be chosen in order to obtain a melting temperature of less than 150 degrees C., such as a melting point of from about 90 degrees C. to about 135 degrees C. The various constituents of the thermoplastic polyamide block and their proportion can be chosen in order to obtain a melting point of less than 150 degrees C., such as from about and 90 degrees C. to about 135 degrees C.

The number average molar mass of the polyamide blocks can be from about 300 grams per mole to about 15,000 grams per mole, from about 500 grams per mole to about 10,000 grams per mole, from about 500 grams per mole to about 6,000 grams per mole, from about 500 grams per mole to about 5,000 grams per mole, or from about 600 grams per mole to about 5,000 grams per mole. The number average molecular weight of the polyether block can range from about 100 to about 6,000, from about 400 to about 3000, or from about 200 to about 3,000. The polyether (PE) content (x) of the poly(ether block amide) polymer can be from about 0.05 to about 0.8 (i.e., from about 5 mole percent to about 80 mole percent). The polyether blocks can be present in the polyamide in an amount of from about 10 weight percent to about 50 weight percent, from about 20 weight percent to about 40 weight percent, or from about 30 weight percent to about 40 weight percent. The polyamide blocks can be present in the polyamide in an amount of from about 50 weight percent to about 90 weight percent, from about 60 weight percent to about 80 weight percent, or from about 70 weight percent to about 90 weight percent.

The polyether blocks can contain units other than ethylene oxide units, such as, for example, propylene oxide or polytetrahydrofuran (which leads to polytetramethylene glycol sequences). It is also possible to use simultaneously PEG blocks, i.e., those consisting of ethylene oxide units, polypropylene glycol (PPG) blocks, i.e. those consisting of propylene oxide units, and poly(tetramethylene ether)glycol (PTMG) blocks, i.e. those consisting of tetramethylene glycol units, also known as polytetrahydrofuran. PPG or PTMG blocks are advantageously used. The amount of polyether blocks in these copolymers containing polyamide and polyether blocks can be from about 10 weight percent to about 50 weight percent of the copolymer, or from about 35 weight percent to about 50 weight percent.

The copolymers containing polyamide blocks and polyether blocks can be prepared by any means for attaching the polyamide blocks and the polyether blocks. In practice, two processes are essentially used, one being a 2-step process and the other a one-step process.

In the two-step process, the polyamide blocks having dicarboxylic chain ends are prepared first, and then, in a second step, these polyamide blocks are linked to the polyether blocks. The polyamide blocks having dicarboxylic chain ends are derived from the condensation of polyamide precursors in the presence of a chain-stopper dicarboxylic acid. If the polyamide precursors are only lactams or α,ω-aminocarboxylic acids, a dicarboxylic acid is added. If the precursors already comprise a dicarboxylic acid, this is used in excess with respect to the stoichiometry of the diamines. The reaction usually takes place from about 180 to about 300 degrees C., such as from about 200 degrees to about 290 degrees C., and the pressure in the reactor can be set from about 5 to about 30 bar and maintained for approximately 2 to 3 hours. The pressure in the reactor is slowly reduced to atmospheric pressure and then the excess water is distilled off, for example for one or two hours.

Once the polyamide having carboxylic acid end groups has been prepared, the polyether, the polyol and a catalyst are then added. The total amount of polyether can be divided and added in one or more portions, as can the catalyst. The polyether is added first and the reaction of the OH end groups of the polyether and of the polyol with the COOH end groups of the polyamide starts, with the formation of ester linkages and the elimination of water. Water is removed as much as possible from the reaction mixture by distillation and then the catalyst is introduced in order to complete the linking of the polyamide blocks to the polyether blocks. This second step takes place with stirring, preferably under a vacuum of at least 50 millibar (5000 Pascals) at a temperature such that the reactants and the copolymers obtained are in the molten state. By way of example, this temperature can be from about 100 to about 400 degrees C., such as from about 200 to about 250 degrees C. The reaction is monitored by measuring the torque exerted by the polymer melt on the stirrer or by measuring the electric power consumed by the stirrer. The end of the reaction is determined by the value of the torque or of the target power. The catalyst is defined as being any product which promotes the linking of the polyamide blocks to the polyether blocks by esterification. The catalyst can be a derivative of a metal (M) chosen from the group formed by titanium, zirconium and hafnium. The derivative can be prepared from a tetraalkoxides consistent with the general formula M(OR)$_4$, in which M represents titanium, zirconium or hafnium and R, which can be identical or different, represents linear or branched alkyl radicals having from 1 to 24 carbon atoms.

The catalyst can comprise a salt of the metal (M), particularly the salt of (M) and of an organic acid and the complex salts of the oxide of (M) and/or the hydroxide of (M) and an organic acid. The organic acid can be formic acid, acetic acid, propionic acid, butyric acid, valeric acid, caproic acid, caprylic acid, lauric acid, myristic acid, palmitic acid, stearic acid, oleic acid, linoleic acid, linolenic acid, cyclohexanecarboxylic acid, phenylacetic acid, benzoic acid, salicylic acid, oxalic acid, malonic acid, succinic acid, glutaric acid, adipic acid, maleic acid, fumaric acid, phthalic acid or crotonic acid. The organic acid can be an acetic acid or a propionic acid. M can be zirconium and such salts are called zirconyl salts, e.g., the commercially available product sold under the name zirconyl acetate.

The weight proportion of catalyst can vary from about 0.01 to about 5 percent of the weight of the mixture of the dicarboxylic polyamide with the polyetherdiol and the polyol. The weight proportion of catalyst can vary from about 0.05 to about 2 percent of the weight of the mixture of the dicarboxylic polyamide with the polyetherdiol and the polyol.

In the one-step process, the polyamide precursors, the chain stopper and the polyether are blended together; what is then obtained is a polymer having essentially polyether blocks and polyamide blocks of highly variable length, but also the various reactants that have reacted randomly, which are distributed randomly along the polymer chain. They are the same reactants and the same catalyst as in the two-step process described above. If the polyamide precursors are only lactams, it is advantageous to add a little water. The copolymer has essentially the same polyether blocks and the same polyamide blocks, but also a small portion of the various reactants that have reacted randomly, which are distributed randomly along the polymer chain. As in the first step of the two-step process described above, the reactor is closed and heated, with stirring. The pressure established is from about 5 to about 30 bar. When the pressure no longer changes, the reactor is put under reduced pressure while still maintaining vigorous stirring of the molten reactants. The reaction is monitored as previously in the case of the two-step process.

The proper ratio of polyamide to polyether blocks can be found in a single poly(ether block amide), or a blend of two or more different composition poly(ether block amide)s can be used with the proper average composition. It can be useful to blend a block copolymer having a high level of polyamide groups with a block copolymer having a higher level of polyether blocks, to produce a blend having an average level of polyether blocks of about 20 to about 40 weight percent of the total blend of poly(amid-block-ether) copolymers, or about 30 to about 35 weight percent. The copolymer can comprise a blend of two different poly(ether-block-amide)s comprising at least one block copolymer having a level of polyether blocks below 35 weight percent, and a second poly(ether-block-amide) having at least 45 weight percent of polyether blocks.

Exemplary commercially available copolymers include, but are not limited to, those available under the tradenames of "VESTAMID" (Evonik Industries, Essen, Germany); "PLATAMID" (Arkema, Colombes, France), e.g., product code H2694; "PEBAX" (Arkema), e.g., product code "PEBAX MH1657" and "PEBAX MV1074"; "PEBAX RNEW" (Arkema); "GRILAMID" (EMS-Chemie AG, Domat-Ems, Switzerland), or also to other similar materials produced by various other suppliers.

The polyamide can be physically crosslinked through, e.g., nonpolar or polar interactions between the polyamide groups of the polymers. In examples where the polyamide is a copolyamide, the copolyamide can be physically crosslinked through interactions between the polyamide groups, and optionally by interactions between the copolymer groups. When the co-polyamide is physically crosslinked through interactions between the polyamide groups, the polyamide segments can form the portion of the polymer referred to as the hard segment, and copolymer segments can form the portion of the polymer referred to as the soft segment. For example, when the copolyamide is a poly (ether-block-amide), the polyamide segments form the hard segments of the polymer, and polyether segments form the soft segments of the polymer. Therefore, in some examples, the polymer can include a physically crosslinked polymeric network having one or more polymer chains with amide linkages.

The polyamide segment of the co-polyamide can include polyamide-11 or polyamide-12 and the polyether segment can be a segment selected from the group consisting of polyethylene oxide, polypropylene oxide, and polytetramethylene oxide segments, and combinations thereof.

The polyamide can be partially or fully covalently crosslinked, as previously described herein. In some cases, the degree of crosslinking present in the polyamide is such that, when it is thermally processed, e.g., in the form of a yarn or fiber to form the articles of the present disclosure, the partially covalently crosslinked thermoplastic polyamide retains sufficient thermoplastic character that the partially covalently crosslinked thermoplastic polyamide is melted during the processing and re-solidifies. In other cases, the crosslinked polyamide is a thermoset polymer.

Polyesters

The polymers can comprise a polyester. The polyester can comprise a thermoplastic polyester, or a thermoset polyester. Additionally, the polyester can be an elastomeric polyester, including a thermoplastic polyester or a thermoset elastomeric polyester. The polyester can be formed by reaction of one or more carboxylic acids, or its ester-forming derivatives, with one or more bivalent or multivalent aliphatic, alicyclic, aromatic or araliphatic alcohols or a bisphenol. The polyester can be a polyester homopolymer having repeating polyester segments of the same chemical structure. Alternatively, the polyester can comprise a number of polyester segments having different polyester chemical structures (e.g., polyglycolic acid segments, polylactic acid segments, polycaprolactone segments, polyhydroxyalkanoate segments, polyhydroxybutyrate segments, etc.). The polyester segments having different chemical structure can be arranged randomly, or can be arranged as repeating blocks.

Exemplary carboxylic acids that can be used to prepare a polyester include, but are not limited to, adipic acid, pimelic acid, suberic acid, azelaic acid, sebacic acid, nonane dicarboxylic acid, decane dicarboxylic acid, undecane dicarboxylic acid, terephthalic acid, isophthalic acid, alkyl-substituted or halogenated terephthalic acid, alkyl-substituted or halogenated isophthalic acid, nitro-terephthalic acid, 4,4'-diphenyl ether dicarboxylic acid, 4,4'-diphenyl thioether dicarboxylic acid, 4,4'-diphenyl sulfone-dicarboxylic acid, 4,4'-diphenyl alkylenedicarboxylic acid, naphthalene-2,6-dicarboxylic acid, cyclohexane-1,4-dicarboxylic acid and cyclohexane-1,3-dicarboxylic acid. Exemplary diols or phenols suitable for the preparation of the polyester include, but are not limited to, ethylene glycol, diethylene glycol, 1,3-propanediol, 1,4-butanediol, 1,6-hexanediol, 1,8-octanediol, 1,10-decanediol, 1,2-propanediol, 2,2-dimethyl-1,3-propanediol, 2,2,4-trimethyihexanediol, p-xylenediol, 1,4-cyclohexanediol, 1,4-cyclohexane dimethanol, and bis-phenol A.

The polyester can be a polybutylene terephthalate (PBT), a polytrimethylene terephthalate, a polyhexamethylene terephthalate, a poly-1,4-dimethylcyclohexane terephthalate, a polyethylene terephthalate (PET), a polyethylene isophthalate (PEI), a polyarylate (PAR), a polybutylene naphthalate (PBN), a liquid crystal polyester, or a blend or mixture of two or more of the foregoing.

The polyester can be a co-polyester (i.e., a co-polymer including polyester segments and non-polyester segments). The co-polyester can be an aliphatic co-polyester (i.e., a co-polyester in which both the polyester segments and the non-polyester segments are aliphatic). Alternatively, the co-polyester can include aromatic segments. The polyester segments of the co-polyester can comprise or consist essentially of polyglycolic acid segments, polylactic acid segments, polycaprolactone segments, polyhydroxyalkanoate segments, polyhydroxybutyrate segments, or any combination thereof. The polyester segments of the co-polyester can be arranged randomly, or can be arranged as repeating blocks.

For example, the polyester can be a block co-polyester having repeating blocks of polymeric units of the same chemical structure which are relatively harder (hard segments), and repeating blocks of the same chemical structure which are relatively softer (soft segments). In block co-polyesters, including block co-polyesters having repeating hard segments and soft segments, physical crosslinks can be present within the blocks or between the blocks or both within and between the blocks. The polymer can comprise or consist essentially of an elastomeric co-polyester having repeating blocks of hard segments and repeating blocks of soft segments.

The non-polyester segments of the co-polyester can comprise or consist essentially of polyether segments, polyamide segments, or both polyether segments and polyamide segments. The co-polyester can be a block co-polyester, or can be a random co-polyester.

The co-polyester can be formed from the polycondensation of a polyester oligomer or prepolymer with a second oligomer prepolymer to form a block copolyester. Optionally, the second prepolymer can be a hydrophilic prepolymer. For example, the co-polyester can be formed from the polycondensation of terephthalic acid or naphthalene dicarboxylic acid with ethylene glycol, 1,4-butanediol, or 1,3-propanediol. Examples of co-polyesters include polyethylene adipate, polybutylene succinate, poly(3-hydroxybutyrate-co-3-hydroxyvalerate), polyethylene terephthalate, polybutylene terephthalate, polytrimethylene terephthalate, polyethylene napthalate, and combinations thereof. The co-polyamide can comprise or consist of polyethylene terephthalate.

The polyester can be a block copolymer comprising segments of one or more of polybutylene terephthalate (PBT), a polytrimethylene terephthalate, a polyhexamethylene terephthalate, a poly-1,4-dimethylcyclohexane terephthalate, a polyethylene terephthalate (PET), a polyethylene isophthalate (PEI), a polyarylate (PAR), a polybutylene naphthalate (PBN), and a liquid crystal polyester. For example, a suitable polyester that is a block copolymer can be a PET/PEI copolymer, a polybutylene terephthalate/tetraethylene glycol copolymer, a polyoxyalkylenediimide diacid/polybutylene terephthalate copolymer, or a blend or mixture of any of the foregoing.

The polyester can be a biodegradable resin, for example, a copolymerized polyester in which poly(α-hydroxy acid) such as polyglycolic acid or polylactic acid is contained as principal repeating units.

The disclosed polyesters can be prepared by a variety of polycondensation methods known to the skilled artisan, such as a solvent polymerization or a melt polymerization process.

Polyolefins

The polymers can comprise or consist essentially of a polyolefin. The polyolefin can be a thermoplastic polyolefin or a thermoset polyolefin. Additionally, the polyolefin can be an elastomeric polyolefin, including a thermoplastic elastomeric polyolefin or a thermoset elastomeric polyolefin. Exemplary polyolefins can include polyethylene, polypropylene, and olefin elastomers (e.g., metallocene-catalyzed block copolymers of ethylene and α-olefins having 4 to about 8 carbon atoms). The polyolefin can be a polymer comprising a polyethylene, an ethylene-α-olefin copolymer, an ethylene-propylene rubber (EPDM), a polybutene, a polyisobutylene, a poly-4-methylpent-1-ene, a polyisoprene, a polybutadiene, a ethylene-methacrylic acid copolymer, and an olefin elastomer such as a dynamically cross-linked polymer obtained from polypropylene (PP) and an ethylene-propylene rubber (EPDM), and blends or mixtures of the foregoing. Further exemplary polyolefins include polymers of cycloolefins such as cyclopentene or norbornene.

It is to be understood that polyethylene, which optionally can be crosslinked, is inclusive a variety of polyethylenes, including low density polyethylene (LDPE), linear low density polyethylene (LLDPE), (VLDPE) and (ULDPE), medium density polyethylene (MDPE), high density polyethylene (HDPE), high density and high molecular weight polyethylene (HDPE-HMW), high density and ultrahigh molecular weight polyethylene (HDPE-UHMW), and blends or mixtures of any the foregoing polyethylenes. A polyethylene can also be a polyethylene copolymer derived from monomers of monolefins and diolefins copolymerized with a vinyl, acrylic acid, methacrylic acid, ethyl acrylate, vinyl alcohol, and/or vinyl acetate. Polyolefin copolymers comprising vinyl acetate-derived units can be a high vinyl acetate content copolymer, e.g., greater than about 50 weight percent vinyl acetate-derived composition.

The polyolefin can be formed through free radical, cationic, and/or anionic polymerization by methods well known to those skilled in the art (e.g., using a peroxide initiator, heat, and/or light). The disclosed polyolefin can be prepared by radical polymerization under high pressure and at elevated temperature. Alternatively, the polyolefin can be prepared by catalytic polymerization using a catalyst that normally contains one or more metals from group IVb, Vb, VIb or VIII metals. The catalyst usually has one or more than one ligand, typically oxides, halides, alcoholates, esters, ethers, amines, alkyls, alkenyls and/or aryls that can be either p- or s-coordinated complexed with the group IVb, Vb, VIb or VIII metal. The metal complexes can be in the free form or fixed on substrates, typically on activated magnesium chloride, titanium(III) chloride, alumina or silicon oxide. The metal catalysts can be soluble or insoluble in the polymerization medium. The catalysts can be used by themselves in the polymerization or further activators can be used, typically a group Ia, IIa and/or IIIa metal alkyls, metal hydrides, metal alkyl halides, metal alkyl oxides or metal alkyloxanes. The activators can be modified conveniently with further ester, ether, amine or silyl ether groups.

Suitable polyolefins can be prepared by polymerization of monomers of monolefins and diolefins as described herein. Exemplary monomers that can be used to prepare the polyolefin include, but are not limited to, ethylene, propylene, 1-butene, 1-pentene, 1-hexene, 2-methyl-1-propene, 3-methyl-1-pentene, 4-methyl-1-pentene, 5-methyl-1-hexene and mixtures thereof.

Suitable ethylene-α-olefin copolymers can be obtained by copolymerization of ethylene with an α-olefin such as propylene, butene-1, hexene-1, octene-1,4-methyl-1-pentene or the like having carbon numbers of 3 to 12.

Suitable dynamically cross-linked polymers can be obtained by cross-linking a rubber component as a soft segment while at the same time physically dispersing a hard segment such as PP and a soft segment such as EPDM by using a kneading machine such as a Banbury mixer and a biaxial extruder.

The polyolefin can be a mixture of polyolefins, such as a mixture of two or more polyolefins disclosed herein above. For example, a suitable mixture of polyolefins can be a mixture of polypropylene with polyisobutylene, polypropylene with polyethylene (for example PP/HDPE, PP/LDPE) or mixtures of different types of polyethylene (for example LDPE/HDPE).

The polyolefin can be a copolymer of suitable monolefin monomers or a copolymer of a suitable monolefin monomer and a vinyl monomer. Exemplary polyolefin copolymers include ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

The polyolefin can be a polypropylene homopolymer, a polypropylene copolymers, a polypropylene random copolymer, a polypropylene block copolymer, a polyethylene homopolymer, a polyethylene random copolymer, a polyethylene block copolymer, a low density polyethylene (LDPE), a linear low density polyethylene (LLDPE), a medium density polyethylene, a high density polyethylene (HDPE), or blends or mixtures of one or more of the preceding polymers.

The polyolefin can be a polypropylene. The term "polypropylene," as used herein, is intended to encompass any polymeric composition comprising propylene monomers, either alone or in mixture or copolymer with other randomly selected and oriented polyolefins, dienes, or other monomers (such as ethylene, butylene, and the like). Such a term also encompasses any different configuration and arrangement of the constituent monomers (such as atactic, syndiotactic, isotactic, and the like). Thus, the term as applied to fibers is intended to encompass actual long strands, tapes, threads, and the like, of drawn polymer. The polypropylene can be of any standard melt flow (by testing); however, standard fiber grade polypropylene resins possess ranges of Melt Flow Indices between about 1 and 1000.

The polyolefin can be a polyethylene. The term "polyethylene," as used herein, is intended to encompass any polymeric composition comprising ethylene monomers, either alone or in mixture or copolymer with other randomly selected and oriented polyolefins, dienes, or other monomers (such as propylene, butylene, and the like). Such a term also encompasses any different configuration and arrangement of the constituent monomers (such as atactic, syndiotactic, isotactic, and the like). Thus, the term as applied to fibers is intended to encompass actual long strands, tapes, threads, and the like, of drawn polymer.

The polyethylene can be of any standard melt flow (by testing); however, standard fiber grade polyethylene resins possess ranges of Melt Flow Indices between about 1 and 1000.

The thermoplastic and/or thermosetting material can further comprise one or more processing aids. The processing aid can be a non-polymeric material. These processing aids can be independently selected from the group including, but not limited to, curing agents, initiators, plasticizers, mold release agents, lubricants, antioxidants, flame retardants, dyes, pigments, reinforcing and non-reinforcing fillers, fiber reinforcements, and light stabilizers.

Now having described various aspects of the present disclosure, additional discussion is provided regarding the structure of the bladder. The bladder can be unfilled, partially inflated, or fully inflated when the structural design (e.g., multi-layer optical film) is disposed onto the bladder. The bladder is a bladder capable of including a volume of a fluid. An unfilled bladder is a fluid-fillable bladder and a filled bladder that has been at least partially inflated with a fluid at a pressure equal to or greater than atmospheric pressure.

When disposed onto or incorporated into an article of footwear, apparel, or sports equipment, the bladder is generally, at that point, a fluid-filled bladder. The fluid be a gas or a liquid. The gas can include air, nitrogen gas ($N_2$), or other appropriate gas.

The bladder can have a gas transmission rate for nitrogen gas, for example, where a bladder wall of a given thickness has a gas transmission rate for nitrogen that is at least about ten times lower than the gas transmission rate for nitrogen of a butyl rubber layer of substantially the same thickness as the thickness of the bladder described herein. The bladder can have a first bladder wall having a first bladder wall thickness (e.g., about 0.1 to 40 mils). The bladder can have a first bladder wall that can have a gas transmission rate (GTR) for nitrogen gas of less than about 15 $cm^3/m^2 \cdot atm \cdot day$, less than about 10 $m^3/m^2 \cdot atm \cdot day$, less than about 5 $cm^3/m^2 \cdot atm \cdot day$, less than about 1 $cm^3/m^2 \cdot atm \cdot day$ (e.g., from about 0.001 $cm^3/m^2 \cdot atm \cdot day$ to about 1 $cm^3/m^2 \cdot atm \cdot day$, about 0.01 $cm^3/m^2 \cdot atm \cdot day$ to about 1 $cm^3/m^2 \cdot atm \cdot day$ or about 0.1 $cm^3/m^2 \cdot atm \cdot day$ to about 1 $cm^3/m^2 \cdot atm \cdot day$) for an average wall thickness of 20 mils. The bladder can have a first bladder wall having a first bladder wall thickness, where the first bladder wall has a gas transmission rate of 15 cm$^3$/m$^2$·atm·day or less for nitrogen for an average wall thickness of 20 mils.

In an aspect, the bladder has a bladder wall having an interior-facing side and an exterior-facing side, where the interior-facing side defines at least a portion of an interior region of the bladder. The multi-layer optical film having a first side and a second opposing side can be disposed on the exterior-facing side of the bladder, the interior-facing side of the bladder, or both. The exterior-facing side of the bladder, the interior-facing side of the bladder, or both can include a plurality of topographical structures extending from the exterior-facing side of the bladder wall, the interior-facing side of the bladder, or both, where the first side or the second side of the multi-layer optical film is disposed on the exterior-facing side of the bladder wall and covering some or all of the plurality of topographical structures, the interior-facing side of the bladder wall and covering some or all of the plurality of topographical structures, or both, and wherein the multi-layer optical film imparts a structural color to the bladder wall. The primer layer can be disposed on the exterior-facing side of the bladder, the interior-facing side of the bladder, or both, between the bladder wall and the multi-layer optical film.

In a particular aspect, the bladder can include a top wall operably secured to the footwear upper, a bottom wall opposite the top wall, and one or more sidewalls extending between the top wall and the bottom wall of the inflated bladder. The top wall, the bottom wall, and the one or more sidewalls collectively define an interior region of the inflated bladder, and wherein the one or more sidewalls each comprise an exterior-facing side. The multi-layer optical film having a first side and a second opposing side can be disposed on the exterior-facing side of the bladder, the interior-facing side of the bladder, or both. The exterior-facing side of the bladder, the interior-facing side of the bladder, or both can include a plurality of topographical structures extending from the exterior-facing side of the bladder wall, the interior-facing side of the bladder, or both, where the first side or the second side of the multi-layer optical film is disposed on the exterior-facing side of the bladder wall and covering some or all of the plurality of topographical structures, the interior-facing side of the bladder wall and covering some or all of the plurality of topographical structures, or both, and wherein the multi-layer optical film imparts a structural color to the bladder wall. The primer layer can be disposed on the exterior-facing side of the bladder, the interior-facing side of the bladder, or both, between the bladder wall and the multi-layer optical film.

An accepted method for measuring the relative permeance, permeability, and diffusion of inflated bladders is ASTM D-1434-82-V. See, e.g., U.S. Pat. No. 6,127,026, which is incorporated by reference as if fully set forth herein. According to ASTM D-1434-82-V, permeance, permeability and diffusion are measured by the following formulae:

Permeance (quantity of gas)/[(area)×(time)×(pressure difference)]=permeance (GTR)/(pressure difference)= cm$^3$/m$^2$·atm·day (i.e., 24 hours)

Permeability

[(quantity of gas)×(film thickness)][(area)×(time)× (pressure difference)]=permeability [(GTR)× (film thickness)]/(pressure difference)=[(cm$^3$) (mil)]/m$^2$·atm·day (i.e., 24 hours)

Diffusion at One Atmosphere (quantity of gas)/[(area)×(time)]=GTR=cm$^3$/m$^2$·day (i.e., 24 hours)

The bladder can include a bladder wall that includes a film including at least one polymeric layer or at least two or more polymeric layers. Each of the polymeric layers can be about 0.1 to 40 mils in thickness.

The polymeric layer can be formed of polymer material such as a thermoplastic material as described above and herein. The thermoplastic material can include an elastomeric material, such as a thermoplastic elastomeric material. The thermoplastic materials can include thermoplastic polyurethane (TPU), such as those described above and herein. The thermoplastic materials can include polyester-based TPU, polyether-based TPU, polycaprolactone-based TPU, polycarbonate-based TPU, polysiloxane-based TPU, or combinations thereof. Non-limiting examples of thermoplastic material that can be used include: "PELLETHANE" 2355-85ATP and 2355-95AE (Dow Chemical Company of Midland, Mich., USA), "ELASTOLLAN" (BASF Corporation, Wyandotte, Mich., USA) and "ESTANE" (Lubrizol, Brecksville, Ohio, USA), all of which are either ester or ether based. Additional thermoplastic material can include those described in U.S. Pat. Nos. 5,713,141; 5,952,065; 6,082,025; 6,127,026; 6,013,340; 6,203,868; and 6,321,465, which are incorporated herein by reference.

The polymeric layer can be formed of one or more of the following: ethylene-vinyl alcohol copolymers (EVOH), poly(vinyl chloride), polyvinylidene polymers and copolymers (e.g., polyvinylidene chloride), polyamides (e.g., amorphous polyamides), acrylonitrile polymers (e.g., acrylonitrile-methyl acrylate copolymers), polyurethane engineering plastics, polymethylpentene resins, ethylene-carbon monoxide copolymers, liquid crystal polymers, polyethylene terephthalate, polyether imides, polyacrylic imides, and other polymeric materials known to have relatively low gas transmission rates. Blends and alloys of these materials as well as with the TPUs described herein and optionally including combinations of polyimides and crystalline polymers, are also suitable. For instance, blends of polyimides and liquid crystal polymers, blends of polyamides and polyethylene terephthalate, and blends of polyamides with styrenics are suitable.

Specific examples of polymeric materials of the polymeric layer can include acrylonitrile copolymers such as "BAREX" resins, available from Ineos (Rolle, Switzerland); polyurethane engineering plastics such as "ISPLAST" ETPU available from Lubrizol (Brecksville, Ohio, USA); ethylene-vinyl alcohol copolymers marketed under the tradenames "EVAL" by Kuraray (Houston, Tex., USA), "SOARNOL" by Nippon Gohsei (Hull, England), and "SELAR OH" by DuPont (Wilmington, Del., USA); polyvinylidiene chloride available from S.C. Johnson (Racine, Wis., USA) under the tradename "SARAN", and from Solvay (Brussels, Belgium) under the tradename "IXAN"; liquid crystal polymers such as "VECTRA" from Celanese (Irving, Tex., USA) and "XYDAR" from Solvay; "MDX6" nylon, and amorphous nylons such as "NOVAMID" X21 from Koninklijke DSM N.V (Heerlen, Netherlands), "SELAR PA" from DuPont; polyetherimides sold under the tradename "ULTEM" by SABIC (Riyadh, Saudi Arabia); poly(vinyl alcohol)s; and polymethylpentene resins available from Mitsui Chemicals (Tokyo, Japan) under the tradename "TPX".

Each polymeric layer of the film can be formed of a thermoplastic material which can include a combination of thermoplastic polymers. In addition to one or more thermoplastic polymers, the thermoplastic material can optionally include a colorant, a filler, a processing aid, a free radical scavenger, an ultraviolet light absorber, and the like. Each polymeric layer of the film can be made of a different of thermoplastic material including a different type of thermoplastic polymer.

The bladder can be made by applying heat, pressure and/or vacuum to a film. The bladder (e.g., one or more polymeric layers) can be formed using one or more polymeric materials, and forming the bladder using one or more processing techniques including, for example, extrusion, blow molding, injection molding, vacuum molding, rotary molding, transfer molding, pressure forming, heat sealing, casting, low-pressure casting, spin casting, reaction injection molding, radio frequency (RF) welding, and the like. The bladder can be made by co-extrusion followed by heat sealing or welding to give an inflatable bladder, which can optionally include one or more valves (e.g., one way valves) that allows the bladder to be filled with the fluid (e.g., gas).

As described herein, the multi-layer optical film can be disposed onto the interior-facing surface (side) of the bladder or the exterior-facing surface (side) of the bladder. The textured layer can be the interior-facing surface (side) or the exterior-facing surface (side) of the bladder. The multi-layer optical film can include the optical layer and optionally the primer layer and texture structure. The textured layer can be the interior-facing surface (side) or the exterior-facing surface (side) of the bladder (e.g., where the interior-facing or exterior-facing side is made of a thermoplastic material) and the primer layer disposed thereon and the multi-layer optical film disposed on the primer layer.

Now having described embodiments of the disclosure, evaluation of various properties and characteristics described herein are by various testing procedures as described herein below.

Method to Determine the Melting Temperature, and Glass Transition Temperature.

The melting temperature and glass transition temperature are determined using a commercially available Differential Scanning Calorimeter ('DSC') in accordance with ASTM D3418-97. Briefly, a 10-15 gram sample is placed into an aluminum DSC pan and then the lead was sealed with the crimper press. The DSC is configured to scan from −100 degrees C. to 225 degrees C. with a 20 degrees C./minute heating rate, hold at 225 degrees C. for 2 minutes, and then cool down to 25 degrees C. at a rate of −10 degrees C./minute. The DSC curve created from this scan is then analyzed using standard techniques to determine the glass transition temperature and the melting temperature.

Method to Determine the Melt Flow Index.

The melt flow index is determined according to the test method detailed in ASTM D1238-13 Standard Test Method for Melt Flow Rates of Thermoplastics by Extrusion Plastometer, using Procedure A described therein. Briefly, the melt flow index measures the rate of extrusion of thermoplastics through an orifice at a prescribed temperature and load. In the test method, approximately 7 grams of the material is loaded into the barrel of the melt flow apparatus, which has been heated to a temperature specified for the material. A weight specified for the material is applied to a plunger and the molten material is forced through the die. A timed extrudate is collected and weighed. Melt flow rate values are calculated in grams/10 min.

Various embodiments of the present disclosure are described below in each of the sets of clauses. For each of the clauses, "disposing" can be replaced with "operably disposing".

Clause 1. An article comprising:
  a bladder having a first bladder wall, the first bladder wall having a first bladder wall thickness, an exterior-facing side comprising a first thermoplastic material, and an interior-facing side comprising a second thermoplastic material, wherein the first bladder wall has a gas transmission rate of 15 $cm^3/m^2 \cdot atm \cdot day$ or less for nitrogen for an average wall thickness of 20 mils; and
  an multi-layer optical film disposed on or within the bladder, wherein the multi-layer optical film has a first side and a second side, wherein the first side and the second side are on opposing sides, wherein the first side or the second side of the multi-layer optical film is disposed on the exterior-facing side of the first bladder wall, on the interior-facing side of the first bladder wall, or on a side of a component in an internal cavity of the bladder, and wherein the first side of the multi-layer optical film, the second side of the multi-layer optical film, or both impart a structural color to the bladder.

Clause 2. The article of clause 1, wherein the exterior-facing side or the interior-facing side of the first bladder wall, or the first side or the second side of the multi-layer optical film, or any combination thereof, comprise a textured surface, and a combination of the textured surface and the multi-layer optical film impart the structural color.

Clause 3. The article of any of the preceding clauses, wherein the textured surface is part of a textured layer or textured structure.

Clause 4. The article of any of the preceding clauses, wherein the multi-layer optical film comprises the textured surface.

Clause 5. The article of any of the preceding clauses, wherein the textured surface, the textured layer or the textured structure is on the first side of the multi-layer optical film, and wherein the first side of the multi-layer optical film is disposed onto the exterior-facing surface of the first bladder wall.

Clause 6. The article of any of the preceding clauses, wherein the textured surface, the textured layer or the textured structure is on the second side of the multi-layer optical film, wherein the first side of the multi-layer optical film is disposed onto the interior-facing surface of the first bladder wall.

Clause 7. The article of any of the preceding clauses, wherein the textured surface has a plurality of topographical structures and plurality of flat areas.

Clause 8. The article of any of the preceding clauses, wherein the textured surface includes a plurality of topographical structures and flat planar areas, and wherein the topographical structures extend above the flat areas of the textured surface.

Clause 9. The article of any of the preceding clauses, wherein the dimensions of the topographical structures, a shape of the topographical structures, a spacing among the plurality of the topographical structures, in combination with the optical layer impart the structural color.

Clause 10. The article of any of the preceding clauses, wherein, over an area of the textured surface having a surface area of at least 5 square millimeters, the topographical structures are in random positions relative to one another.

Clause 11. The article of any of the preceding clauses, wherein spacing among the topographical structures is set to reduce distortion effects of the topographical structures from interfering with one another in the imparted structural color.

Clause 12. The article of any of the preceding clauses, wherein the topographical structures and the flat areas result in at least one optical layer of the multi-layer optical film having an undulating topography, wherein there is a planar region between neighboring depressions, elevations, or both that is planar with the flat planar areas of the textured surface, wherein the planar region has dimensions relative to the topographical structures to impart the structural color.

Clause 13. The article of any of the preceding clauses, wherein the topographical structures and the flat areas cause at least one layer of the multi-layer optical film to have an undulating topography across the textured structure.

Clause 14. The article of any of the preceding clauses, wherein the topographical structures and the flat areas cause each layer of the multi-layer optical film to have an undulating topography across the textured structure.

Clause 15. The article of any of the preceding clauses, wherein the multi-layer optical film includes at least two optical layers.

Clause 16. The article of any preceding article clause, wherein at least one of the layers of the multi-layer optical film comprises or consists essentially of a metal, wherein optionally the metal is selected from titanium or silicon.

Clause 17. The article of any preceding article clause, wherein the multi-layer optical film comprises at least one layer comprising or consisting essentially of a metal oxide, wherein optionally the metal oxide is titanium dioxide or silicon dioxide.

Clause 18. The article of any preceding article claim, wherein the multi-layer optical film comprises at least three layers, including a first layer comprising a metal, and a second layer comprising a metal oxide.

Clause 19. The article of any of the preceding clauses, wherein the multi-layer optical film comprises a multilayer reflector or a multilayer filter.

Clause 20. The article of any of the preceding clauses, wherein the multilayer reflector has at least two layers, including at least two adjacent layers having different refractive indices.

Clause 21. The article of any of the preceding clauses, wherein the refractive indices of the at least two adjacent layers differ by at least 5 percent, optionally at least 10 percent, or optionally at least 15 percent.

Clause 22. The article of any of the preceding clauses, wherein at least one of the layers of the multilayer reflector has a thickness that is about one fourth of the wavelength of visible light to be reflected by the multi-layer optical film to impart the structural color.

Clause 23. The article of any of the preceding clauses, wherein at least one of the layers of the multilayer reflector comprises a material selected from the group consisting of: silicon dioxide, titanium dioxide, zinc sulfide, magnesium fluoride, tantalum pentoxide, and a combination thereof.

Clause 24. The article of any preceding clause, wherein the structural color of the bladder is visible to a viewer having 20/20 visual acuity and normal color vision from a distance of about 1 meter from the bladder.

Clause 25. The article of any preceding clause, wherein the structural color imparted to the bladder has a single hue across the exterior-facing side of the bladder, regardless of viewing angle.

Clause 26. The article of any preceding clause, wherein the structural color imparted to the bladder includes two or more hues, each of the two or more hues being localized to a single region across the exterior-facing side of the bladder, and wherein the two or more hues do not shift as viewing angle is varied.

Clause 27. The article of any preceding clause, wherein the structural color imparted to the bladder is iridescent.

Clause 28. The article of any preceding clause, wherein the structural color of the bladder has limited iridescence.

Clause 29. The article of the preceding clause, wherein the structural color has limited iridescence such that, when each color visible at each possible angle of observation is assigned to a single hue selected from the group consisting of the primary, secondary and tertiary colors on the red yellow blue (RYB) color wheel, all of the assigned hues fall into a single hue group, wherein the single hue group is one of a) green-yellow, yellow, and yellow-orange; b) yellow, yellow-orange and orange; c) yellow-orange, orange, and orange-red; d) orange-red, and red-purple; e) red, red-purple, and purple; f) red-purple, purple, and purple-blue; g) purple, purple-blue, and blue; h) purple-blue, blue, and blue-green; i) blue, blue-green and green; and j) blue-green, green, and green-yellow.

Clause 30. The article of any of the preceding clauses, wherein the multi-layer optical film, as disposed onto the bladder, when measured according to the CIE 1976 color space under a given illumination condition at three observation angles between −15 degrees and +60 degrees, has a first color measurement at a first angle of observation having coordinates $L_1^*$ and $a_1^*$ and $b_1^*$, and a second color measurement at a second angle of observation having coordinates $L_2^*$ and $a_2^*$ and $b_2^*$, and a third color measurement at a third angle of observation having coordinates $L_3^*$ and $a_3^*$ and $b_3^*$, wherein the $L_1^*$, $L_2^*$, and $L_3^*$ values may be the same or different, wherein the $a_1^*$, $a_2^*$, and as* coordinate values may be the same or different, wherein the $b_1^*$, $b_2^*$, and $b_3^*$ coordinate values may be the same or different, and wherein the range of the combined $a_1^*$, $a_2^*$ and as* values is less than about 40% of the overall scale of possible a* values, optionally is less than about 30% of the overall scale of possible a* values, optionally is less than about 20% of the overall scale of possible a* values, or is less than about 10% of the overall scale of possible a* values.

Clause 31. The article of any of the preceding clauses, wherein the multi-layer optical film, as disposed onto the bladder, when measured according to the CIE 1976 color space under a given illumination condition at three observation angles between −15 degrees and +60 degrees, has a first color measurement at a first angle of observation having coordinates $L_1^*$ and $a_1^*$ and $b_1^*$, and a second color measurement at a second angle of observation having coordinates $L_2^*$ and $a_2^*$ and $b_2^*$, and a third color measurement at a third angle of observation having coordinates $L_3^*$ and as* and $b_3^*$, wherein the $L_1^*$, $L_2^*$, and $L_3^*$ values may be the same or different, wherein the $a_1^*$, $a_2^*$, and as* coordinate values may be the same or different, wherein the $b_1^*$, $b_2^*$, and $b_3^*$ coordinate values may be the same or different, and wherein the range of the combined $b_1^*$, $b_2^*$ and $b_3^*$ values is less than about 40% of the overall scale of possible b* values, optionally is less than about 30% of the overall scale of possible b* values, optionally is less than about 20% of the overall scale of possible b* values, or optionally is less than about 10% of the overall scale of possible b* values.

Clause 32. The article of any of the preceding clauses, wherein the multi-layer optical film, as disposed onto the bladder, when measured according to the CIE 1976 color space under a given illumination condition at two observation angles between −15 degrees and +60 degrees, has a first color measurement at a first angle of observation having coordinates $L_1^*$ and $a_1^*$ and $b_1^*$, and a second color measurement at a second angle of observation having coordinates $L_2^*$ and $a_2^*$ and $b_2^*$, wherein the $L_1^*$ and $L_2^*$ values may be the same or different, wherein the $a_1^*$ and $a_2^*$ coordinate values may be the same or different, wherein the $b_1^*$ and $b_2^*$ coordinate values may be the same or different, and wherein the $\Delta E^*_{ab}$ between the first color measurement and the second color measurement is less than or equal to about 100, where $\Delta E^*_{ab} = [(L_1^* - L_2^*)^2 + (a_1^* - a_2^*)^2 + (b_1^* - b_2^*)^2]^{1/2}$, optionally is less than or equal to about 80, or optionally is less than or equal to about 60.

Clause 33. The article of any of the preceding clauses, wherein the multi-layer optical film, as disposed onto the bladder, when measured according to the CIELCH color space under a given illumination condition at three observation angles between −15 degrees and +60 degrees, has a first color measurement at a first angle of observation having coordinates $L_1^*$ and $C_1^*$ and $h_1^\circ$, and a second color measurement at a second angle of observation having coordinates $L_2^*$ and $C_2^*$ and $h_2^\circ$, and a third color measurement at a third angle of observation having coordinates $L_3^*$ and $C_3^*$ and $h_3^\circ$, wherein the $L_1^*$, $L_2^*$, and $L_3^*$ values may be the same or different, wherein the $C_1^*$, $C_2^*$, and $C_3^*$ coordinate values may be the same or different, wherein the $h_1^\circ$, $h_2^\circ$ and $h_3^\circ$ coordinate values may be the same or different, and wherein the range of the combined $h_1^\circ$, $h_2^\circ$ and $h_3^\circ$ values is less than about 60 degrees, optionally is less than about 50 degrees, optionally is less than about 40 degrees, optionally is less than about 30 degrees, or optionally is less than about 20 degrees.

Clause 34. The article of any of the preceding clauses, wherein a primer layer is disposed on the textured surface.

Clause 35. The article of any of the preceding clauses, wherein the primer layer is on the exterior-facing side of the bladder wall or on the interior-facing side of the bladder wall, and the multi-layer optical film is disposed on the primer layer.

Clause 36. The article of any of the preceding clauses, wherein the multi-layer optical film is disposed on the first thermoplastic material of the exterior-facing side or the second thermoplastic material of the interior-facing side of the bladder wall, with the primer layer, the textured surface, or both, positioned between the multi-layer optical film and the first thermoplastic material.

Clause 37. The article of any of the preceding clauses, wherein the primer layer comprises a textured surface, and the textured surface of the primer layer, the primer layer, and the multi-layer optical film impart the structural color.

Clause 38. The article of any of the preceding clauses, wherein the primer layer is a digitally printed layer, an offset printed layer, a pad printed layer, a screen printed layer, a flexographically printed layer, or a heat transfer printed layer.

Clause 39. The article of any of the preceding clauses, wherein the primer layer comprises a paint.

Clause 40. The article of any of the preceding clauses, wherein the primer layer comprises an ink.

Clause 41. The article of any of the preceding clauses, wherein the primer layer comprises a reground, and at least partially degraded polymer.

Clause 42. The article of any of the preceding clauses, wherein the primer layer is an oxide layer.

Clause 43. The article of any of the preceding clauses, wherein the primer layer comprises a metal oxide or a metal oxynitride.

Clause 44. The article of any of the preceding clauses, wherein the metal oxide or metal oxynitride is doped.

Clause 45. The article of any preceding clause, wherein the primer layer consists essentially of a metal oxide, and optionally consists essentially of titanium dioxide.

Clause 46. The article of any preceding clause, wherein the primer layer consists essentially of a doped metal oxide or a doped metal oxynitride or both.

Clause 47. The article of any preceding clause, wherein the primer layer has a thickness of about 1 to about 200 micrometers, or optionally of about 10 to about 100 micrometers, or optionally of about 10 to about 80 micrometers.

Clause 48. The article of any of the preceding clauses, wherein the primer layer is a coating, wherein the coating is a crosslinked coating including a matrix of crosslinked polymers.

Clause 49. The article of any of the preceding clauses, wherein the coating comprises a plurality of solid pigment particles entrapped in the matrix of crosslinked polymers.

Clause 50. The article of any of the preceding clauses, wherein the matrix of crosslinked polymers includes crosslinked elastomeric polymers.

Clause 51. The article of any of the preceding clauses, wherein the crosslinked elastomeric polymers include crosslinked polyurethane homopolymers or copolymers or both.

Clause 52. The article of any of the preceding clauses, wherein the crosslinked polyurethane copolymers include crosslinked polyester polyurethanes.

Clause 53. The article of any of the preceding clauses, wherein, when the solid pigment particles are present, the solid pigment particles are selected from the group consisting of: metal and metal oxide pigments, carbon pigments, clay earth pigments, ultramarine pigments and a combination thereof.

Clause 54. The article of any of the preceding clauses, wherein the coating further comprises a dye.

Clause 55. The article of any of the preceding clauses, wherein, when the dye is present, the dye is an acid dye.

Clause 56. The article of any of the preceding clauses, wherein the coating further comprises a quaternary ammonium compound.

Clause 57. The article of any of the preceding clauses, wherein the quaternary ammonium compound is a tetrabutyl ammonium compound.

Clause 58. The article of any of the preceding clauses, wherein the tetrabutyl ammonium compound is a tetrabutyl ammonium halide.

Clause 59. The article of any of the preceding clauses, wherein the polymeric coating composition, when present, comprises from 1 to 15 weight percent of the quaternary ammonium compound.

Clause 60. The article of any of the preceding clauses, wherein a molar ratio of the acid dye to the quaternary ammonium compound ranges from 3:1 to 1:3 Clause 61. The article of any of the preceding clauses, wherein the molar ratio of the acid dye to the quaternary ammonium compound ranges from 1.5:1 to 1:1.5.

Clause 62. The article of any of the preceding clauses, wherein the matrix of crosslinked polymers of the coating include polyurethane polymers.

Clause 63. The article of any of the preceding clauses, wherein the polyurethane polymers include thermoplastic polyurethane polymers.

Clause 64. The article of any of the preceding clauses, wherein the polyurethane polymers include elastomeric polyurethane polymers.

Clause 65. The article of any of the preceding clauses, wherein the polyurethane polymers include polyester polyurethane copolymers.

Clause 66. The article of any of the preceding clauses, wherein the polyurethane polymers consist essentially of polyester polyurethane copolymers.

Clause 67. The article of any of the preceding clauses, wherein the primer layer has a thickness of about 3 to 200 nanometers.

Clause 68. The article of any of the preceding clauses, wherein the primer layer has a color selected from the group consisting of: black, dark brown, dark red, dark orange, dark yellow, dark green, dark cyan, dark blue, dark violet, grey, dark magenta, dark indigo, tones thereof, tints thereof, shades thereof, and a combination thereof.

Clause 69. The article of any of the preceding clauses, wherein the color of the primer layer is different than the color of the structural color.

Clause 70. The article of any of the preceding clauses, wherein the color of the primer layer is different than the color of the structural color under the criteria of any preceding clause.

Clause 71. The article of any of the preceding clauses, wherein the first polymeric material, the second polymer material, both are a thermoplastic material.

Clause 72. The article of any of the preceding clauses, wherein the thermoplastic material is an elastomeric thermoplastic material.

Clause 73. The article of any of the preceding clauses, wherein the thermoplastic material includes one or more thermoplastic polyurethanes.

Clause 74. The article of any of the preceding clauses, wherein the thermoplastic material includes one or more thermoplastic polyurethanes, polyesters, polyamides, polyolefins, or a combination thereof.

Clause 75. The article of any of the preceding clauses, wherein the elastomeric thermoplastic material includes a polyester polyurethane copolymer.

Clause 76. The article of any of the preceding clauses, wherein the first thermoplastic material and the second thermoplastic material comprise thermoplastic polymers of the same polymer type.

Clause 77. The article of any of the preceding clauses, wherein the first thermoplastic material and the second thermoplastic material comprise thermoplastic polymers of different types.

Clause 78. The article of any of the preceding clauses, wherein the first thermoplastic material comprises thermoplastic polyurethanes, optionally elastomeric thermoplastic polyurethanes, or optionally elastomeric thermoplastic polyester polyurethane copolymers.

Clause 79. The article of any of the preceding clauses, wherein the first thermoplastic material comprises thermoplastic polyester polyurethane copolymers.

Clause 80. The article of any preceding article clause, wherein the first bladder wall includes a barrier membrane including layers of the first thermoplastic material alternating with layers of a third thermoplastic material.

Clause 81. The article of any preceding article clause, wherein the third thermoplastic material includes ethylene vinyl alcohol copolymers.

Clause 82. The article of any of the preceding clauses, wherein the first side of the multi-layer optical film is disposed on the interior-facing side of the first bladder wall, wherein the primer layer is disposed on the second side of the multi-layer optical film.

Clause 83. The article of any of the preceding clauses, wherein the multi-layer optical film is disposed on the exterior-facing side of the first bladder wall, with the primer layer, the textured structure, or both, positioned between the multi-layer optical film and the exterior-facing side of the first bladder wall.

Clause 84. The article of any of the preceding clauses, wherein the bladder includes a component that includes the multi-layer optical film of any of the clauses, optionally a texture surface of any of the clauses, and optionally a primer of any of the clauses in the internal cavity of the bladder.

Clause 85. The article of any of the preceding clauses, wherein the component is selected from a spacer formed of a solid polymeric material, a spacer formed of a foamed polymeric material, a spacer formed of a textile, or a combination thereof.

Clause 86. An article of apparel, comprising a bladder, wherein the bladder is a bladder of any preceding article clause.

Clause 87. An article of sporting equipment comprising a bladder, wherein the bladder is a bladder of any preceding article clause.

Clause 88. An article of footwear, comprising a bladder, wherein the bladder is a bladder of any preceding article clause.

Clause 89. An article of footwear, comprising a sole, wherein the sole includes a bladder of any preceding article clause.

Clause 90. A method of making an article of footwear, apparel or sporting equipment comprising:
  affixing a bladder of any preceding article clause to a second element, forming an article of footwear, apparel or sporting equipment.

Clause 91. The method of any of the preceding clauses, wherein the article is an article of footwear comprising the bladder in a sole, further comprising affixing the sole to an upper to form the article of footwear.

Clause 92. The method of any of the preceding clauses, wherein the method further comprises the step(s) of any of the following method clauses.

Clause 93. A method of making a bladder, comprising:
  disposing an multi-layer optical film onto an exterior-facing side or an interior-facing side of a first bladder wall of a bladder, the bladder wall having a first bladder wall thickness and a gas transmission rate of 15 cm$^3$/m$^2$·atm·day or less for nitrogen for an average wall thickness of 20 mils, wherein the exterior-facing side comprises a first thermoplastic material and the interior-facing side comprises a second thermoplastic material, wherein the first bladder wall has; wherein the multi-layer optical film has a first side and a second side, wherein the first side and the second side are on opposing sides, wherein the first side or the second side of the multi-layer optical film is disposed on the external-facing side of the bladder wall, or the interior-facing side of the first bladder wall, or on a component in an internal cavity of the bladder; and wherein the first side of the multi-layer optical film, the second side of the multi-layer optical film, or both impart a structural color to the bladder.

Clause 94. The method of any of the preceding clauses, wherein the method further comprises forming the bladder by applying heat, pressure, vacuum, or a combination thereof to a film, forming the bladder, wherein the film has a gas transmission rate of 15 cm$^3$/m$^2$·atm·day or less for nitrogen for an average film thickness of 20 mils;
  wherein the step of forming the bladder is conducted prior to or following the disposing the multi-layer optical film onto the exterior-facing side or the internal-facing side of the bladder wall.

Clause 95. The method of any of the preceding clauses, wherein the method further comprises inflating the bladder after the forming the bladder.

Clause 96. The method of any of the preceding clauses, wherein the disposing the multi-layer optical film is conducted prior to inflating the bladder.

Clause 97. The method of any of the preceding clauses, wherein the disposing the multi-layer optical film is conducted on an inflated bladder.

Clause 98. The method of any of the preceding clauses, wherein a temperature of the inflated bladder is maintained at a temperature below a glass transition temperature of the first thermoplastic material during the disposing.

Clause 99. The method of any of the preceding clauses, wherein a temperature of the inflated bladder is maintained at a temperature at or below 80 degrees C. during the disposing.

Clause 100. The method of any of the preceding clauses, wherein the disposing includes disposing the first side of the multi-layer optical film onto the exterior-facing side of the first bladder wall.

Clause 101. The method of any of the preceding clauses, wherein the method further comprises forming a textured surface, a primer layer, or both, on the exterior-facing side of the first bladder wall, or on the interior-facing side of the first bladder wall, prior to the disposing.

Clause 102. The method of any of the preceding clauses, wherein the multi-layer optical film includes a textured surface, a primer layer, or both.

Clause 103. The method of any of the preceding clauses, wherein the disposing includes disposing the first side of the multi-layer optical film onto the interior-facing side of the first bladder wall.

Clause 104. The method of any of the preceding clauses, wherein the interior-facing side of the first bladder wall includes a textured surface.

Clause 105. The method of any of the preceding clauses, wherein the textured surface is part of a textured layer or a textured structure.

Clause 106. The method of any of the preceding clauses, wherein the multi-layer optical film includes the textured layer or textured structure.

Clause 107. The method of any of the preceding clauses, wherein the textured surface is a textured surface according to any preceding article clause.

Clause 108. The method of any of the preceding clauses, wherein the multi-layer optical film is a multi-layer optical film according to any preceding article clause.

Clause 109. The method of any of the preceding clauses, further comprising disposing a primer layer on the exterior-facing side of the first bladder wall or on the interior-facing side of the first bladder wall prior to the disposing the multi-layer optical film; and, the primer layer and the optical layer impart the structural color.

Clause 110. The method of any of the preceding clauses, wherein the exterior-facing side or the interior-facing side includes a textured surface; the method further comprises forming a primer layer on the textured surface prior to the disposing the multi-layer optical film; interior-facingexterior-facinginterior-facingexterior-facingand the textured surface, the primer layer, and the optical layer impart the structural color.

Clause 111. The method of any of the preceding clauses, wherein forming the primer layer comprises forming the primer layer using digital printing, offset printing, pad printing, screen printing, flexographic printing, or heat transfer printing.

Clause 112. The method of any of the preceding clauses, wherein the disposing includes disposing the multi-layer optical film on a component, and the method further comprises placing the structurally colored component within an internal cavity of the bladder prior to inflating the bladder.

Clause 113. The method of any of the preceding clauses, wherein the component is selected from a spacer formed of a solid polymeric material, a spacer formed of a foamed polymeric material, a spacer formed of a textile, or a combination thereof.

Clause 114. The method of any preceding method clause, wherein the article is an article of any preceding article clause.

Clause 115. An article, comprising a bladder formed using the methods of 82-99.

Clause 116. An inflated bladder for use in an article of footwear, the inflated bladder comprising:
    a bladder wall having an interior-facing side and an exterior-facing side, wherein the interior-facing side defines at least a portion of an interior region of the inflated bladder, and wherein the bladder wall further includes an average wall thickness between the interior-facing side and exterior-facing side that is less than 5 millimeters; and
    a multi-layer optical film having a first side and a second opposing side, wherein the first side of the multi-layer optical film is operably disposed on the exterior-facing side of the bladder wall, and wherein the multi-layer optical film imparts a structural color to the bladder wall.

Clause 117. The inflated bladder of any of the preceding clause, wherein the bladder wall exhibits a gas transmission rate of 15 $cm^3/m^2 \cdot atm \cdot day$ or less.

Clause 118. The inflated bladder of any of the preceding clause, wherein the bladder wall further comprises alternating first and second polymeric layers, wherein the first polymeric layers each comprise one or more thermoplastic polyurethanes, and wherein the second polymeric layers each comprise one or more thermoplastic ethylene-vinyl alcohol polymers.

Clause 119. The inflated bladder of any of the preceding clause, wherein the bladder wall comprises one or more thermoplastic polyurethanes.

Clause 120. The inflated bladder of any of the preceding clause, wherein the multi-layer optical film comprises:
    a first layer compositionally comprising a non-oxide metal; and
    a second layer compositionally comprising a first metal oxide.

Clause 121. The inflated bladder of any of the preceding clause, and further comprising a third layer compositionally comprising a second metal oxide that is different from the first metal oxide.

Clause 122. The inflated bladder of any of the preceding clause, wherein the multi-layer optical film comprises:
    a first layer compositionally comprising a first metal oxide; and
    a second layer compositionally comprising a second metal oxide different from the first metal oxide.

Clause 123. The inflated bladder of any of the preceding clause, further comprising a primer layer disposed on the exterior-facing side of the bladder wall, and wherein the first side of the multi-layer optical film is disposed on the primer layer.

Clause 124. The inflated bladder of any of the preceding clause, wherein the primer layer has a thickness ranging from about 10 to about 100 micrometers.

Clause 125. A bladder for use in an article of footwear, the bladder comprising:
- a bladder wall having an interior-facing side and an exterior-facing side, wherein the interior-facing side defines at least a portion of an interior region of the bladder;
- a plurality of topographical structures extending from the exterior-facing side of the bladder wall; and
- a multi-layer optical film having a first side and a second opposing side, wherein the first side of the multi-layer optical film is disposed on the exterior-facing side of the bladder wall and covering the plurality of topographical structures, and wherein the multi-layer optical film imparts a structural color to the bladder wall.

Clause 126. The inflated bladder of any of the preceding clause, wherein the multi-layer optical film comprises:
- a first layer compositionally comprising a first metal oxide, wherein the first layer at least partially conforms to the plurality of topographical structures; and
- a second layer disposed on the first layer and compositionally comprising a second metal oxide different from the first metal oxide.

Clause 127. The inflated bladder of any of the preceding clause, and further comprising a gas retained within the interior region of the bladder.

Clause 128. The inflated bladder of any of the preceding clause, wherein the gas consists essentially of nitrogen.

Clause 129. The inflated bladder of any of the preceding clause, wherein the bladder wall exhibits a gas transmission rate of 15 $cm^3/m^2 \cdot atm \cdot day$ or less.

Clause 130. An article of footwear comprising:
- a footwear upper; and
- an inflated bladder comprising:
    - a top wall operably secured to the footwear upper;
    - a bottom wall opposite the top wall; and
    - one or more sidewalls extending between the top wall and the bottom wall of the inflated bladder, wherein the top wall, the bottom wall, and the one or more sidewalls collectively define an interior region of the inflated bladder, and wherein the one or more sidewalls each comprise an exterior-facing side; and
- a multi-layer optical film operably disposed on the exterior-facing side at least one of the one or more sidewalls to impart a structural color to the one or more sidewalls.

Clause 131. The article of footwear of any of the preceding clauses, wherein the inflated bladder further comprises a plurality of topographical structures extending from the exterior-facing side of at least one of the one or more sidewalls such that the multi-layer optical film covers the plurality of topographical structures.

Clause 132. The article of footwear of any of the preceding clauses, wherein the multi-layer optical film comprises:
- a first layer compositionally comprising a first metal oxide, wherein the first layer at least partially conforms to the plurality of topographical structures; and
- a second layer disposed on the first layer and compositionally comprising a second metal oxide different from the first metal oxide.

Clause 133. The article of footwear of any of the preceding clauses, wherein the structural color imparted to the one or more sidewalls has a single hue regardless of viewing angle.

Clause 134. The article of footwear of any of the preceding clauses, wherein the structural color imparted to the one or more sidewalls has a metallic appearance comprises a metallic color.

Clause 135. The article of footwear of any of the preceding clauses, wherein the structural color imparted to the one or more sidewalls has two or more hues.

Clause 136. A method of making a bladder, comprising:
- disposing an multi-layer optical film onto an exterior-facing side or an interior-facing side of a first bladder wall of a bladder, wherein the interior-facing side defines at least a portion of an interior region of the inflated bladder, and wherein the bladder wall further includes an average wall thickness between the interior-facing side and exterior-facing side that is less than 5 millimeters,
- wherein the multi-layer optical film having a first side and a second opposing side, wherein the first side of the multi-layer optical film is operably disposed on the exterior-facing side of the bladder wall, and wherein the multi-layer optical film imparts a structural color to the bladder wall.

Clause 137. The method of footwear of any of the preceding clauses, wherein the method further comprises forming the bladder by applying heat, pressure, vacuum, or a combination thereof to a film, forming the bladder;
- wherein the step of forming the bladder is conducted prior to or following the operably disposing the multi-layer optical film onto the exterior-facing side or the internal-facing side of the bladder wall.

Clause 138. The method of footwear of any of the preceding clauses, wherein the methods include the articles of the preceding clauses.

Clause 139. A bladder for use in an article of footwear, the bladder comprising:
- a bladder wall having an interior-facing side and an exterior-facing side, wherein the interior-facing side defines at least a portion of an interior region of the bladder;
- a plurality of topographical structures extending from the exterior-facing side of the bladder wall; and
- a multi-layer optical film having a first side and a second opposing side, wherein the first side of the multi-layer optical film is disposed on the exterior-facing side of the bladder wall and covering the plurality of topographical structures, and wherein the multi-layer optical film imparts a structural color to the bladder wall.

Clause 140. A method of making a bladder, comprising:
- disposing an multi-layer optical film onto an exterior-facing side or an interior-facing side of a first bladder wall of a bladder, wherein the interior-facing side defines at least a portion of an interior region of the inflated bladder, wherein a plurality of topographical structures extending from the exterior-facing side of the bladder wall, wherein the multi-layer optical film having a first side and a second opposing side, wherein the first side of the multi-layer optical film is disposed on the exterior-facing side of the bladder wall and covering the plurality of topographical structures, and wherein the multi-layer optical film imparts a structural color to the bladder wall.

Clause 141. A method of making an article of footwear comprising:
- operably securing an inflated bladder to a top wall of a footwear upper, wherein the bladder comprises the top wall, a bottom wall opposite the top wall; and one or more sidewalls extending between the top wall and the bottom wall of the inflated bladder, wherein the top wall, the bottom wall, and the one or more sidewalls collectively define an interior region of the inflated bladder, and wherein the one or more sidewalls each comprise an exterior-facing side; and a multi-layer optical film operably disposed on the exterior-facing side at least one of the one or more sidewalls to impart a structural color to the one or more sidewalls.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1 percent to about 5 percent" should be interpreted to include not only the explicitly recited concentration of about 0.1 weight percent to about 5 weight percent but also include individual concentrations (e.g., 1 percent, 2 percent, 3 percent, and 4 percent) and the sub-ranges (e.g., 0.5 percent, 1.1 percent, 2.2 percent, 3.3 percent, and 4.4 percent) within the indicated range. The term "about" can include traditional rounding according to significant figures of the numerical value. In addition, the phrase "about 'x' to 'y'" includes "about 'x' to about y".

Many variations and modifications may be made to the above-described aspects. All such modifications and variations are intended to be included herein within the scope of this disclosure and protected by the following claims.

What is claimed is:

1. An article of footwear comprising:
   a footwear upper; and
   an inflated bladder comprising:
     a top wall operably secured to the footwear upper;
     a bottom wall opposite the top wall; and
     one or more sidewalls extending between the top wall and the bottom wall of the inflated bladder, wherein the top wall, the bottom wall, and the one or more sidewalls collectively define an interior region of the inflated bladder, and wherein the one or more sidewalls each comprise an interior-facing side and an exterior-facing side; and
     a multi-layer optical film operably disposed on the interior-facing side or exterior-facing side of at least one of the one or more sidewalls to impart a structural color having at least one hue to the one or more sidewalls;
   wherein the multi-layer optical film comprises:
     a first layer compositionally comprising a non-oxide metal; and
     a second layer disposed on the first layer and compositionally comprising a first metal oxide; and
   wherein the multi-layer optical film is a multi-layer reflector or a multi-layer filter comprising at least two adjacent layers having different refractive indices and at least one of the layers of the multi-layer reflector or filter has a thickness that is about one-fourth of the wavelength of the visible light to be reflected by the multi-layer optical film to produce the structural color.

2. The article of footwear of claim 1, wherein the first metal oxide is titanium dioxide or silicon dioxide.

3. The article of footwear of claim 1, wherein the multi-layer optical film comprises:
   a third layer compositionally comprising a second metal oxide that is different from the first metal oxide.

4. The article of footwear of claim, wherein at least one of the layers of the multilayer reflector or multi-layer filter comprises a material selected from the group consisting of: silicon dioxide, titanium dioxide, zinc sulfide, magnesium fluoride, tantalum pentoxide, and a combination thereof.

5. The article of footwear of claim 1, wherein the structural color imparted to the one or more sidewalls has a single hue regardless of viewing angle.

6. The article of footwear of claim 1, wherein the structural color imparted to the one or more sidewalls has a metallic appearance.

7. The article of footwear of claim 1, wherein the structural color imparted to the one or more sidewalls has two or more hues.

8. The article of footwear of claim 1, wherein each color visible at each possible angle of observation is assigned to a single hue selected from the group consisting of the primary, secondary and tertiary colors on the red yellow blue (RYB) color wheel, all of the assigned hues fall into a single hue group, wherein the single hue group is one of a) green-yellow, yellow, and yellow-orange; b) yellow, yellow-orange and orange; c) yellow-orange, orange, and orange-red; d) orange-red, and red-purple; e) red, red-purple, and purple; f) red-purple, purple, and purple-blue; g) purple, purple-blue, and blue; h) purple-blue, blue, and blue-green; i) blue, blue-green and green; and j) blue-green, green, and green-yellow.

9. The article of footwear of claim 1, wherein the structural color produced by the multi-layer optical film is different from the color of the underlying bladder wall.

10. The article of footwear of claim 1, wherein the multi-layer optical film contains no pigments and no dyes.

11. The article of footwear of claim 1, wherein the bladder wall further includes an average wall thickness between the interior-facing side and exterior-facing side that is less than 5 millimeters.

12. The article of footwear of claim 1, wherein the multi-layer optical film has from 2 to 20 layers, each layer independently having a thickness of about 10 to 500 nanometers.

13. The article of footwear of claim 1, wherein the multi-layer optical film has from 2 to 20 layers, each layer independently having a thickness of about 10 to 500 nanometers, wherein the multi-layer optical film contains no pigments and no dyes, and the structural color produced by the multi-layer optical film is a single-hued color.

14. The article of footwear of claim 1, further comprising a primer layer disposed on the multi-layer optical film.

15. The article of footwear of claim 1, wherein the multi-layer optical film, as disposed onto the bladder, when measured according to the CIE 1976 color space under a given illumination condition at two observation angles between −15 degrees and +60 degrees, has a first color measurement at a first angle of observation having coordinates $L_1^*$ and $a_1^*$ and $b_1^*$, and a second color measurement at a second angle of observation having coordinates $L_2^*$ and $a_2^*$ and $b_2^*$, wherein the $L_1^*$ and $L_2^*$ values may be the same or different, wherein the $a_1^*$ and $a_2^*$ coordinate values may be the same or different, wherein the $b_1^*$ and $b_2^*$ coordinate values may be the same or different, and wherein the $\Delta E^*_{ab}$ between the first color measurement and the second color measurement is less than or equal to about 100, where $\Delta E^*_{ab} = [(L_1^* - L_2^*)^2 + (a_1^* - a_2^*)^2 + (b_1^* - b_2^*)^2]^{1/2}$.

16. The article of footwear of claim 1, wherein the inflated bladder further comprises a plurality of topographical structures extending from the interior-facing or exterior-facing side of at least one of the one or more sidewalls such that the multi-layer optical film covers the plurality of topographical structures.

17. The article of footwear of claim 16, wherein the first side of the multi-layer optical film covers the plurality of topographical structures, and the first layer of the multi-layer optical film at least partially conforms to the plurality of topographical structures.

18. The article of footwear of claim 1, further comprising a gas retained within the interior region of the bladder.

19. The article of footwear of claim 18, wherein the gas consists essentially of nitrogen.

20. The article of footwear of claim 18, wherein the bladder wall exhibits a gas transmission rate of 15 $cm^3/m^2 \cdot atm \cdot day$ or less for an average wall thickness of 20 mils.

* * * * *